US011820761B2

(12) United States Patent
Yoo et al.

(10) Patent No.: US 11,820,761 B2
(45) Date of Patent: Nov. 21, 2023

(54) ORGANIC COMPOUND, ORGANIC LIGHT EMITTING DIODE AND ORGANIC LIGHT EMITTING DEVICE INCLUDING THE ORGANIC COMPOUND

(71) Applicant: LG DISPLAY CO., LTD., Seoul (KR)

(72) Inventors: Mi-Sang Yoo, Paju-si (KR); Kyung-Jin Yoon, Paju-si (KR); Dae-Wi Yoon, Paju-si (KR); In-Ae Shin, Paju-si (KR); Suk-Young Bae, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 538 days.

(21) Appl. No.: 17/012,363

(22) Filed: Sep. 4, 2020

(65) Prior Publication Data

US 2021/0070740 A1 Mar. 11, 2021

(30) Foreign Application Priority Data

Sep. 6, 2019 (KR) ........................ 10-2019-0110896

(51) Int. Cl.
*C07D 407/10* (2006.01)
*C07C 13/62* (2006.01)
(Continued)

(52) U.S. Cl.
CPC ............ *C07D 407/10* (2013.01); *C07C 13/62* (2013.01); *C07C 211/61* (2013.01);
(Continued)

(58) Field of Classification Search
CPC ................ C07D 407/10; C07D 307/91; C07D 401/12; C07D 403/10; C07C 13/62;
(Continued)

(56) References Cited

U.S. PATENT DOCUMENTS

| | | | | |
|---|---|---|---|---|
| 7,175,922 B2 | 2/2007 | Jarikov et al. | | |
| 2001/0025819 A1* | 10/2001 | Bowser | B01D 61/24 | |
| | | | 210/640 | |

(Continued)

FOREIGN PATENT DOCUMENTS

| | | |
|---|---|---|
| JP | 2002025778 A * | 1/2002 |
| JP | 2002025778 A | 1/2002 |

(Continued)

OTHER PUBLICATIONS

Translation of First Office Action dated Nov. 28, 2022, issued in corresponding Chinese Intellectual Property Office dated Nov. 28, 2022 for CN App No. 202010921694.8.

(Continued)

*Primary Examiner* — Michael M. Bernshteyn
(74) *Attorney, Agent, or Firm* — Morgan, Lewis & Bockius LLP

(57) ABSTRACT

The present disclosure relates to an organic compound having the following structure, and an organic light emitting diode (OLED) and an organic light emitting device including the organic compound. Applying the organic compound into an emissive layer makes the OLED and the organic light emitting device lower their driving voltage, improves their luminous efficiency and color purity.

(Continued)

22 Claims, 11 Drawing Sheets

(51) Int. Cl.

| | |
|---|---|
| ***C07C 211/61*** | (2006.01) |
| ***C07D 307/91*** | (2006.01) |
| ***C07D 401/12*** | (2006.01) |
| ***C07D 403/10*** | (2006.01) |
| ***H10K 50/11*** | (2023.01) |
| ***H10K 85/60*** | (2023.01) |
| ***H10K 101/10*** | (2023.01) |

(52) U.S. Cl.
CPC ......... *C07D 307/91* (2013.01); *C07D 401/12* (2013.01); *C07D 403/10* (2013.01); *H10K 50/11* (2023.02); *H10K 85/631* (2023.02); *H10K 85/654* (2023.02); *H10K 85/6572* (2023.02); *H10K 85/6574* (2023.02); *H10K 2101/10* (2023.02)

(58) Field of Classification Search
CPC .... C07C 211/61; H01K 50/11; H01K 85/631; H01K 85/654; H01K 85/6572; H01K 85/6574; H01K 2101/10
USPC .......................................................... 428/690
See application file for complete search history.

(56) References Cited

U.S. PATENT DOCUMENTS

| | | | | |
|---|---|---|---|---|
| 2003/0104150 | A1* | 6/2003 | Bonnet .................. | C08L 27/16 252/511 |
| 2009/0072727 | A1* | 3/2009 | Takeda ................ | H10K 85/655 313/504 |
| 2016/0087227 | A1* | 3/2016 | Kim .................. | H10K 85/6565 257/40 |

FOREIGN PATENT DOCUMENTS

| | | | | |
|---|---|---|---|---|
| JP | 2002056979 | A | * | 2/2002 |
| JP | 2002056979 | A | | 2/2002 |
| JP | 2009070985 | A | * | 4/2009 |
| JP | 2009070985 | A | | 4/2009 |

OTHER PUBLICATIONS

Extended European Search Report dated Jan. 26, 2021, issued in corresponding European Patent Application No. 20193841.2.

* cited by examiner

ORGANIC COMPOUND, ORGANIC LIGHT EMITTING DIODE AND ORGANIC LIGHT EMITTING DEVICE INCLUDING THE ORGANIC COMPOUND

CROSS-REFERENCE TO RELATED APPLICATIONS

This application claims the priority benefit under 35 U.S.C. § 119(a) of Korean Patent Application No. 10-2019-0110896, filed in the Republic of Korea on Sep. 6, 2019, which is incorporated herein by reference in its entirety.

BACKGROUND

Technical Field

The present disclosure relates to an organic compound, and more specifically, to an organic compound having enhanced luminous properties, an organic light emitting diode and an organic light emitting device including the compound.

Discussion of the Related Art

As display devices have become larger, there exists a need for a flat display device with a lower space requirement. Among the flat display devices used widely at present, organic light emitting diodes (OLEDs) are rapidly replacing liquid crystal display devices (LCDs).

In the OLED, when electrical charges are injected into an emitting material layer between an electron injection electrode (i.e., cathode) and a hole injection electrode (i.e., anode), electrical charges are recombined to form excitons, and then emit light as the recombined excitons are shifted to a stable ground state. The OLED can be formed as a thin film having a thickness less than 2000 Å and can implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, thus it has attracted a lot of attention as a light emitting device.

However, the luminous materials applied into the OLED have not shown satisfactory luminous efficiency. Also, the OLED in which the luminous materials are applied has driven at relatively higher driving voltages, thus it has increased power consumption. In addition, the luminous material applied into the OLED has short luminous lifetime or bad color purity.

SUMMARY

Accordingly, embodiments of the present disclosure are directed to an organic compound and an OLED and an organic light emitting device including the organic compound that substantially obviate one or more of the problems due to the limitations and disadvantages of the related art.

An aspect of the present disclosure is to provide an organic compound having excellent luminous efficiency and color purity, an OLED and an organic light emitting device into which the organic compound is applied.

Another aspect of the present disclosure is to provide an organic compound that can be driven at low voltage and reduce power consumption, an OLED and an organic light emitting device having the compound.

Additional features and aspects will be set forth in the description that follows, and in part will be apparent from the description, or may be learned by practice of the inventive concepts provided herein. Other features and aspects of the inventive concept may be realized and attained by the structure particularly pointed out in the written description, or derivable therefrom, and the claims hereof as well as the appended drawings.

To achieve these and other aspects of the inventive concepts, as embodied and broadly described, the present disclosure provides an organic compound having the following structure of Chemical Formula 1:

[Chemical Formula 1]

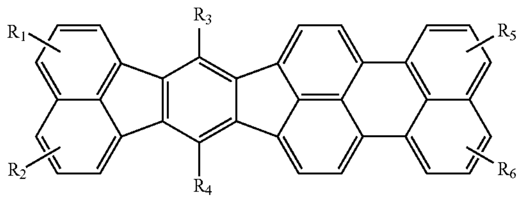

wherein each of $R_1$ and $R_2$ is independently hydrogen, an unsubstituted or substituted $C_1$-$C_{20}$ alkyl group, an unsubstituted or substituted $C_1$-$C_{20}$ alkoxy group, an unsubstituted or substituted aromatic group or an unsubstituted or substituted hetero aromatic group; each of $R_3$ and $R_4$ is independently an unsubstituted or substituted aromatic group or an unsubstituted or substituted hetero aromatic group; and each of $R_5$ and $R_6$ is independently hydrogen, an unsubstituted or substituted $C_1$-$C_{10}$ alkyl group, an unsubstituted or substituted $C_1$-$C_{10}$ alkoxy group, an unsubstituted or substituted aromatic group or an unsubstituted or substituted hetero aromatic group, wherein the aromatic group is a group which has one or more $C_6$-$C_{30}$ aryl groups, optionally comprises a $C_6$-$C_{30}$ aryl group, an alkyl group substituted with one or more $C_6$-$C_{30}$ aryl groups, a $C_6$-$C_{30}$ aryloxyl group, an amino group substituted with one or more $C_6$-$C_{30}$ aryl groups, and combination thereof, wherein the hetero aromatic group is a group which has one or more $C_3$-$C_{30}$ hetero aryl groups, optionally comprises a $C_3$-$C_{30}$ hetero aryl group, an alkyl group substituted with one or more $C_3$-$C_{30}$ hetero aryl groups, a $C_3$-$C_{30}$ hetero aryloxyl group, an amino group substituted with one or more $C_3$-$C_{30}$ hetero aryl groups, and combination thereof.

In another aspect, the present disclosure provides an OLED that comprises a first electrode; a second electrode facing the first electrode; and at least one emitting unit disposed between the first and second electrodes and comprising a first emitting material layer, wherein the first emitting material layer comprise the organic compound.

For example, the organic compound may be comprised in a first emitting material layer as a dopant.

In still another aspect, the present disclosure provides an organic light emitting device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION

Figure 1:
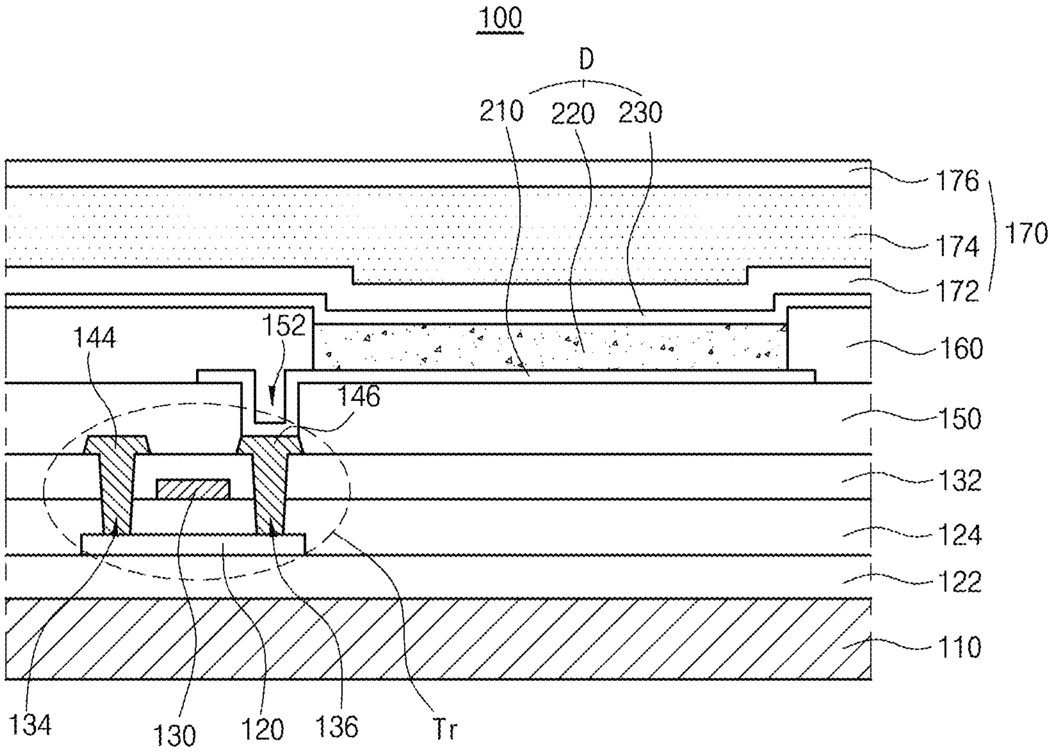
FIG. 1 is a schematic cross-sectional view illustrating an organic light emitting display device of the present disclosure.

Reference will now be made in detail to aspects of the disclosure, examples of which are illustrated in the accompanying drawings.

[Organic Compound]

An organic compound applied to an organic light emitting diode (OLED) should have excellent luminous properties, affinity to charges and maintain stable properties to in driving the OLED. Particularly, luminous materials applied in the diode the most important factor determining the luminous efficiency of the OLED. The luminous material should have high quantum efficiency, large mobility for charges and adequate energy levels with regard to other materials applied in the same or adjacent layers. An organic compound in accordance with the present disclosure may have the following structure of Chemical Formula 1:

[Chemical Formula 1]

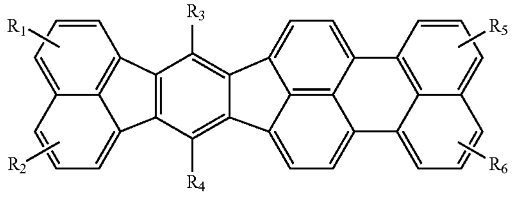

In Chemical Formula 1, each of $R_1$ and $R_2$ is independently hydrogen, an unsubstituted or substituted $C_1$-$C_{20}$ alkyl group, an unsubstituted or substituted $C_1$-$C_{20}$ alkoxy group, an unsubstituted or substituted aromatic group or an unsubstituted or substituted hetero aromatic group; each of $R_3$ and $R_4$ is independently an unsubstituted or substituted aromatic group or an unsubstituted or substituted hetero aromatic group; and each of $R_5$ and $R_6$ is independently hydrogen, an unsubstituted or substituted $C_1$-$C_{10}$ alkyl group, an unsubstituted or substituted $C_1$-$C_{10}$ alkoxy group, an unsubstituted or substituted aromatic group or an unsubstituted or substituted hetero aromatic group, wherein the aromatic group is a group which has one or more $C_6$-$C_{30}$ aryl groups, optionally comprises a $C_6$-$C_{30}$ aryl group, an alkyl group substituted with one or more $C_6$-$C_{30}$ aryl groups, a $C_6$-$C_{30}$ aryloxyl group, an amino group substituted with one or more $C_6$-$C_{30}$ aryl groups, and combination thereof, wherein the hetero aromatic group is a group which has one or more $C_3$-$C_{30}$ hetero aryl groups, optionally comprises a $C_3$-$C_{30}$ hetero aryl group, an alkyl group substituted with one or more $C_3$-$C_{30}$ hetero aryl groups, a $C_3$-$C_{30}$ hetero aryloxyl group, an amino group substituted with one or more $C_3$-$C_{30}$ hetero aryl groups, and combination thereof.

As used herein, the term "unsubstituted" means that a group has only hydrogen as a substituent, and in this case, hydrogen comprises protium, deuterium and tritium.

As used the term "substituted" herein, the substitution group comprises, but is not limited to, unsubstituted or halogen-substituted $C_1$-$C_{20}$ alkyl, unsubstituted or halogen-substituted $C_1$-$C_{20}$ alkoxy, halogen, cyano, $-CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term "hetero" in such as "a hetero aromatic ring", "a hetero cycloalkyene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted at least one hetero atom which may be selected from the group consisting of N, O, S, P and combination thereof.

In one exemplary aspect, the aromatic group in each of $R_1$ to $R_6$ is a group which has one or more $C_6$-$C_{30}$ aryl groups therein, and which may comprise a $C_6$-$C_{30}$ aryl group, an alkyl group substituted with one or more $C_6$-$C_{30}$ aryl groups, a $C_6$-$C_{30}$ aryloxyl group and an amino group substituted with one or more $C_6$-$C_{30}$ aryl groups, and combination thereof. The hetero aromatic group in each of $R_1$ to $R_6$ is a group which has one or more $C_3$-$C_{30}$ hetero aryl groups therein, and which may comprise a $C_3$-$C_{30}$ hetero aryl group, an alkyl group substituted with one or more $C_3$-$C_{30}$ hetero aryl groups, a $C_3$-$C_{30}$ hetero aryloxyl group, an amino group substituted with one or more $C_3$-$C_{30}$ hetero aryl groups, and combination thereof.

In one exemplary aspect, the $C_6$-$C_{30}$ aryl group in each of $R_1$ to $R_6$ may comprise independently, but is not limited to, an unfused or fused aryl group such as phenyl, biphenyl, terphenyl, naphthyl, anthracenyl, pentalenyl, indenyl, indenoindenyl, heptalenyl, biphenylenyl, indacenyl, phenalenyl, phenanthrenyl, benzophenanthrenyl, dibenzophenanthrenyl, azulenyl, pyrenyl, fluoranthenyl, triphenylenyl, chrysenyl, tetraphenylenyl, tetracenyl, pleiadenyl, pycenyl, pentaphenylenyl, pentacenyl, fluorenyl, indenofluorenyl and spiro-fluorenyl.

In another exemplary aspect, the $C_3$-$C_{30}$ hetero aryl group in each of $R_1$ to $R_6$ may comprise independently, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, carbolinyl, quinolinyl, iso-quinolinyl, phthlazinyl, quinoxalinyl, cinnolinyl, quinazolinyl, quinolizinyl, purinyl, benzoquinolinyl, benzoiso-quinolinyl, benzoquinazolinyl, benzoquinoxalinyl, acridinyl, phenazinyl, phenoxazinyl, phenothiazinyl, phenanthrolinyl, perimidinyl, phenanthridinyl, phtheridinyl, naphthyridinyl, furanyl, pyranyl, oxazinyl, oxazolyl, oxadiazolyl, triazolyl, dioxinyl, benzofuranyl, dibenzofuranyl, thiopyranyl, xanthenyl, chromenyl, iso-chromenyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, benzothienodibenzofuranyl, xanthane-linked spiro acridinyl, dihydroacridinyl substituted with at least one $C_1$-$C_{10}$ alkyl and N-substituted spiro fluorenyl.

As an example, each of the aromatic group and the hetero aromatic group in each of $R_1$ to $R_6$ may have independently one to three aromatic or hetero aromatic rings. When the number of the aromatic or the hetero aromatic ring in each of $R_1$ to $R_6$ becomes large, the conjugated structure within the whole molecule is too long, and therefore the organic compound may have excessively reduced energy bandgap. With regard charge injection and transfer property, each of the aromatic group and the hetero aromatic group may comprise a 5-membered ring, a 6-membered ring or 7-membered ring.

The organic compound having the structure of Chemical Formula 1 comprises a solid naphtha-indaceno-perylene core, and thus has excellent thermal resistance. In addition, since the organic compound has less plate-like structure as a whole, there exist less overlapping regions among the adjacent molecules.

The exciton energy among the luminous material may be transferred by Dexter energy transfer mechanism and FRET (Forster resonance energy transfer) mechanism. In FRET mechanism, only singlet exciton energy is transferred non-radiatively through electrical field caused by dipole-dipole interaction. On the contrary, triplet exciton energy as well as singlet exciton energy is transferred via Dexter energy transfer mechanism with exchanging directly electrons among the luminous materials. The molecules should be adjacently disposed less than 10 Å in order to transfer exciton energy in Dexter energy transfer mechanism.

When the organic compound is used as a dopant in an emissive layer of the OLED, triplet exciton energy is transferred with exchanging electrons among adjacently disposed molecules in Dexter energy transfer mechanism. Owing to the reduced overlapping regions among the adjacent molecules, Dexter energy transfer mechanism in which triplet exciton energy of the host and other luminous materials is transferred to the triplet state of the organic compound is limited in case of using the organic compound as the ultimate luminous material. On the contrary, singlet exciton energy, not the triplet exciton energy, of the host and other luminous materials is likely to be transferred to the single state of the organic compound via FRET mechanism.

The organic compound having the structure of Chemical Formula 1 cannot utilize the triplet exciton energy because it is fluorescent material. The triplet exciton energy transferred to the organic compound via Dexter energy transfer mechanism cannot contribute to the luminescence of the organic compound. On the other hand, the singlet exciton energy transferred to the organic compound can participate in the luminescence process of the organic compound. As the Dexter energy transfer mechanism in which triplet exciton energy not contributing to the luminescence of the organic compound having the structure of Chemical Formula 1 is limited and singlet exciton energy is transferred to the organic compound via FRET mechanism which transfers only singlet-singlet exciton energy, the amount of exciton energies that can be utilized by the organic compound for luminescence is increased. When the organic compound is used as the ultimate luminous material, i.e. dopant in the emitting material layer (EML), the OLED can its luminous efficiency and luminous lifetime.

In one exemplary aspect, an unsubstituted or substituted aromatic amino group or hetero amino group is bonded to the napthoindacenoperylene core. The conformation of the molecule substituted with aromatic or hetero aromatic amino group is changed from the plate-like structure to a bended structure, thus adjacent molecules are spaced apart in the organic compound substituted with aromatic or hetero aromatic amino group.

Exciton energy is transferred within very short distance (10 nm or less) via Dexter energy transfer mechanism. As the distance among adjacent molecules are distant in the organic compound substituted with the amino group, triplet exciton energy from the host or other luminous material via Dexter energy transfer mechanism is little transferred, singlet exciton energy from the host or other luminous material via FRET is much increased. As the amount of singlet exciton energies that can be utilized by the organic compound is much increased, the luminous efficiency and luminous lifetime of the OLED can be improved. In addition, as the emission peak of the organic compound substituted with the aromatic or hetero aromatic amino group is shifted to much longer wavelength, its color purity can be enhanced.

In one exemplary aspect, the organic compound may have, but is not limited to maximum photoluminescence wavelength (PL $\lambda_{max}$) between about 580 nm and about 650 nm, e.g., about 580 nm to about 620 nm. Also, the organic compound may have, but is not limited to, maximum absorption wavelength (Abs. $\lambda_{max}$) between about 530 nm to about 590 nm, e.g. about 540 nm to about 580 nm.

In one exemplary aspect, each of $R_1$ and $R_2$ may be independently hydrogen, a $C_1$-$C_{20}$ alkyl group, a $C_6$-$C_{30}$ aryl amino group or a $C_3$-$C_{30}$ hetero aryl amino group. In this case, each of the aromatic ring and the hetero aromatic ring in the $C_6$-$C_{30}$ aryl amino group and/or the $C_3$-$C_{30}$ hetero aryl amino group may be unsubstituted or substituted with at least one group selected from cyano, $C_1$-$C_{10}$ alkyl, $C_1$-$C_{10}$ alkoxy, $C_6$-$C_{30}$ aryl and $C_3$-$C_{30}$ hetero aryl.

In another exemplary aspect, each of $R_3$ and $R_4$ may be independently selected from an aromatic group and a hetero aromatic group each of which is independently unsubstituted or substituted with at least one selected from $C_1$-$C_{10}$ alkyl and $C_1$-$C_{10}$ alkoxy.

In one exemplary aspect, when the number of the aromatic or the hetero aromatic ring constituting the Ar become large, the conjugated structure within the whole molecule is too long, and therefore the organic compound may have excessively reduced energy bandgap. Accordingly, the Ar may have one to three aromatic or hetero aromatic rings, preferably one or two aromatic or hetero aromatic rings. With regard charge injection and transfer, the Ar may comprise 5-membered to 7-membered rings, and particularly a 6-membered ring. For example, the Ar may comprise, but is not limited to, phenylene, biphenylene, naphthylene, anthracenylene, pyrrolylene, imidazolylene, pyrazolylene, pyridinylene, pyrazinlylene, pyrimidinylene, pyridazinlylene, furanylene and thiophenylene.

In one exemplary aspect, the organic compound having the structure of Chemical Formula 1 may have an aromatic amino group and/or a hetero aromatic amino group substituted to the naphtho moiety of the core. Such an organic compound may have the following structure of Chemical Formula 2:

[Chemical Formula 2]

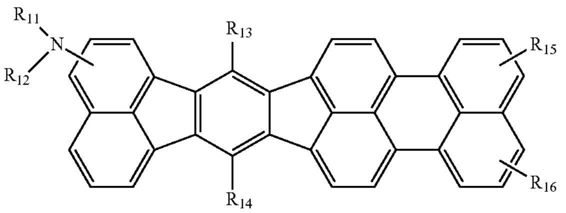

In Chemical Formula 2, each of $R_{11}$ and $R_{12}$ is independently an unsubstituted or substituted $C_6$-$C_{30}$ aryl group or an unsubstituted or substituted $C_3$-$C_{30}$ hetero aryl group; each of $R_{13}$ and $R_{14}$ is independently an unsubstituted or substituted $C_6$-$C_{30}$ aryl group, an unsubstituted or substituted $C_3$-$C_{30}$ hetero aryl group, an unsubstituted or substituted $C_7$-$C_{30}$ aryl alkyl group, an unsubstituted or substituted $C_4$-$C_{30}$ hetero aryl alkyl group, an unsubstituted or substituted $C_6$-$C_{30}$ aryloxyl group or an unsubstituted or substituted $C_3$-$C_{30}$ hetero aryloxyl group; and each of $R_{15}$ and $R_{16}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{30}$ hetero aryl group.

As an example, each of the $C_6$-$C_{30}$ aryl group or the $C_3$-$C_{30}$ hetero aryl group in $R_{11}$ and $R_{12}$ may be independently unsubstituted or substituted with at least one selected from cyano, a $C_1$-$C_{10}$ alkyl group, a $C_1$-$C_{10}$ alkoxy group and a $C_6$-$C_{30}$ aryl group. More particularly, the aryl group substituted to the nitrogen atom of the aromatic amino group may be selected from phenyl, biphenyl, naphthyl, anthracenyl and the like, the hetero aryl group substituted to the nitrogen atom of the hetero aromatic amino group may be selected pyridyl, carbazolyl, acridinyl, phenazinyl, phenoxazinyl, dibenzofuranyl, dibenzothiophenyl, and the like. Such an organic compound may have the following structure of Chemical Formula 3:

[Chemical Formula 3]

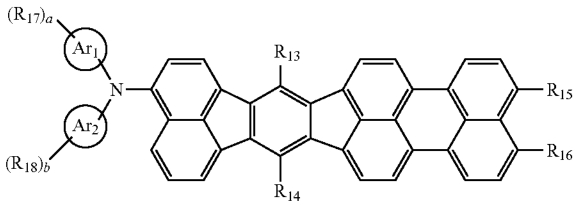

In Chemical Formula 3, each of $R_{13}$ to $R_{16}$ is independently identical as defined in Chemical Formula 2; each of $Ar_1$ and $Ar_2$ is independently selected from the group consisting of phenyl, biphenyl, naphthyl, anthracenyl, pyridyl, carbazolyl, acridinyl, phenazinyl, phenoxazinyl, dibenzofuranyl and dibenzothiophenyl; each of $R_{17}$ and $R_{18}$ is independently hydrogen, cyano, an unsubstituted or substituted $C_1$-$C_{10}$ alkyl group, an unsubstituted or substituted $C_1$-$C_{10}$ alkoxy group, an unsubstituted or substituted $C_6$-$C_{30}$ aryl group or an unsubstituted or substituted $C_3$-$C_{30}$ hetero aryl group; each of a and b is the number of substituent and an integer of 0 (zero) to 4.

In one exemplary aspect, the organic compound having the structure of Chemical Formula 1 may comprise an organic compound in which the naphtho moiety of the core is unsubstituted or substituted with an aromatic or hetero aromatic amino group and the central benzene ring of the indaceno moiety is substituted with an aromatic group. More particularly, the organic compound having the structure of Chemical Formula 1 may anyone having the following structure of Chemical Formula 4:

[Chemical Formula 4]

1-1

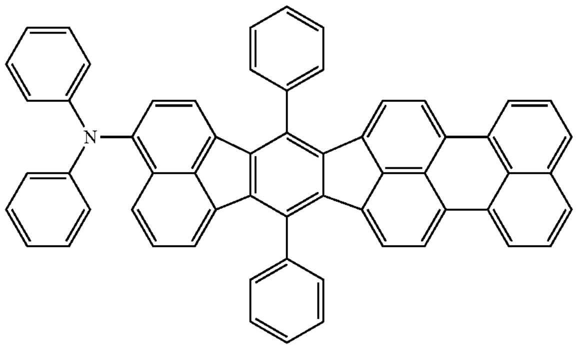

-continued
1-2
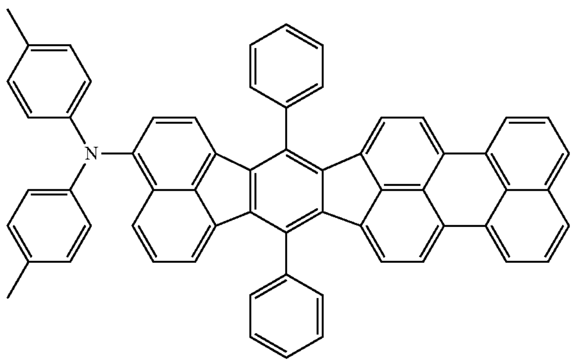
1-3
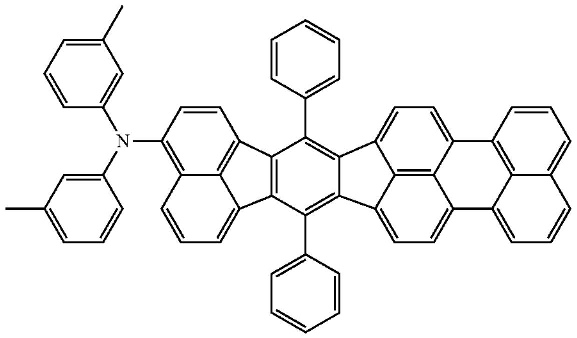
1-4
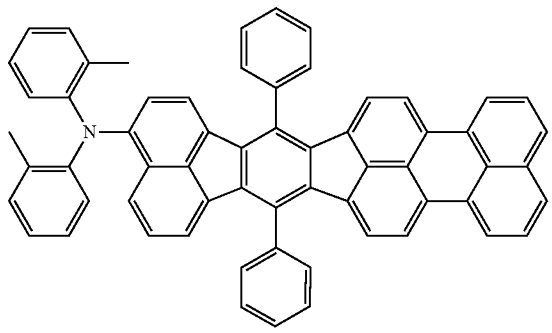
1-5
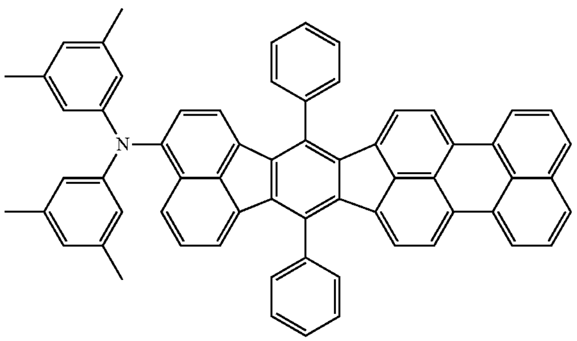
-continued
1-6
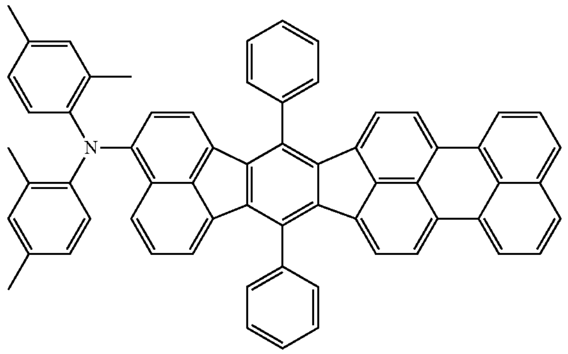
1-7
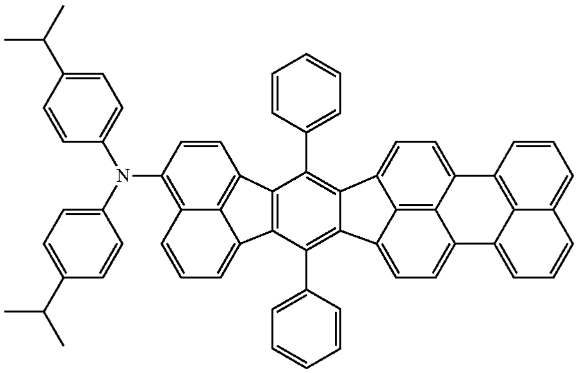
1-8
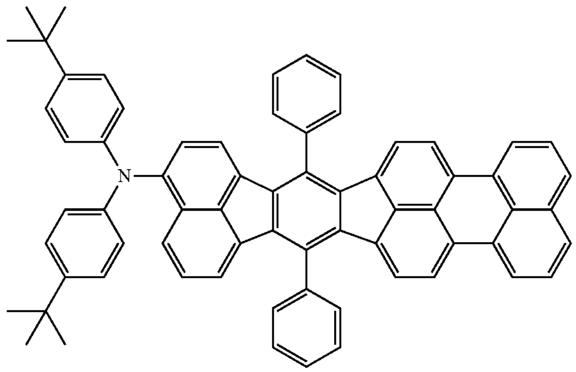
1-9
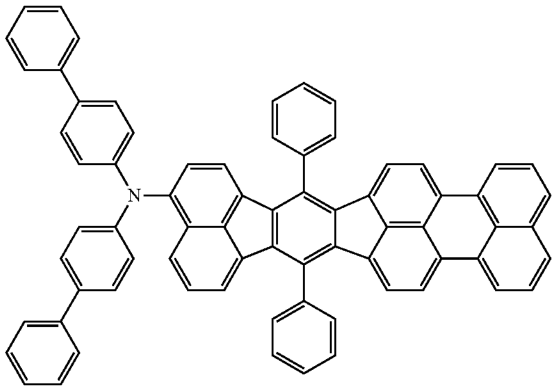

-continued
1-10
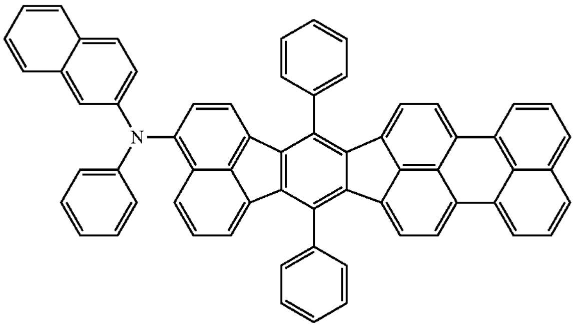
1-11
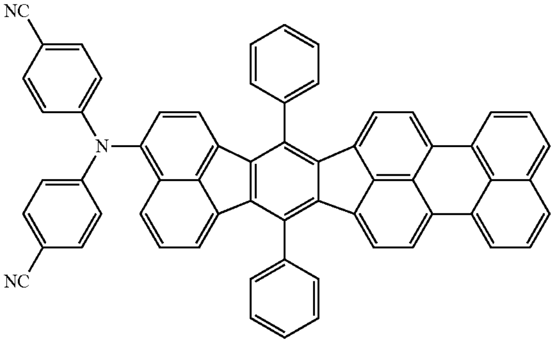
1-12
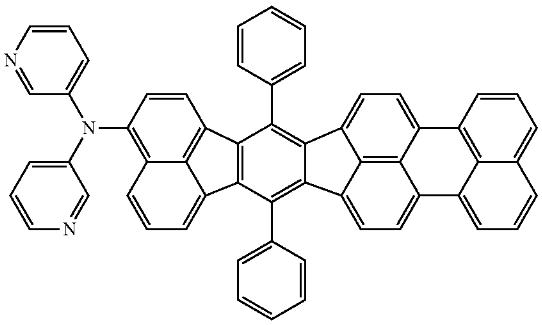
1-13
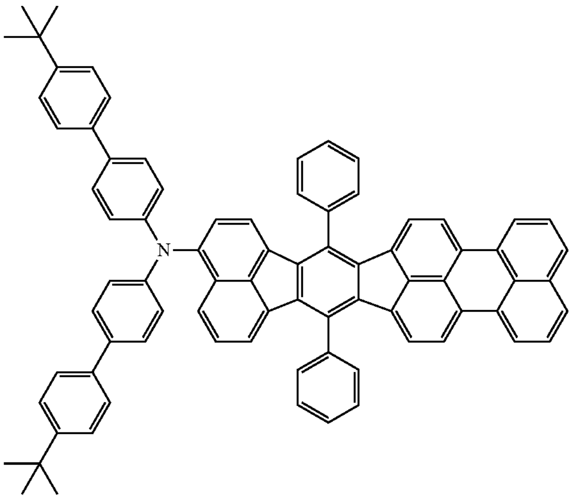
-continued
1-14
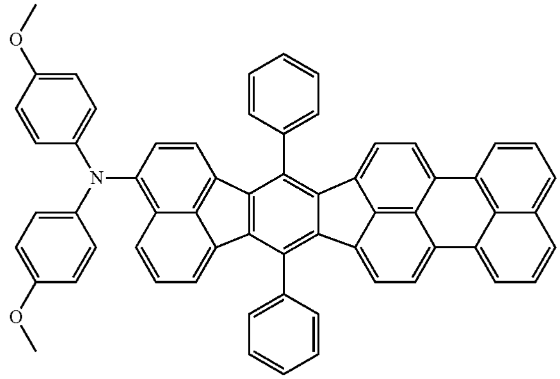
1-15
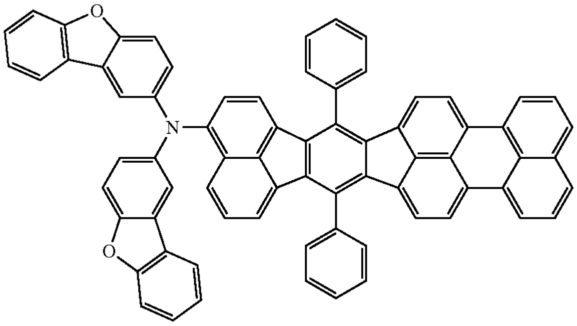
1-16
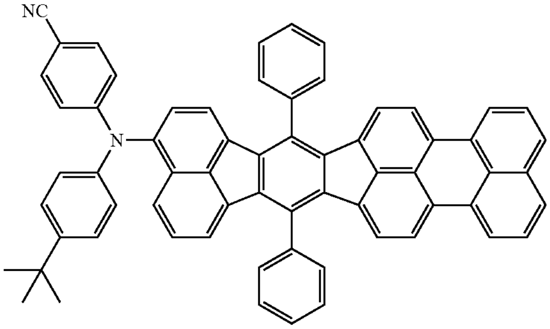
1-17
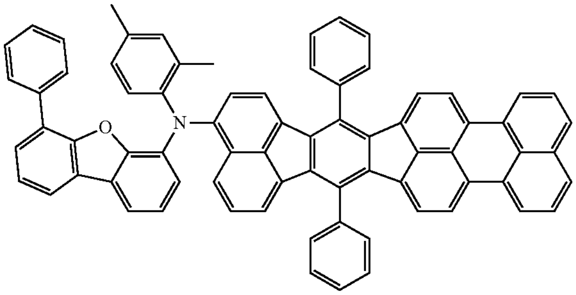

-continued
1-18
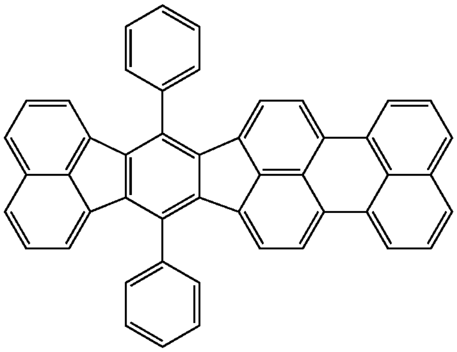
1-19
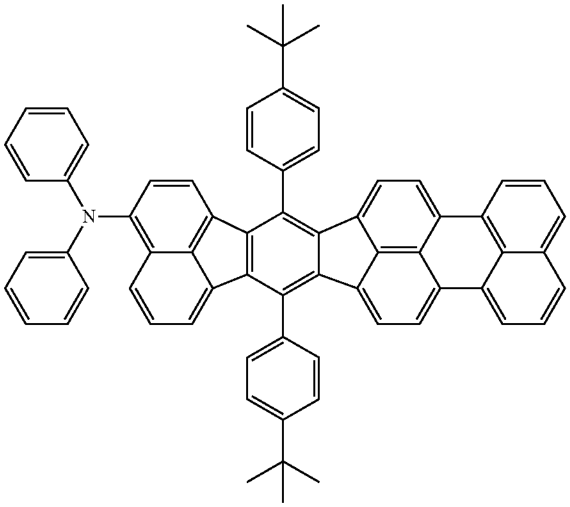
1-20
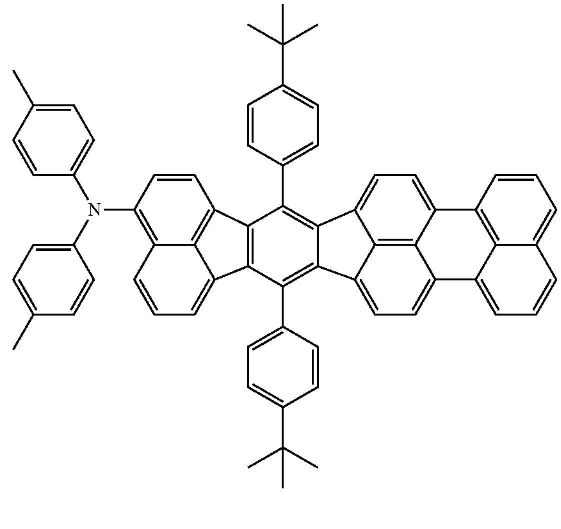
-continued
1-21
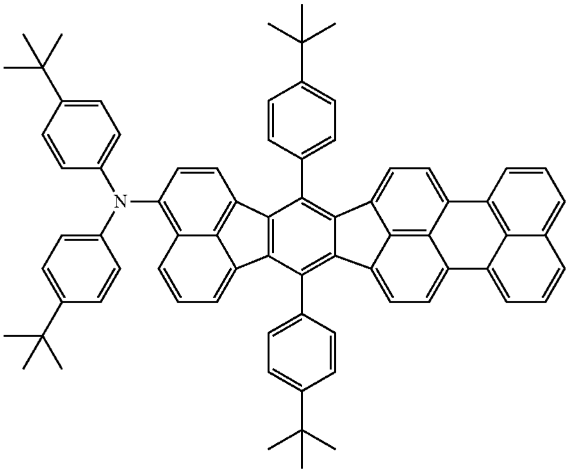
1-22
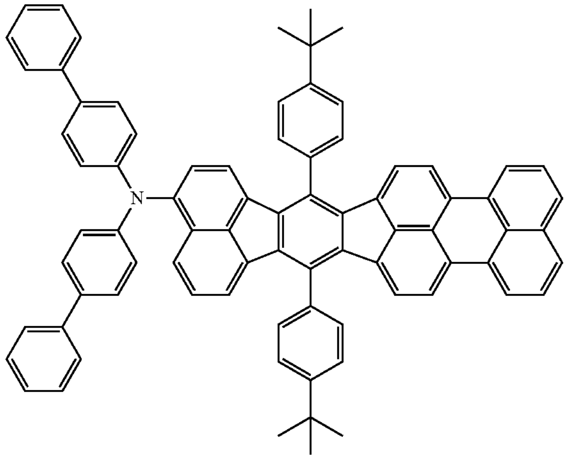
1-23
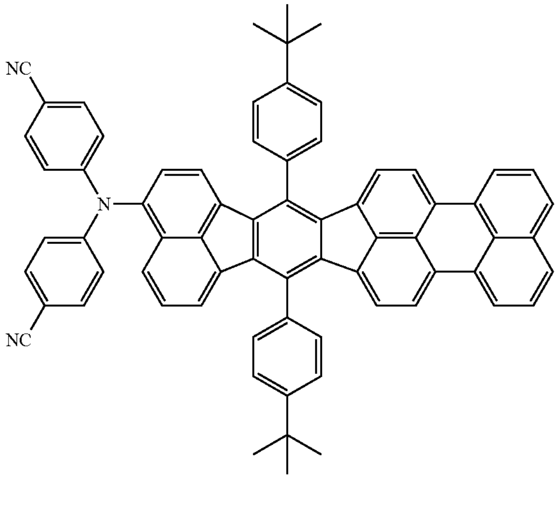

1-24
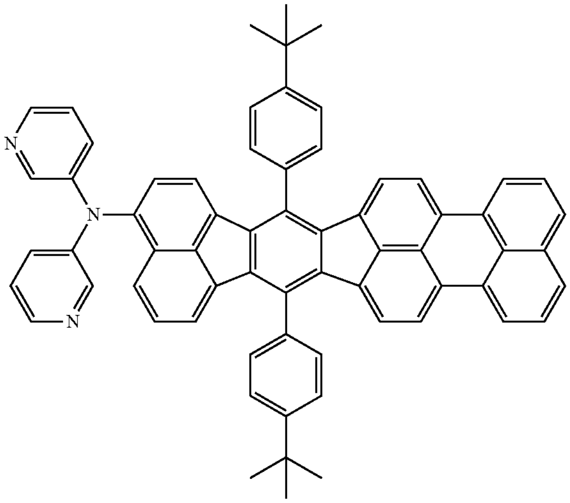
1-25
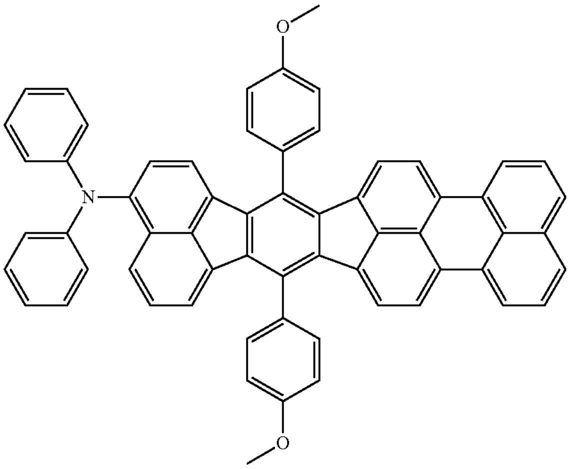
1-26
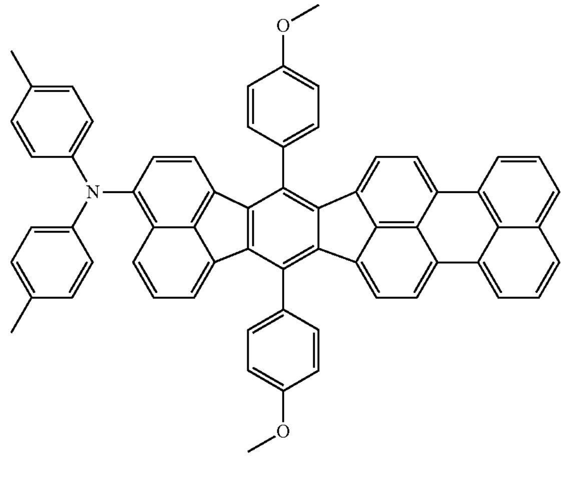
1-27
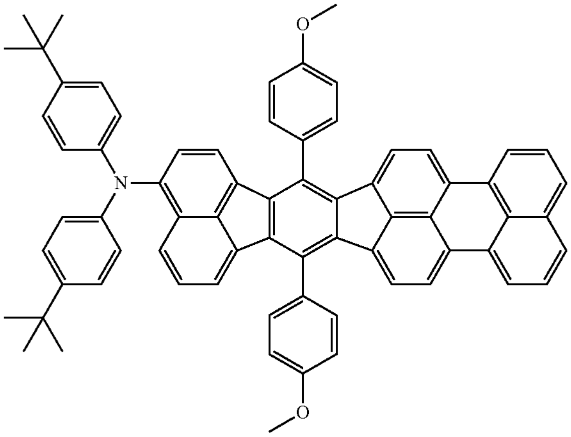
1-28
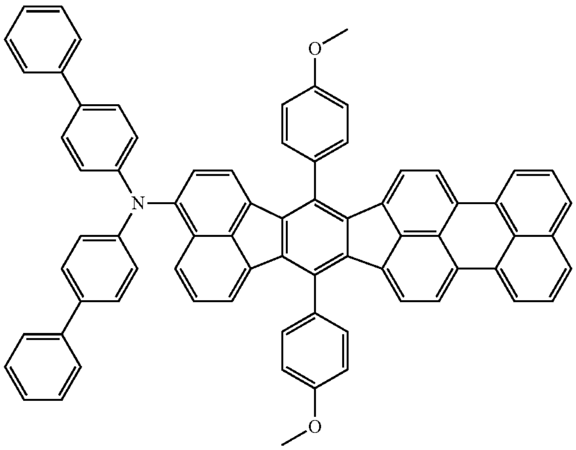
1-29
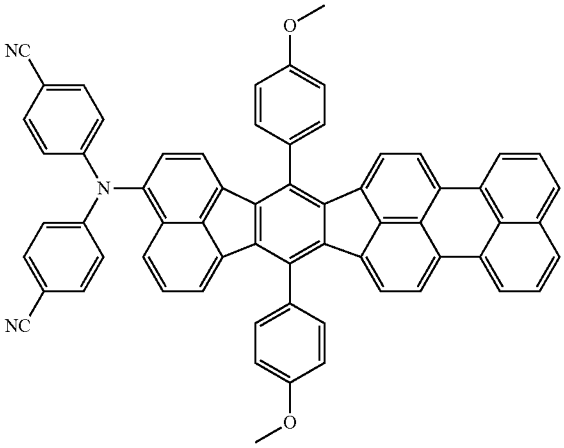

-continued 1-30

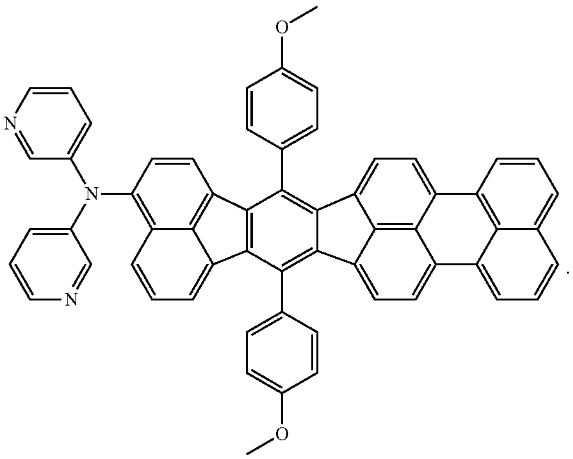

In another exemplary aspect, the organic compound having the structure of Chemical Formula 1 may comprise an organic compound in which the naphtho moiety of the core is unsubstituted or substituted with an aromatic or hetero aromatic amino group and the central benzene ring of the indaceno moiety is substituted with a hetero aromatic group. More particularly, the organic compound having the structure of Chemical Formula 1 may anyone having the following structure of Chemical Formula 5:

[Chemical Formula 5]

2-1

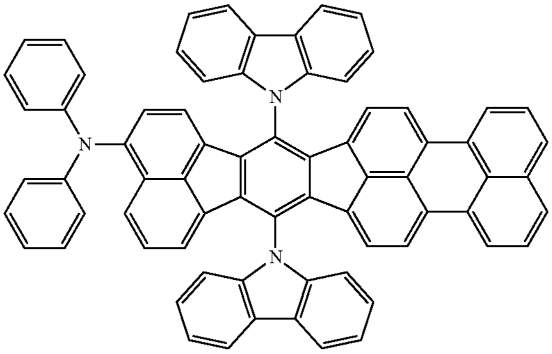

2-2

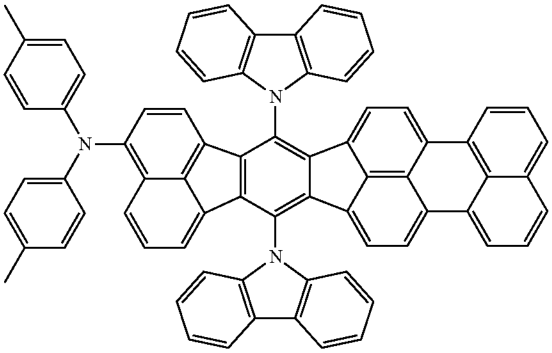

-continued 2-3

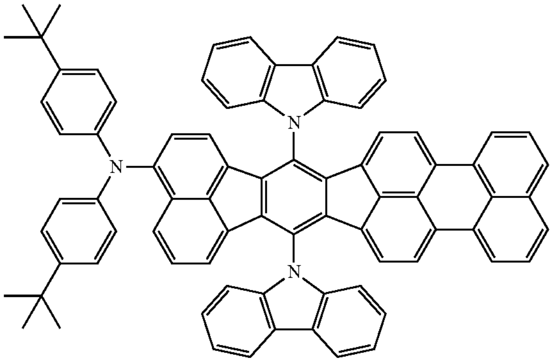

2-4

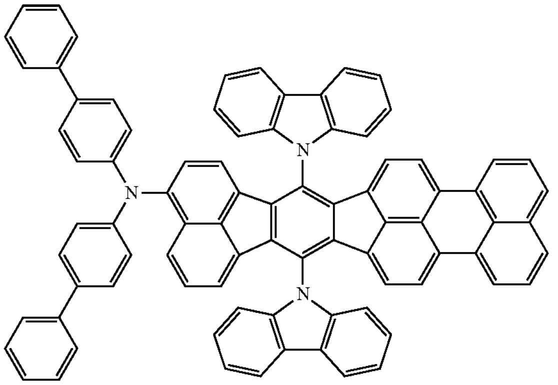

2-5

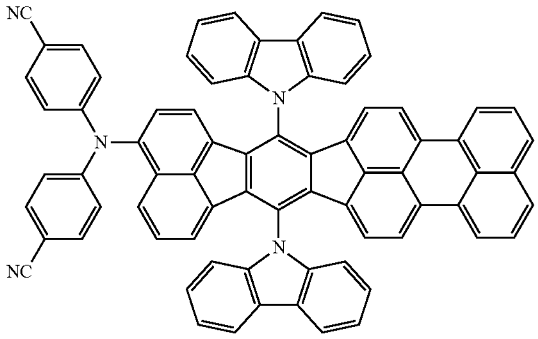

2-6

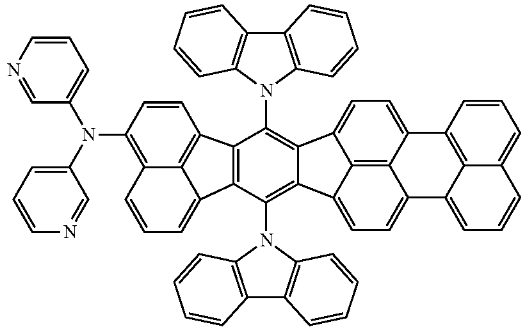

-continued 2-7

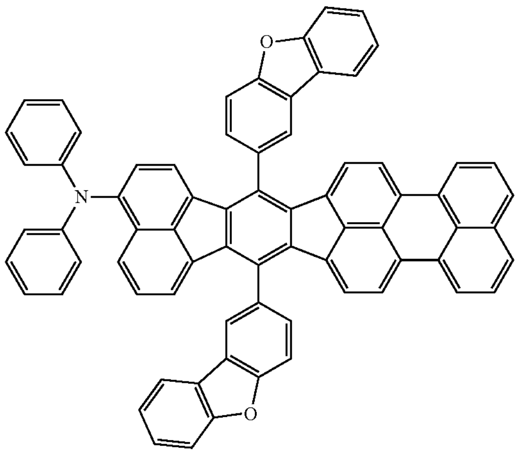

2-8

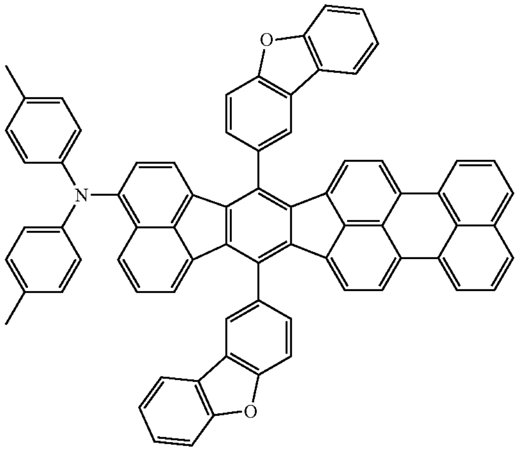

2-9

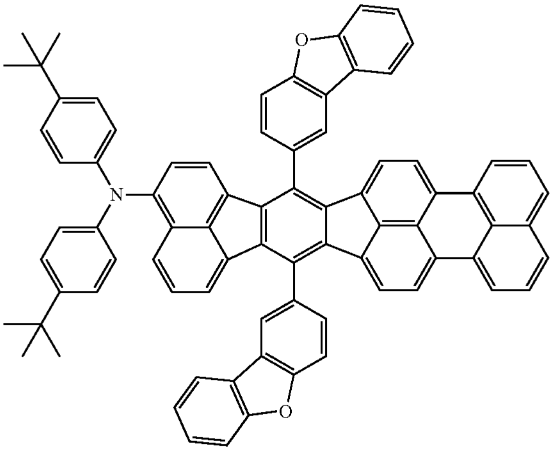

-continued 2-10

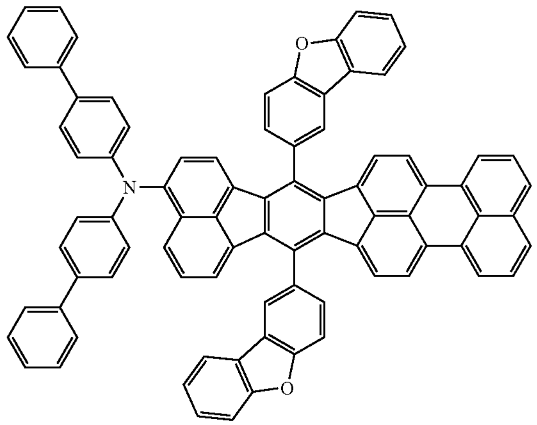

2-11

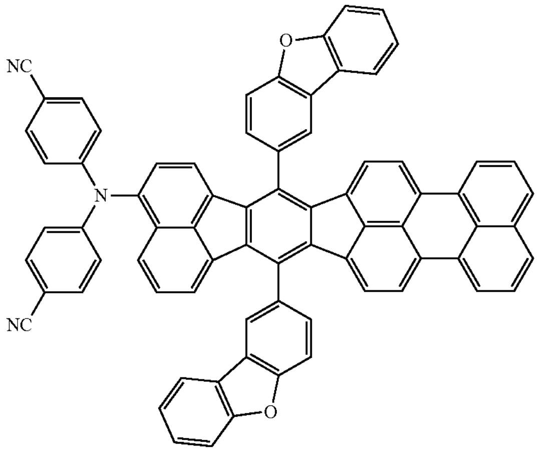

2-12

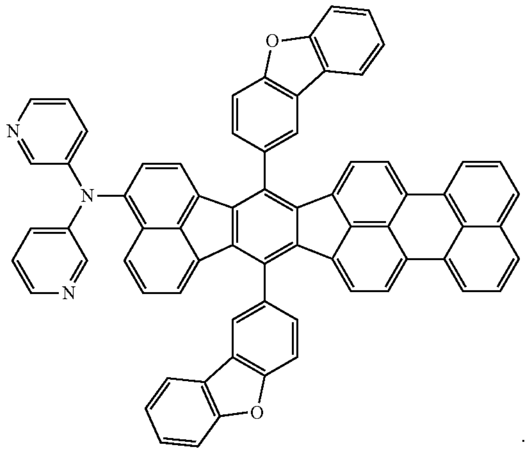

.

In still another exemplary aspect, the organic compound having the structure of Chemical Formula 1 may comprise an organic compound in which the naphtho moiety of the core is unsubstituted or substituted with an aromatic or hetero aromatic amino group, the central benzene ring of the indaceno moiety is substituted with an aromatic group and the perylene moiety is substituted with an aliphatic or aromatic group. More particularly, the organic compound having the structure of Chemical Formula 1 may anyone having the following structure of Chemical Formula 6:

[Chemical Formula 6]
3-1
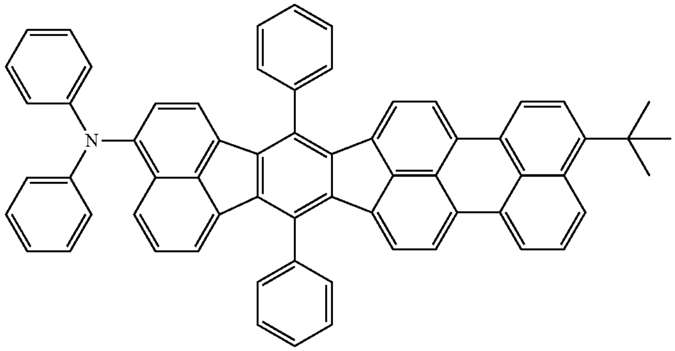
3-2
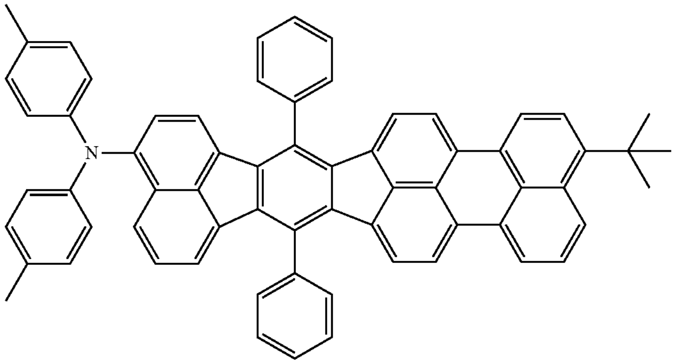
3-3
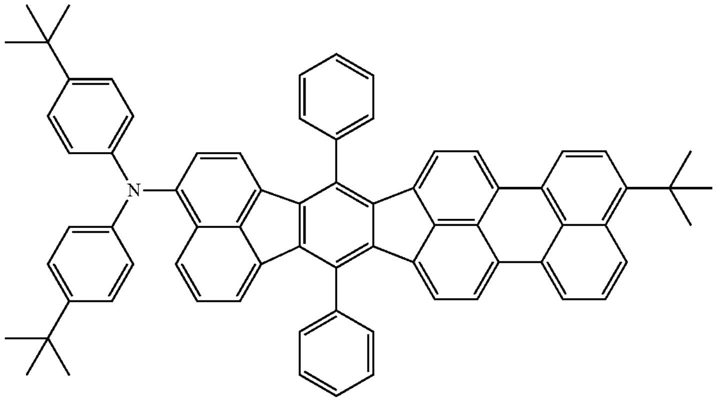
3-4
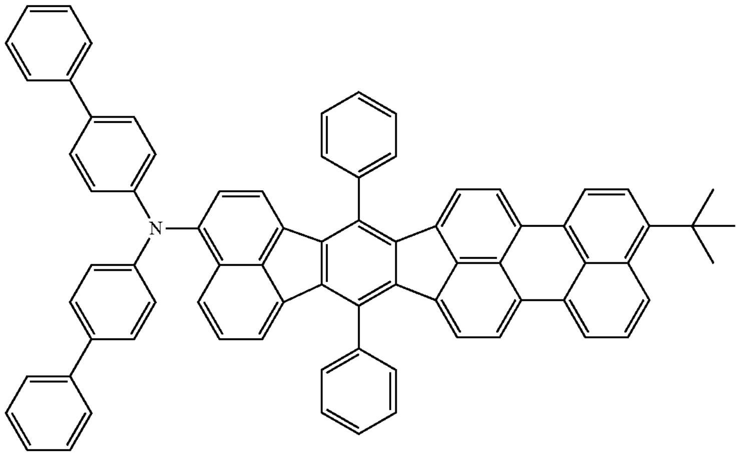

-continued
3-5
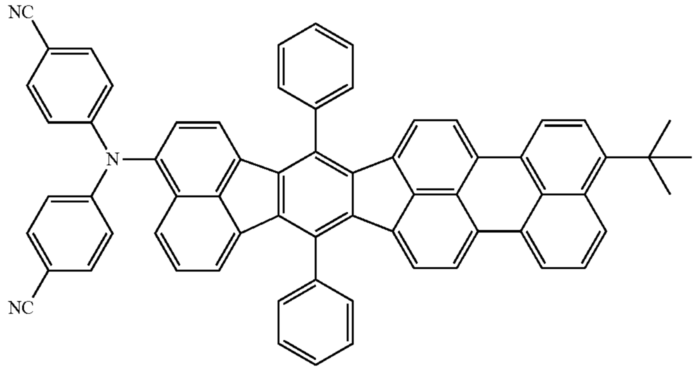
3-6
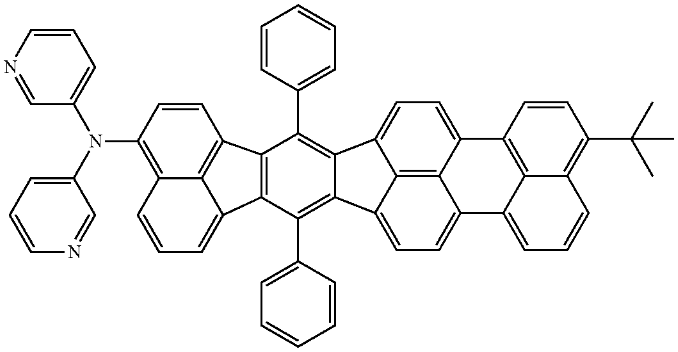
3-7
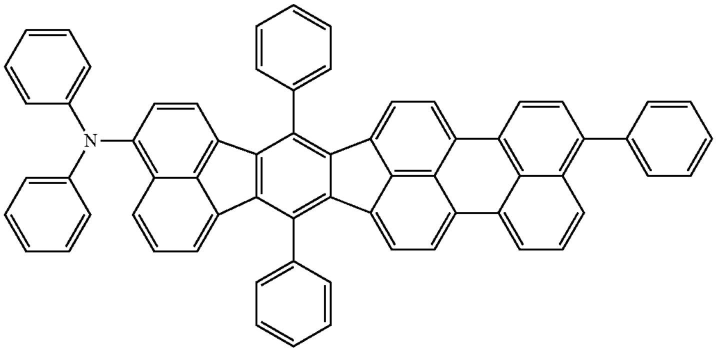
3-8
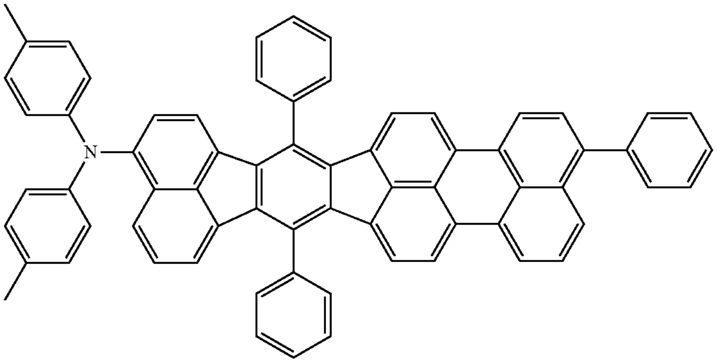

-continued
3-9
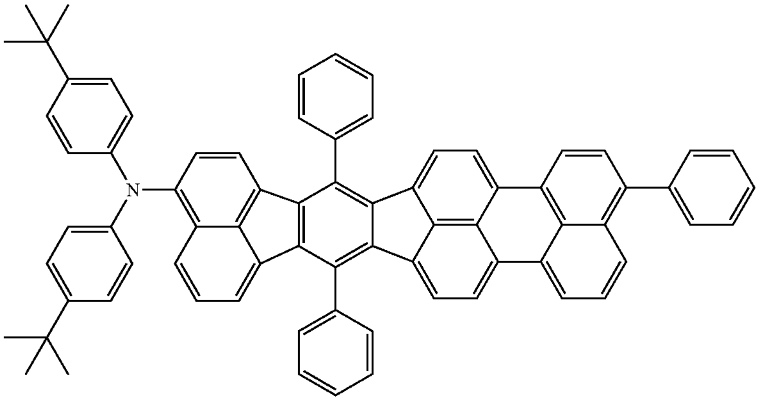
3-10
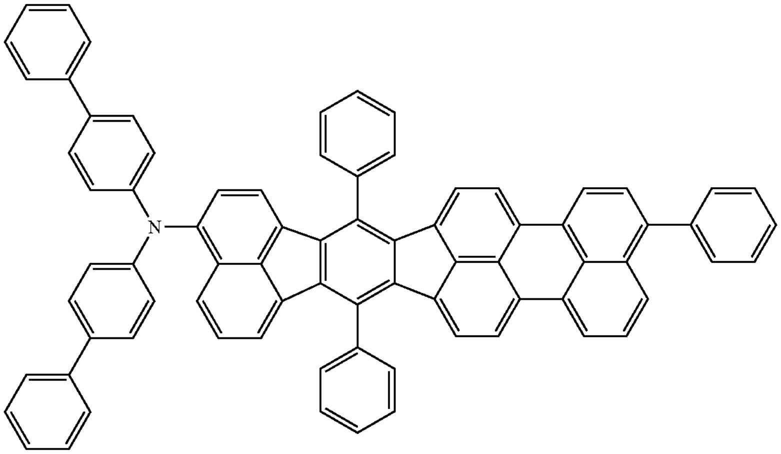
3-11
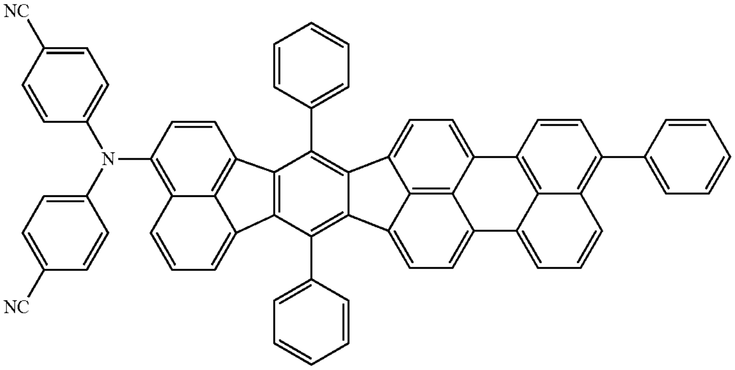
3-12
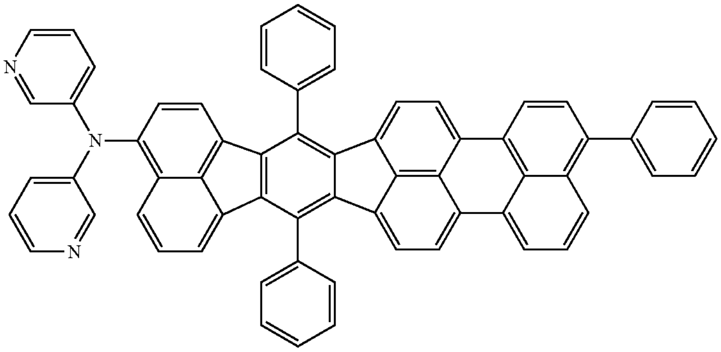
.

[Organic Light Emitting Device and OLED]

The organic compound having the structure of Chemical Formulae 1 to 6 may be applied into an EML of the OLED, so that it can lower the driving voltage, enhance the color purity and improve the luminous efficiency of the OLED. The OLED of the present disclosure may be applied to an organic light emitting device such as an organic light emitting display device or an organic light emitting illumination device. An organic light emitting display device including the OLED will be explained. FIG. 1 is a schematic cross-sectional view of an organic light emitting display device of the present disclosure.

As illustrated in FIG. 1, the organic light emitting display device 100 includes a substrate 110, a thin-film transistor Tr on the substrate 110, and an organic light emitting diode (OLED) D connected to the thin film transistor Tr.

The substrate 110 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 may be disposed over the substrate 110, and the thin film transistor Tr is disposed over the buffer layer 122. The buffer layer 122 may be omitted.

A semiconductor layer 120 is disposed over the buffer layer 122. In one exemplary aspect, the semiconductor layer 120 may include, but is not limited to, oxide semiconductor materials. In this case, a light-shield pattern may be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may include, but is not limited to, polycrystalline silicon. In this case, opposite edges of the semiconductor layer 120 may be doped with impurities.

A gate insulating layer 124 formed of an insulating material is disposed on the semiconductor layer 120. The gate insulating layer 124 may include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 may be patterned identically as the gate electrode 130.

An interlayer insulating layer 132 formed of an insulating material is disposed on the gate electrode 130 with covering over an entire surface of the substrate 110. The interlayer insulating layer 132 may include, but is not limited to, an inorganic insulating material such as silicon oxide ($SiO_x$) or silicon nitride ($SiN_x$), or an organic insulating material such as benzocyclobutene resin or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are also formed within the gate insulating layer 124 in FIG. 1. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line is, may be further formed in the pixel region of FIG. 1. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter may be formed separately in each pixel region. In this case, the organic light emitting display device 100 can implement full-color through the color filter.

For example, when the organic light emitting display device 100 is a bottom-emission type, the color filter may be disposed on the interlayer insulating layer 132 with corresponding to the OLED D. Alternatively, when the organic light emitting display device 100 is a top-emission type, the color filter may be disposed over the OLED D, that is, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it may be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 and a second electrode 230 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 may have a mono-layered structure of an emitting material layer (EML). Alternatively, the emissive layer 220 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 4, 7, 9 and 11). In one aspect, the emissive layer 220 may have one emitting unit. Alternatively, the emissive layer 220 may have multiple emitting units to form a tandem structure.

The emissive layer 220 comprises anyone having the structure of Chemical Formulae 1 to 6. As an example, the organic compound having the structure of Chemical Formulae 1 to 6 may be applied into a dopant in the EML, and in this case, the EML may further comprise a host and optionally other luminous materials.

The second electrode 230 is disposed over the substrate 110 above which the emissive layer 220 is disposed. The second electrode 230 may be disposed over a whole display area and may include a conductive material with a relatively low work function value compared to the first electrode 210. The second electrode 230 may be a cathode. For example, the second electrode 230 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 170 may be disposed over the second electrode 230 in order to prevent outer moisture from penetrating into the OLED D. The encapsulation film 170 may have, but is not limited to, a laminated structure of a first inorganic insulating film 172, an organic insulating film 174 and a second inorganic insulating film 176.

Moreover, a polarizer may be attached to the encapsulation film 170 in order to decrease external light reflection. For example, the polarizer may be a circular polarizer. In addition, a cover window may be attached to the encapsulation film 170 or the polarizer. In this case, the substrate 110 and the cover window may have a flexible property, thus the organic light emitting display device 100 may be a flexible display device.

As described above, anyone having the structure of Chemical Formulae 1 to 6 has a less spike-like structure compared to the conventional red fluorescent materials, thus there exist less overlapping regions among the adjacent molecules. Particularly, as the aromatic or hetero aromatic group is introduced into the organic compound, the compound has a bended conformation with increasing the distance inter-molecules. When the organic compound is used as the fluorescent material, triplet exciton energy, which cannot be utilized by the organic compound, is little transferred to the organic compound by Dexter energy transfer mechanism, but it is likely that the singlet exciton energy, which can participate in the luminescence process of the organic compound, is transferred to the organic compound by FRET mechanism. Accordingly, the OLED D1 can lower its driving voltage and improve its luminous efficiency by applying the organic compound. In addition, the OLED D1 can enhance its color purity by applying the organic compound substituted with a proper aromatic or hetero aromatic group.

Figure 2:
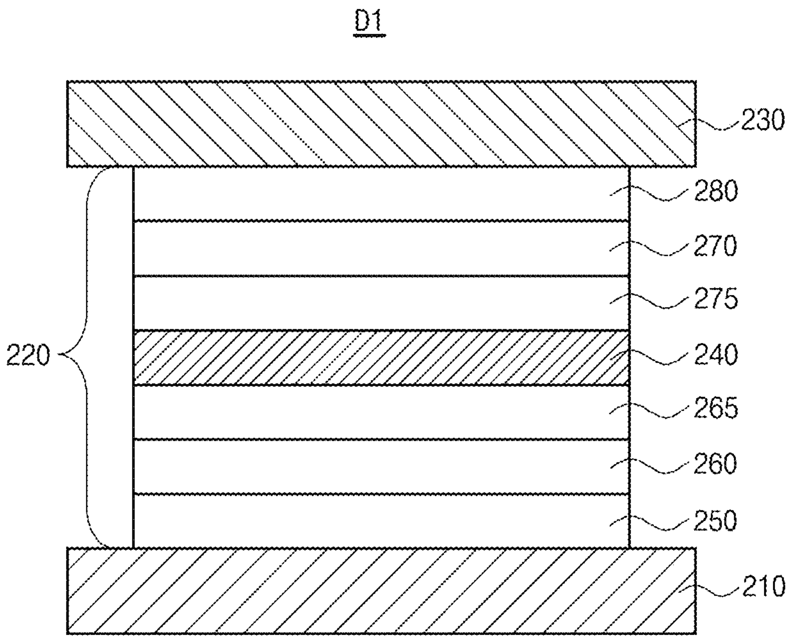
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 includes first and second electrodes 210 and 230 facing each other and an emissive layer 220 having single emitting unit disposed between the first and second electrodes 210 and 230. In one exemplary aspect, the emissive layer 220 comprises an EML 240 disposed between the first and second electrodes 210 and 230. Also, the emissive layer 220 further comprises a HIL 250 and a HTL 260 each of which is disposed sequentially between the first electrode 210 and the EML 240, and an ETL 270 and an EIL 280 each of which is disposed sequentially between the EML 240 and the second electrode 230.

Alternatively, the emissive layer 220 may further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 may be an anode that provides a hole into the EML 240. The first electrode 210 may include, but is not limited to, a conductive material having a relatively high work function value, for example, a transparent conductive oxide (TCO). In an exemplary aspect, the first electrode 210 may include, but is not limited to, ITO, IZO, ITZO, SnO, ZnO, ICO, AZO, and the like.

The second electrode 230 may be a cathode that provides an electron into the EML 240. The second electrode 230 may include, but is not limited to, a conductive material having a relatively low work function values, i.e., a highly reflective material such as Al, Mg, Ca, Ag, alloy thereof, combination thereof, and the like.

The HIL 250 is disposed between the first electrode 210 and the HTL 260 and improves an interface property between the inorganic first electrode 210 and the organic HTL 260. In one exemplary aspect, the HIL 250 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 250 may be omitted in compliance with a structure of the OLED D1.

The HTL 260 is disposed adjacently to the EML 240 between the first electrode 210 and the EML 240. In one exemplary aspect, the HTL 260 may include, but is not limited to, N,N'-Diphenyl-N,N'-bis(3-methylphenyl)-1,1'-biphenyl-4,4'-diamine (TPD), NPB, 4,4'-bis(N-carbazolyl)-

1,1'-biphenyl (CBP), Poly[N,N'-bis(4-butylphenyl)-N,N'-bis(phenyl)-benzidine](Poly-TPD), Poly[(9,9-dioctylfluorenyl-2,7-diyl)-co-(4,4'-(N-(4-sec-butylphenyl)diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In the first aspect, the EML 240 may comprise a first compound and a second compound. For example, the first compound may be a (first) host and the second compound may be a fluorescent material (first dopant). As an example, the organic compound having the structure of Chemical Formulae 1 to 6 may be used as the second compound. In this case the EML 240 may emit red light.

Figure 3:
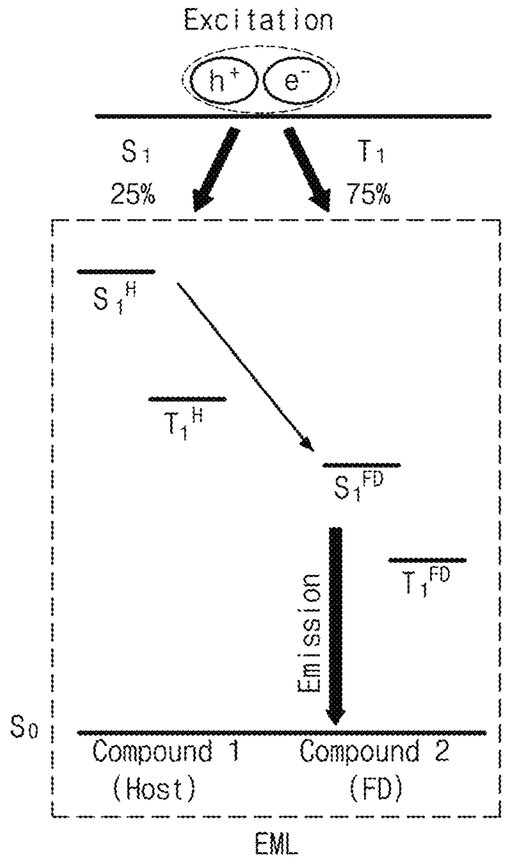
FIG. 3 is a schematic diagram illustrating luminous mechanism by energy level bandgap among luminous materials in accordance with an exemplary aspect of the present disclosure.

When the EML 240 comprises the first compound that may the host and the second compound which may be anyone having the structure of Chemical Formulae 1-6, it may be necessary to adjust excited singlet and triplet energy levels among the luminous materials. FIG. 3 is a schematic diagram illustrating luminous mechanism by energy level bandgap among luminous materials in accordance with this exemplary aspect of the present disclosure.

As illustrated in FIG. 3, an excited singlet energy level $S_1^H$ of the first compound, which may be the host, is higher than an excited singlet energy level $S_1^{FD}$ of the second compound FD, which may be the fluorescent material. Alternatively, an excited triplet energy level $T_1^H$ of the first compound may be higher than an excited triplet energy level $T_1^{FD}$ of the second compound. In this case, the exciton energy generated at the first compound may be transferred to the second compound. The first compound may have a luminescent spectrum overlapping widely to an absorption spectrum of the second compound, thus the exciton energy can be efficiently transferred from the first compound to the second compound.

As an example, the first compound may have, but is not limited to, maximum photoluminescence wavelength (PL $\lambda_{max}$) between about 500 nm and about 600 nm. The second compound that is anyone having the structure of Chemical Formulae 1 to 6 may have, but is not limited to, PL $\lambda_{max}$ between about 580 nm and about 650 nm, e.g. about 580 nm and about 620 nm. Also, the second compound may have, but is not limited to, maximum absorption wavelength (Abs. $\lambda_{max}$) between about 530 nm to about 590 nm, e.g. about 540 nm to about 580 nm. In this case, the Abs. $\lambda_{max}$ of the second compound may be substantially identical to or longer than the PL $\lambda_{max}$ of the first compound so that exciton energy can be efficiently transferred from the first compound to the second compound.

In one exemplary aspect, the first compound that can be used as the host in the EML 240 may comprise, but is not limited to, 9,9'-Diphenyl-9H,9'H-3,3'-bicarbazole (BCzPh), 1,3,5-Tris(carbazole-9-yl)benzene (TCP), TCTA, CBP, 4,4'-Bis(carbazole-9-yl)-2,2'-dimethylbipheyl (CDBP), 2,7-Bis(carbazole-9-yl)-9,9-dimethylfluorene (DMFL-CBP), 2,2',7,7'-Tetrakis(carbazole-9-yl)-9,9-spiorofluorene (spiro-CBP), Bis[2-(diphenylphosphino)phenyl]ether oxide (DPEPO), 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-Bis(carbazole-9-yl)-9-(2-ethyl-hexyl)-9H-carbazole (TCzl), 9-(3-(9H-carbazol-9-yl)phenyl)-9H-carbazole-3-carbonitrile (mCP-CN), 3,3'-bis(N-carbazolyl)-1,1'-biphenyl (mCBP), 1,3-Bis(carbazol-9-yl)benzene (mCP), 2,8-bis(diphenylphosphoryl)dibenzothiophene (PPT), 1,3,5-Tri[(3-pyridyl)-phen-3-yl]benzene (TmPyPB), 2,6-Di(9H-carbazol-9-yl)pyridine (PYD-2Cz), Bis(2-hydroxylphenyl)-pyridine)beryllium ($Bepp_2$), Bis(10-hydroxylbenzo[h] quinolinato)beryllium ($Bebg_2$), 1,3,5-Tris(1-pyrenyl)benzene (TPB3), 2,8-di(9H-carbazol-9-yl)dibenzothiophene (DCzDBT), 3',5'-Di(carbazol-9-yl)-[1,1'-bipheyl]-3,5-dicarbonitrile (DCzTPA), Diphenyl-4-triphenylsilylphenyl-phosphine oxide (TSPO1), 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

When the EML 240 comprise the first compound and the second compound, the contents of the second compound may be, but is not limited to, about 1 wt % to about 50 wt %, preferably about 1 wt % to about 30 wt %.

The ETL 270 and the EIL 280 may be disposed sequentially between the EML 240 and the second electrode 230. The ETL 270 includes a material having high electron mobility so as to provide electrons stably with the EML 240 by fast electron transportation.

In one exemplary aspect, the ETL 270 may comprise, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 may comprise, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,08)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ) and/or TSPO1.

The EIL 280 is disposed between the second electrode 230 and the ETL 270, and can improve physical properties of the second electrode 230 and therefore, can enhance the lifetime of the OLED D1. In one exemplary aspect, the EIL 280 may comprise, but is not limited to, an alkali halide such as LiF, CsF, NaF, $BaF_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 may have short lifetime and reduced luminous efficiency. In order to prevent these phenomena, the OLED D1 in accordance with this aspect of the present disclosure may have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 may comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB, 3,5-di(9H-carbazol-9-yl)-N,N-diphenylamine (DCDPA) and/or 2,8-bis(9-phenyl-9H-carbazol-3-yl)dibenzo[b,d]thiophene.

In addition, the OLED D1 may further include the HBL 275 as a second exciton blocking layer between the EML 240 and the ETL 270 so that holes cannot be transferred from the EML 240 to the ETL 270. In one exemplary aspect, the HBL 275 may comprise, but is not limited to, oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 may comprise a compound having a relatively low HOMO energy level compared to the luminescent materials in EML 240. The HBL 275 may comprise, but is not limited to, mCBP, BCP, BAlq, $Alq_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole and combination thereof.

In accordance with this aspect, the EML 240 comprises the first compound and the second compound FD that is any organic compound having the structure of Chemical Formulae 1 to 6. The organic compound has a less spike-like structure compared to the conventional red fluorescent materials, thus there exist less overlapping regions among the adjacent molecules and may have a bended conformation by applying proper substituent. Accordingly, since the triplet energy transfer by Dexter energy transfer mechanism is limited, but the single exciton energy is mainly transferred from the first compound to the second compound via FRET mechanism. In other words, as Dexter energy transfer mechanism which triplet exciton energy transfers as a non-radiative recombination is minimized, it is likely that the singlet exciton energy contributing emission is transferred to the second compound. Accordingly, the OLED D2 which applies the organic compound into the EML 240 can be driven at low voltage and improve its luminous efficiency and color purity.

Figure 4:
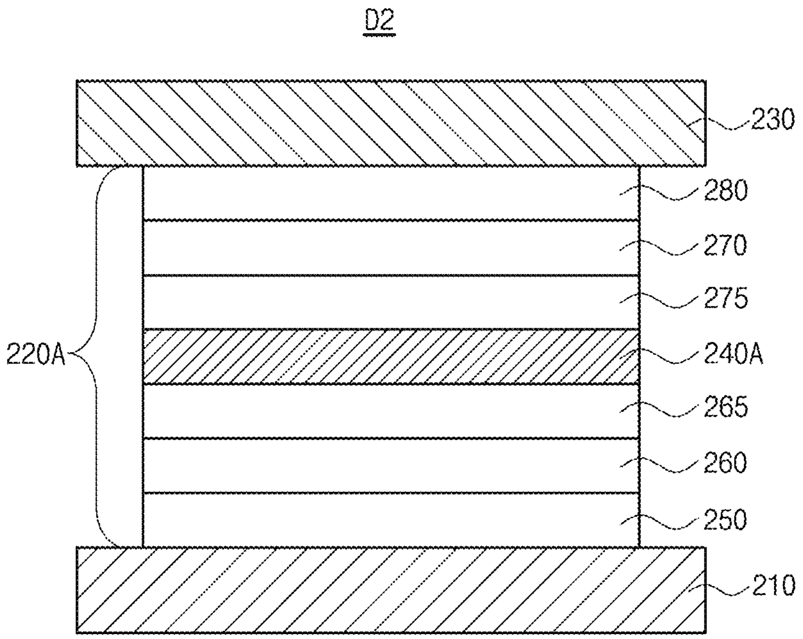
FIG. 4 is a schematic cross-sectional view illustrating an OLED in accordance with another exemplary aspect of the present disclosure.

In the above aspect, the EML consists of the first compound that may be the host and the second compound that may the fluorescent material or dopant. Unlike that aspect, the EML may comprise plural dopants having different luminous properties. FIG. 4 is a schematic cross-sectional view illustrating an OLED in accordance with another exemplary aspect of the present disclosure. As illustrated in FIG. 4, the OLED D2 comprises the first electrode 210, the second electrode 230 facing the first electrode 210 and an emissive layer 220A disposed between the first and second electrodes 210 and 230. The emissive layer 220A having single emitting unit comprises an EML 240A. Also, the emissive layer 220A comprise the HIL 250 and the HTL 260 each of which is disposed sequentially between the first electrode 210 and the EML 240A, and the ETL 270 and the EIL 280 each of which is disposed sequentially between the EML 240A and the second electrode 230. Alternatively, the emissive layer 220A may further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

In this aspect, the EML 240A comprise the first compound, the second compound and a third compound. The first compound may be the host, the second compound may be the fluorescent material (second dopant) and the third compound may be delayed fluorescent material (first dopant). The second compound may comprise any organic compound having the structure of Chemical Formulae 1 to 6. When the EML 240A comprises the delayed fluorescent material, it is possible to realize OLED D2 having much enhanced luminous efficiency by adjusting energy levels among the host and the dopants.

An external quantum efficiency (EQE, $\eta_{ext}$) of the luminous material in an EML can be calculated according to the following Equation:

$$\eta_{ext}=\eta_{S/T}\times\Gamma\times\Phi\times\eta_{out\text{-}coupling}$$

wherein $\eta_{S/T}$ is a singlet/triplet ratio; $\Gamma$ is a charge balance factor; $\Phi$ is a radiative efficiency; and $\eta_{out\text{-}coupling}$ is an out-coupling efficiency.

When holes and electrons meet to form exciton, singlet exciton with a paired spin state and triplet exciton with an unpaired spin state is generated in a ratio of 1:3 in theory. Since only the singlet exciton participates in luminescence and the remaining 75% triplet excitons cannot participate in luminescence in the fluorescent material, the singlet/triplet ratio is 0.25 in the conventional fluorescent material.

The charge balance factor $\Gamma$ indicates a balance of holes and electrons forming excitons and generally has "1" assuming 100% 1:1 matching. The radiative efficiency $\Phi$ is a value involved in luminous efficiency of the substantial luminous materials and depends upon the photoluminescence of the dopant in the host-dopant system. The out-coupling efficiency is a ratio of extracted externally light among the emitted light form the luminous material. When a thin film is used by depositing the luminous material with isotropic type, each luminous molecule is existed randomly without any specific orientation. The out-coupling efficiency in such random orientation is assumed "0.2". Therefore, when taking all four factors defined in the above Equation into account, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. However, blue phosphorescent materials have too low color purity and too short lifetime to be applied into commercial display devices. Thus, it is necessary to improve the disadvantages of the phosphorescent materials and the low luminous efficiency of the blue luminescent materials.

Recently, a delayed fluorescent material, which can solve the problems accompanied by the conventional art fluorescent and/or phosphorescent materials, has been developed. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the singlet energy and the triplet energy during the luminescent process, unlike the conventional fluorescent materials.

Figure 5:
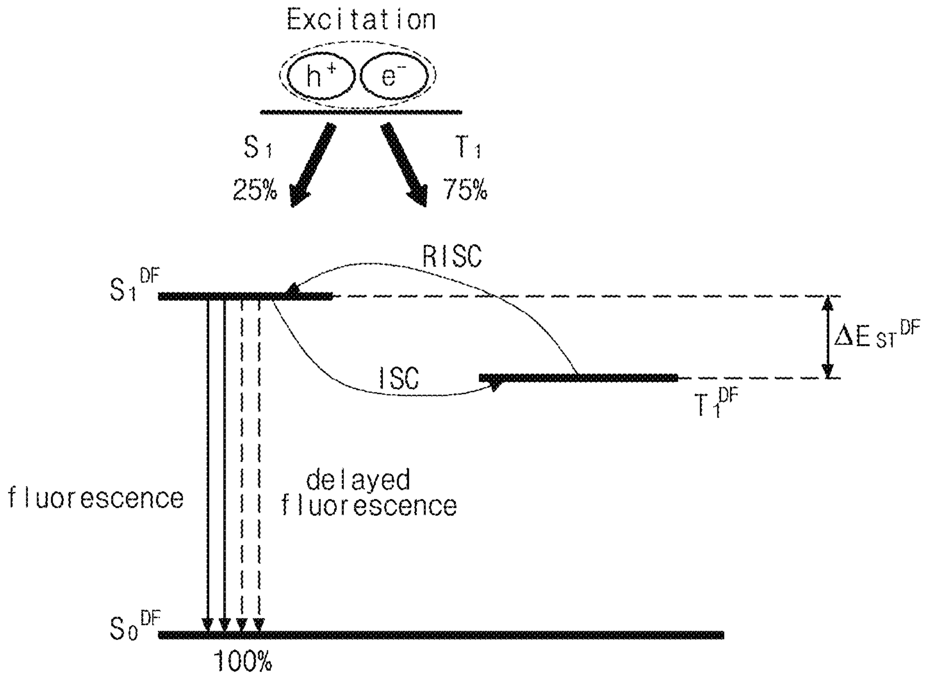
FIG. 5 is a schematic diagram illustrating a luminous mechanism of a delayed fluorescent material.

The luminous mechanism of the delayed fluorescent material will be explained with referring to FIG. 5, which is a schematic diagram illustrating a luminous mechanism of delayed fluorescent material in the EML. As illustrated in FIG. 5, the excitons of singlet energy level $S_1^{DF}$ as well as the excitons of triplet energy level $T_1^{DF}$ in the delayed fluorescent material DF can be transferred to an intermediate energy level state, i.e. ICT state, and then the intermediate stated excitons can be shifted to a ground state ($S_0^{DF}$; $S_1^{DF}$→ICT←$T_1^{DF}$). Since the excitons of singlet energy level $S_1^{DF}$ as well as the excitons of triplet energy level $T_1^{DF}$ in the delayed fluorescent material DF is involved in the luminescent process, the delayed fluorescent material DF can improve its luminous efficiency.

Since both the HOMO and the LUMO are widely distributed over the whole molecule within the common fluorescent material, it is not possible to inter-convert exciton energies between the singlet energy level and the triplet energy level within the common fluorescent material (selection rule). In contrast, since the delayed fluorescent material DF, which can be converted to ICT state, has little orbital overlaps between HOMO and LUMO, there is little interaction between the HOMO state and the LUMO state. As a result, the changes of spin states of electrons do not have an influence on other electrons, and a new charge transfer band (CT band) that does not follow the selection rule is formed within the delayed fluorescent material.

In other words, since the delayed fluorescent material DF has the electron acceptor moiety spacing apart from the electron donor moiety within the molecule, it exists as a polarized state having a large dipole moment within the molecule. As the interaction between HOMO and LUMO becomes little in the state where the dipole moment is polarized, the triplet excitons as well as the singlet excitons can be converted to ICT state. In other words, ICT complex can be excited to a CT state in which singlet exciton and triplet exciton can be exchanged mutually, thus the triplet excitons as well as singlet excitons can be involved in the luminescent process. In case of driving an OLED that includes the delayed fluorescent material DF, both 25% singlet excitons and 75% triplet excitons are converted to ICT state by heat or electrical field, and then the converted excitons drops to the ground state $S_0$ with luminescence. Therefore, the delayed fluorescent material DF may have 100% internal quantum efficiency in theory.

The delayed fluorescent material DF must has an energy level bandgap $\Delta E_{ST}^{DF}$ equal to or less than about 0.3 eV, for example, from about 0.05 to about 0.3 eV, between the excited singlet energy level $S_1^{DF}$ and the excited triplet energy level $T_1^{DF}$ so that exciton energy in both the excited singlet energy level $S_1^{DF}$ and the excited triplet energy level $T_1^{DF}$ can be transferred to the ICT state. The material having little energy level bandgap between the singlet energy level $S_1^{DF}$ and the triplet energy level $T_1^{DF}$ can exhibit common fluorescence with Inter system Crossing (ISC) in which the excitons of singlet energy level $S_1^{DF}$ can be transferred to the excitons of triplet energy level $T_1^{DF}$, as well as delayed fluorescence with Reverser Inter System Crossing (RISC) in which the excitons of triplet energy level $T_1^{DF}$ can be transferred upwardly to the excitons of singlet energy level $S_1^{DF}$, and then the exciton of singlet energy level $S_1^{DF}$ transferred from the triplet energy level $T_1^{DF}$ can be transferred to the ground state $S_0^{DF}$.

As described above, the thermally-delayed fluorescent material should reduce the overlap between HOMO and LUMO and have electron acceptor spacing apart from electron donor so as to minimize the energy bandgap $\Delta E_{ST}^{DF}$ between the excited singlet energy level $S_1^{DF}$ and the excited triplet energy level $T_1^{DF}$. Since the molecular conformation of the excited state and the ground state is twisted in the molecules having less overlaps between the HOMO and the LUMO and spaced apart electron donor-electron acceptor, the delayed fluorescent material has short luminous lifetime and addition charge transfer transition (CT transition) is caused in the delayed fluorescent material. Due to the luminous property caused by the CT luminous mechanism, the delayed fluorescent material has luminous wavelength with wide FWHM (full width at half maximum, and thus shows deteriorated color purity.

However, the triplet exciton of the delayed fluorescent material is converted to its own singlet exciton and then the converted singlet exciton of the delayed fluorescent material is transferred to the fluorescent material in hyper fluorescence, thus increases the singlet exciton generation ratio of the fluorescent materials which utilizes only the singlet exciton. As described above, since the delayed fluorescent material utilized both the singlet exciton energy and the triplet exciton energy, the fluorescent material absorbs the singlet and triplet exciton energies emitted from the delayed fluorescent material, and the fluorescent material generate 100% singlet exciton utilizing the absorbed exciton energies in luminescence process, so the luminous efficiency of the fluorescent material can be improved. As an example, as the ultimate light emission occurs at the fluorescent material, color purity can be enhanced in case of using the fluorescent material with relatively narrow FWHM. In addition, since the luminous lifetime is determined by the fluorescent material, the EML having both the delayed fluorescent material and the fluorescent material can improve its luminous lifetime and stability compared to the EML having only the delayed fluorescent material.

Figure 6:
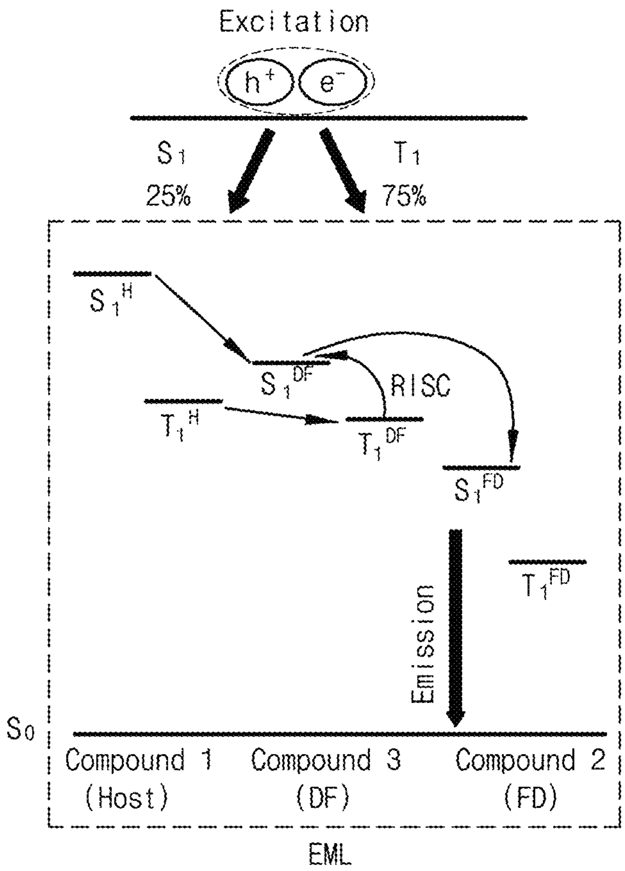
FIG. 6 is a schematic diagram illustrating luminous mechanism by energy level bandgap among luminous materials in accordance with another exemplary aspect of the present disclosure.

As described above, the EML 240A comprise the first compound that may be the host, the second compound FD that may be the fluorescent material and may be anyone having the structure of Chemical Formulae 1 to 6, and the third compound that may be the delayed fluorescent material DF. In this case, it is necessary to adjust energy levels among the luminous materials in order to transfer exciton energy among the first to third compounds. FIG. 6 is a schematic diagram illustrating luminous mechanism by energy level bandgap among luminous materials in accordance with another exemplary aspect of the present disclosure.

As illustrated in FIG. 6, the exciton energy generated at the first compound should be transferred primarily to the third compound that may the delayed fluorescent material DF. To this end, each of the excited singlet energy level $S_1^{H}$ and the excited triplet energy level $T_1^{H}$ of the first compound, which can be the host in the EML 240, is higher than each of the excited singlet energy level $S_1^{DF}$ and the excited triplet energy level $T_1^{DF}$ of the third compound having the delayed fluorescent property, respectively.

For example, when the excited triplet energy level $T_1^{H}$ of the first compound is not high enough than the excited triplet energy level $T_1^{DF}$ of the third compound DF, the triplet state exciton energy of the third compound DF may be reversely transferred to the excited triplet energy level $T_1^{H}$ of the first compound. In this case, the triplet exciton reversely transferred to the first compound where the triplet exciton cannot be emitted is quenched as non-emission so that the triplet exciton energy of the third compound DF having the delayed fluorescent property cannot contribute to luminescence. As an example, the excited triplet energy level $T_1^{H}$ of the first compound may be higher than the excited triplet energy level $T_1^{DF}$ of the third compound DF by at least about 0.5 eV, e.g. at least about 0.2 eV.

The third compound DF having the delayed fluorescent property may have the energy level bandgap $\Delta E_{ST}^{DF}$ between the excited singlet energy level $S_1^{DF}$ and the excited triplet energy level $T_1^{DF}$ equal to or less than about 0.3 eV, for example between about 0.05 eV and about 0.3 eV (see, FIG. 5). On the contrary, each of the energy level bandgap between the excited singlet energy level $S_1^{H}$ and the excited triplet energy level $T_1^{H}$ of the first compound, that may be the host, and the energy level bandgap between the excited singlet energy level $S_1^{FD}$ and the excited triplet energy level $T_1^{FD}$ of the second compound, that may be the fluorescent material, may be more than about 0.3 eV, respectively.

When the energy level bandgap between the singlet energy level and the triplet energy level of the first and second compounds is more than about 0.3 eV, the OLED D2 may have short luminous lifetime owing to RISC mechanism and ISC mechanism caused by those compounds. For example, each of the energy level bandgap between the excited singlet energy level $S_1^{H}$ and the excited triplet energy level $T_1^{H}$ of the first compound and the energy level bandgap between the excited singlet energy level $S_1^{FD}$ and the excited triplet energy level $T_1^{FD}$ of the second compound may be, but is not limited to, more than 0.3 eV and less than or equal to about 1.5 eV.

In addition, it is necessary to adjust properly HOMO energy levels and LUMO energy levels of the first compound and the third compound. For example, it is preferable that an energy level bandgap ($|HOMO^{H}-HOMO^{DF}|$) between the HOMO energy level ($HOMO^{H}$) of the first compound and the HOMO energy level ($HOMO^{DF}$) of the third compound, or an energy level bandgap ($|LUMO^{H}-LUMO^{DF}|$) between the LUMO energy level ($LUMO^{H}$) of the first compound and the LUMO energy level ($LUMO^{DF}$) of the third compound may be equal to or less than about 0.5 eV, for example, between about 0.1 eV to about 0.5 eV. In this case, the charges can be transported efficiently from the first compound as the host to the third compound as the delayed fluorescent material and thereby enhancing the ultimate luminous efficiency in the EML 240A.

In addition, it is necessary for the EML 240A to implement high luminous efficiency and color purity as well as to transfer exciton energy efficiently from the third compound, which is converted to ICT complex state by RISC mechanism in the EML 240A, to the second compound which is the fluorescent material in the EML 240A. To this end, the excited triplet energy level $T_1^{DF}$ of the third compound is higher than the excited triplet energy level $T_1^{FD}$ of the second compound. Optionally, the excited singlet energy level $S_1^{DF}$ of the third compound may be higher than the excited singlet energy level $S_1^{FD}$ of the second compound.

In the hyper fluorescence mechanism comprising the ultimately emitted fluorescent material, it is important to transfer exciton energy from the delayed fluorescent material to the fluorescent material in order to improve its luminous efficiency. The most important factor determining the exciton energy transfer efficiency between the delayed fluorescent material and the fluorescent material is overlapping area between the photoluminescence spectrum of the delayed fluorescent material and the absorption spectrum of the fluorescent material receiving the exciton energy.

In one exemplar aspect, the second compound which may be anyone having the structure of Chemical Formulae 1 to 6 may have, but is not limited to, PL $\lambda_{max}$ between about 580 nm and about 650 nm, e.g. about 580 nm and about 620 nm. In addition, the second compound may have Abs. $\lambda_{max}$ that is substantially identical to or longer than the PL $\lambda_{max}$ of the third compound having the delayed fluorescent property so that the exciton energy can be efficiently transferred from the third compound to the second compound. As an example, the second compound may have, but is not limited to, Abs. $\lambda_{max}$ between about 530 nm to about 590 nm, e.g. about 540 nm to about 580 nm. The third compound may have, but is not limited to, PL $\lambda_{max}$ between about 520 nm and about 610 nm.

In this case, the overlapping regions between the absorption wavelength spectrums of the second compound that may be anyone having the structure of Chemical Formulae 1 to 6 and the photoluminescence wavelength spectrums of the third compound that may be the delayed fluorescent material are increased. As the exciton energy efficiency form the third compound to the second compound improves, the luminous efficiency of the OLED D2 can be increased. Also, as the second compound, not the third compound using CT luminescent mechanism, emits light while the exciton is shifted from the excited state to the ground state, the OLED D2 can improve its color purity.

As described above, any organic compound having the structure of Chemical Formulae 1 to 6 has a less spike-like structure compared to the conventional red fluorescent materials, thus there exist less overlapping regions among the adjacent molecules. When the organic compound has a bended conformation by applying an aromatic or hetero aromatic group, the distance among adjacently disposed molecules are increased significantly. When the second compound that may be any organic compound having the structure of Chemical Formulae 1 to 6 is introduced in the EML 240A, the triplet exciton energy transfer between the third compound, which may be the delayed fluorescent material, the second compound through Dexter energy transfer mechanism is minimized, while the singlet exciton energy of the third compound is transferred mainly to the second compound through FRET mechanism. The triplet exciton energy, which cannot be utilized by the second compound, is little transferred to the second compound through Dexter mechanism, but the singlet exciton energy, which can be utilized by the second compound, is mainly transferred to the second compound. Accordingly, triplet exciton energy loss as a non-radiative recombination can be minimized. Therefore, the OLED D2 where the second compound that may be any organic compound having the structure of Chemical Formulae 1 to 6 can lower its driving voltage and improve its luminous efficiency and color purity to implement hyper fluorescence.

According to this aspect, the EML 240A comprises any organic compound having the structure of Chemical Formulae 1 to 6 as the fluorescent material in order to prevent the color purity from being deteriorated when an EML comprises the third compound having the delayed fluorescent property. The triplet exciton energy of the third compound is converted upwardly to its own singlet exciton energy by RISC, the converted singlet exciton energy of the third compound is transferred to the second compound having fluorescent property in the same layer via FRET mechanism, and thus exciton energy loss can be minimized.

In one exemplary aspect, when the EML 240A comprises the first compound as the host, the second compound having the fluorescent property and the third compound having the delayed fluorescent property, the contents of the first compound may be larger than each of the contents of the second and third compounds. Also, the contents of the third compound may be larger than the contents of the second compound. As an example, the contents of the first compound may be larger than the contents of the third compound, and the contents of the third compound may be larger than the contents of the second compound.

In this case, the exciton energy can be transferred sufficiently from the third compound to the second compound. When the EML 240A comprises the first to third compounds, each contents of the second and third compounds may be about 1 wt % to about 50 wt %. For example, the contents of the third compound in the EML 240A may be about 10 wt % to 50 wt %, preferably about 10 wt % to about 40 wt %, and the contents of the second compound in the EML 240A may be about 1 wt % to about 10 wt %.

The first compound in the EML 240A may comprise, but is not limited to, BCzPh, TCP, TCTA, CBP, CDBP, DMFL-CBP, spiro-CBP, DPEPO, PCzB-2CN, mCzB-2CN, TCzl, mCP-CN, mCBP, mCP, PPT, TmPyPB, PYD-2Cz, $Bepp_2$, $Bebg_2$, TPB3, DCzDBT, DCzTPA, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicarbazole.

In one aspect, the third compound may comprise a green or yellow-green emitting delayed fluorescent material having the PL $\lambda_{max}$ between about 520 nm and about 580 nm. For example, the green or yellow-green delayed fluorescent material may comprise, but is not limited to, 6,11-di(10H-phenoxazin-10-yl)dibenzo[f,h]quinoxaline (ATP-PXZ), 7,10-di(10H-phenoxazin-10-yl)dibenzo[f,h]quinoxaline (m-ATP-PXZ), 2,3,5,6-tetra(9H-carbazol-9-yl)isonicotinonitrile (4CzCNPy), 10-(4-(4,6-Diphenyl-1,3,5-triazin-2-yl) phenyl)-10H-phenoxazine (PXZ-TRZ), 10,10'-((6-Phenyl-1,3,5-triazine-2,4-diyl)bis(4,1-phenylene))bis(10H-phenoxazine (bis-PXZ-TRZ), 2,4,6-tris(4-(10H-phenoxazin-10-yl)phenyl)-1,3,5-triazine (tri-PXZ-TRZ), 5-(4-(4,5-diphenyl-4H-1,2,4-triazol-3-yl)phenyl)-10-phenyl-5,10-dihydrophenazine (PPZ-3TPT), 2,6-bis(4-(10H-phenoxazin-10-yl)phenyl)benzo[1,2-d:4,5-d_]bis(thiazole) (BT2), 5,10-bis(4-(1-phenyl-1H-benzo[d]imidazol-2-yl) phenyl)-5,10-dihydrophenazine (DHPZ-2BI), 4,4'-(phenazine-5,10-diyl)dibenzonitrile (DHPZ-2BN), N1-(4-(4,6-diphenyl-1,3,5-triazin-2-yl)phenyl)-N1-(4-(diphenylamino)phenyl)-N4,N4-diphenylbenzene-1,4-diamine (DPA-TRZ), 2-phenyl-5-(4-(10-phenylphenazin-5 (10H)-yl)phenyl)-1,3,4-oxadiazole (PPZ-DPO), 2-(4-(10H-phenoxazin-10-yl)phenyl)thianthrene-5,5,10,10-tetraoxide (PXZDSO2), 2,3,5,6-tetrakis(3,6-diphenylcarbazol-9-yl)-1,4-dicyanobenzene (4CzTPN-Ph), and the like.

In another aspect, the third compound may comprise a red emitting delayed fluorescent material having the PL $\lambda_{max}$ more than about 580 nm and less than or equal to about 610 nm. For example, the red delayed fluorescent material may comprise, but is not limited to, 1,3-bis[4-(10H-phenoxazin-10-yl)benzoyl]benzene (mPx2BBP), 10,10'-(sulfonylbis(4,1-phenylene))bis(5-phenyl-5,10-dihydrophenazine) (PPZ-DPS), 5,10-bis(4-(benzo[d]thiazol-2-yl)phenyl)-5,10-dihydrophenazine (DHPZ-2BTZ), 5,10-bis(4-(4,6-diphenyl-1,3,5-triazin-2-yl)phenyl)-5,10-dihydrophenazine (DHPZ-2TRZ), 7,10-bis(4-(diphenylamino)phenyl)-2,3-dicyanopyrazino phenanathrene (TPA-DCPP), and the like.

Figure 7:
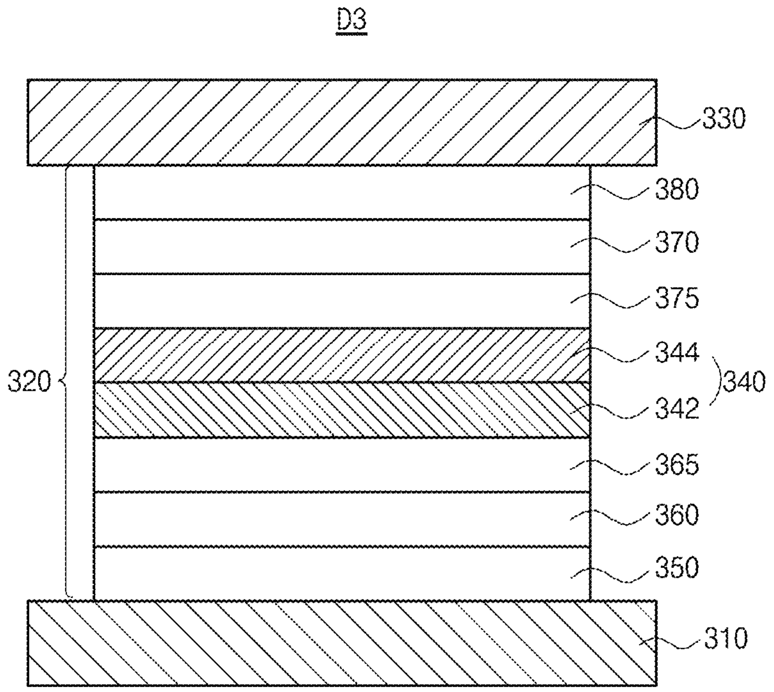
FIG. 7 is a schematic cross-sectional view illustrating an OLED diode in accordance with another exemplary aspect of the present disclosure.
Figure 8:
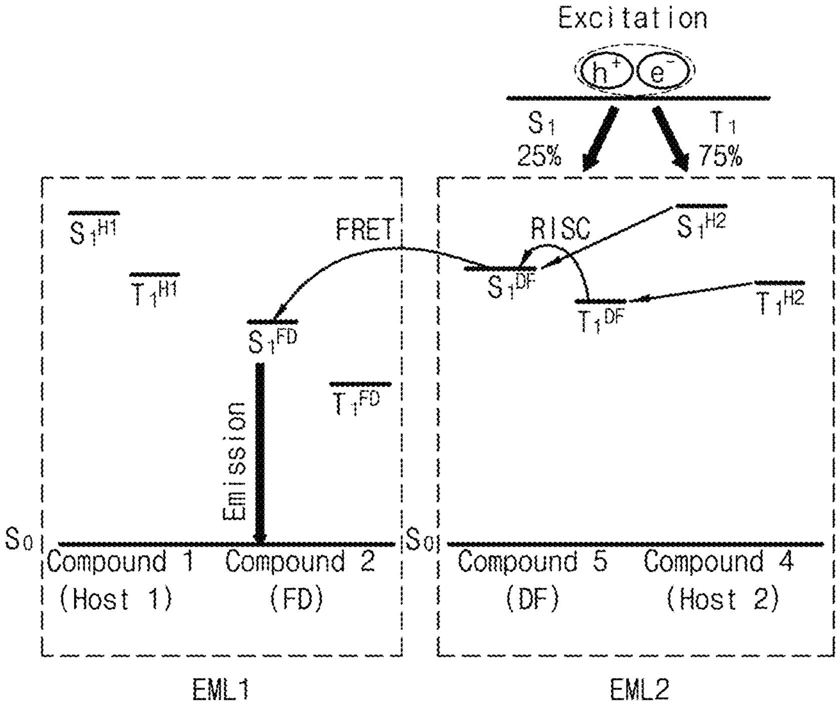
FIG. 8 is a schematic diagram illustrating luminous mechanism by energy level bandgap among luminous materials in accordance with another exemplary aspect of the present disclosure.

The OLEDs in accordance with the previous aspects have a single-layered EML. Alternatively, an OLED in accordance with the present disclosure may include multiple-layered EML. FIG. 7 is a schematic cross-sectional view illustrating an OLED having a double-layered EML in accordance with another exemplary aspect of the present disclosure. FIG. 8 is a schematic diagram illustrating luminous mechanism by energy level bandgap among luminous materials in accordance with another exemplary aspect of the present disclosure.

As illustrated in FIG. 7, the OLED D3 in accordance with this aspect includes first and second electrodes 310 and 330 facing each other and an emissive layer 320 having single emitting unit disposed between the first and second electrodes 310 and 330.

In one exemplary aspect, the emissive layer 320 comprises an EML 340. Also, the emissive layer 320 comprises an HIL 350 and an HTL 360 each of which is disposed sequentially between the first electrode 310 and the EML 340, and an ETL 370 and an IL 380 each of which is disposed sequentially between the EML 340 and the second electrode 330. Alternatively, the emissive layer 320 may further comprise an EBL 365 disposed between the HTL 360 and the EML 340 and/or a HBL 375 disposed between the EML 340 and the ETL 370.

As described above, the first electrode 310 may be an anode and may include, but is not limited to, a conductive material having a relatively large work function values such as ITO, IZO, SnO, ZnO, ICO, AZO, and the like. The second electrode 330 may be a cathode and may include, but is not limited to, a conductive material having a relatively small work function values such as Al, Mg, Ca, Ag, alloy thereof or combination thereof.

The HIL 350 is disposed between the first electrode 310 and the HTL 360. The HIL 350 may include, but is not limited to, MTDATA, NATA, 1T-NATA, 2T-NATA, CuPc, TCTA, NPB(NPD), HAT-CN, DFAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 350 may be omitted in compliance with the structure of the OLED D3.

The HTL 360 is disposed adjacently to the EML 340 between the first electrode 310 and the EML 340. The HTL 360 may include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EBL 365 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB and/or 2,8-bis(9-phenyl-9H-carbazol-3-yl)dibenzo[b,d]thiophene.

The EML 340 includes a first EML (EML1) 342 and a second EML (EML2) 344. The EML1 342 is disposed between the EBL 365 and the HBL 375 and the EML2 344 is disposed between the EML1 342 and the HBL 375. The configuration and energy levels among the luminous materials in the EML 340 will be explained in more detail below.

The HBL 375 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 375 may include a compound having a relatively low HOMO energy level compared to the emitting material in EML 340. The HBL 375 may include, but is not limited to, mCBP, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof.

The ETL 370 is disposed between the EML 340 and the EIL 380. In one exemplary aspect, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 370 may include, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 380 is disposed between the second electrode 320 and the ETL 370. In one exemplary aspect, the EIL 380 may include, but is not limited to, an alkali halide such as LiF, CsF, NaF, $BaF_2$ and the like, and/or an organic metal compound such as lithium benzoate, sodium stearate, and the like.

One of the EML1 342 and the EML2 344 includes the second compound having the fluorescent property FD that is any organic compound having the structure of Chemical Formulae 1 to 6, and the other of the EML1 342 and the EML2 344 includes a fifth compound having the delayed fluorescent property. Hereinafter, the EML 340 where the EML1 342 comprises the second compound and the EML2 344 comprises the fifth compound will be explained.

The EML1 342 comprise the first compound that may be the first host H1 and the second compound FD having the fluorescent property that may be any organic compound having the structure of Chemical Formulae 1 to 6. While the organic compound having the structure of Chemical Formulae 1 to 6 has an advantage in terms of color purity due to its narrow FWHM, but its internal quantum efficiency is low because its triplet exciton cannot be involved in the luminescence process.

The EML2 344 comprises the fourth compound that may be the second host H2 and the fifth compound DF having the delayed fluorescent property. The energy level bandgap ($\Delta E_{ST}^{DF}$) between the excited singlet energy level $S_1^{DF}$ and the excited triplet energy level $T_1^{DF}$ of the fifth compound in the EML2 344 is equal to or less than about 0.3 eV (see, FIG. 5) so that triplet exciton energy of the fifth compound can be transferred to its own singlet exciton energy via RISC mechanism. While the fifth compound has high internal quantum efficiency, but it has poor color purity due to its wide FWHM.

However, in this exemplary aspect, the singlet exciton energy and the triplet exciton energy of the fifth compound having the delayed fluorescent property in the EML2 344 can be transferred to the second compound FD in the EML1 342 disposed adjacently to the EML2 344 by FRET mechanism, and the ultimate light emission occurs in the second compound FD within the EML1 342.

In other words, the triplet exciton energy of the fifth compound is converted upwardly to its own singlet exciton energy in the EML2 344 by RISC mechanism. Then, the converted singlet exciton energy of the fifth compound is transferred to the singlet exciton energy of the second compound in the EML1 342 because the fifth compound DF has the excited singlet energy level $S_1^{DF}$ higher than the excited singlet energy level $S_1^{FD}$ of the second compound FD (See, FIG. 8).

The second compound FD in the EML1 342 can emit light using the triplet exciton energy as well as the singlet exciton energy. As described above, since Dexter energy transfer mechanism is limited in any organic compound having the structure of Chemical Formulae 1 to 6 owing to its molecular conformation, the singlet exciton energy is mainly transferred between the fifth and second compounds via FRET mechanism. As the triplet exciton energy loss by Dexter energy transfer mechanism is prevented, the OLED D3 can improved its quantum efficiency and enhance its color purity with narrow FWHM. Particularly, the second compound as the fluorescent dopant in the EML1 342 emits red light with high color purity and has very narrow FWHM. Accordingly, as the singlet exciton energy generated at the fifth compound in the EML2 344 is efficiently transferred to the second compound in the EML1 342, the OLED D3 can implement hyper fluorescence. In this case, while the fifth compound having the delayed fluorescent property only acts as transferring exciton energy to the second compound, substantial light emission is occurred in the EML1 342 including the second compound.

Each of the EML1 342 and the EML2 344 includes the first compound as the first host and the fourth compound as the second host, respectively. In one exemplary aspect, each of the first and fourth compounds may comprise independently, but is not limited to, BCzPh, TCP, TCTA, CBP, CDBP, DMFL-CBP, spiro-CBP, DPEPO, PCzB-2CN, mCzB-2CN, TCzl, mCP-CN, mCBP, mCP, PPT, TmPyPB, PYD-2Cz, $Bepp_2$, $Bebg_2$, TPB3, DCzDBT, DCzTPA, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicabazole.

In another aspect, the fifth compound in the EML2 344 may comprise a green, yellow-green or red emitting delayed fluorescent material having the PL $\lambda_{max}$ between about 520 nm and about 650 nm. For example, the green or yellow-green delayed fluorescent material having the PL $\lambda_{max}$ between about 520 nm and about 580 nm may comprise, but is not limited to, ATP-PXZ, m-ATP-PXZ, 4CzCNPy, PXZ-TRZ, bis-PXZ-TRZ, tri-PXZ-TRZ, PPZ-3TPT, BT2, DHPZ-2BI, DHPZ-2BN, DPA-TRZ, PPZ-DPO, PXZDSO2, 4CzTPN-Ph, and the like. In an alternative aspect, the red delayed fluorescent material the PL $\lambda_{max}$ more than about 580 nm and less than or equal to about 610 nm may comprise, but is not limited to, mPx2BBP, PPZ-DPS, DHPZ-2BTZ, DHPZ-2TRZ, TPA-DCPP, and the like.

In one exemplar aspect, the second compound which may be anyone having the structure of Chemical Formulae 1 to 6 may have, but is not limited to, PL $\lambda_{max}$ between about 580 nm and about 650 nm, e.g. about 580 nm and about 620 nm. In addition, the second compound may have Abs. $\lambda_{max}$ that is substantially identical to or longer than the PL $\lambda_{max}$ of the fifth compound having the delayed fluorescent property so that the exciton energy can be efficiently transferred from the fifth compound to the second compound. As an example, the second compound may have, but is not limited to, Abs. $\lambda_{max}$ between about 530 nm to about 590 nm, e.g. about 540 nm to about 580 nm. The fifth compound may have, but is not limited to, PL $\lambda_{max}$ between about 520 nm and about 610 nm.

In one exemplary aspect, each of the contents of the first and fourth compounds in the EML1 342 and the EML2 344 may be larger than the contents of the second and fifth compounds in the same layer. Also, the contents of the fifth compound in the EML2 344 may be larger than the contents of the second compound in the EML1 342. In this case, exciton energy can be transferred sufficiently from the fifth compound DF to the second compound FD via FRET mechanism. As an example, the contents of the second compound in the EML1 342 may be, but is not limited to, about 1 wt % to about 50 wt %, preferably about 1 wt % to about 30 wt %. On the other hand, the contents of the fifth compound in the EML2 344 may be, but is not limited to, about 10 wt % to about 50 wt %, preferably about 10 wt % to about 40 wt %.

Now, we will explain the energy level relationships among the luminous material in the EML 340 with referring to FIG. 8. As illustrated in FIG. 8, the excited singlet energy level $S_1^{H1}$ of the first compound H1, which may be the first host, in the EML1 342 is higher than the excited singlet energy level $S_1^{FD}$ of the second compound FD which may be the fluorescent material. Alternatively, the excited triplet energy level $T_1^{H1}$ of the first compound H1 may be higher than the excited singlet energy level $T_1^{FD}$ of the second compound FD.

Also, each of the excited singlet energy level $S_1^{H2}$ and excited triplet energy level $T_1^{H2}$ of the fourth compound H2, which may be the second host, in the EML2 344 may be higher than each of the excited singlet energy level $S_1^{DF}$ and the excited triplet energy level $T_1^{DF}$ of the fifth compound DF having the delayed fluorescent property, respectively. In addition, each of the excited singlet energy levels $S_1^{H1}$ and the excited triplet energy level $T_1^{H1}$ of the first compound H1 in the EML1 342 may be higher than each of excited singlet energy level $S_1^{DF}$ and the excited triplet energy level $T_1^{DF}$ of the fifth compound DF in the EML2 344.

Moreover, the excited singlet energy level $S_1^{DF}$ of the fifth compound DF in the EML2 344 is higher than the excited singlet energy level $S_1^{FD}$ of the second compound FD in the EML1 342. Alternatively, the excited triplet energy level $T_1^{DF}$ of the fifth compound DF in the EML2 344 is higher than the excited triplet energy level $T_1^{FD}$ of the second compound FD in the EML1 342. When the luminous materials do not satisfy the requirements above, excitons may be quenched as non-radiation at each of the second compound FD having the fluorescent property and the fifth compound DF having the delayed fluorescent property or excitons cannot be transferred to the dopants from the hosts, and results in luminous efficiency reduction in the OLED D3.

The energy level bandgap between the excited singlet energy level $S_1^{DF}$ and the excited triplet energy level $T_1^{DF}$ of the fifth compound DF in the EML2 344 may be less than or equal to about 0.3 eV. Also, the energy level bandgap ($|HOMO^H-HOMO^{DF}|$) between the HOMO energy level ($HOMO^H$) of the first and/or fourth compounds and the HOMO energy level ($HOMO^{DF}$) of the fifth compound, or the energy level bandgap ($|LUMO^H-LUMO^{DF}|$) between a LUMO energy level ($LUMO^H$) of the first and/or fourth compounds and the LUMO energy level ($LUMO^{DF}$) of the fifth compound may be equal to or less than about 0.5 eV.

In another exemplary aspect, the first compound H1, which is included in the EML1 342 together with the second compound FD having the fluorescent property, may be the same material as the EBL 365. In this case, the EML1 342 may have an electron blocking function as well as an emission function. In other words, the EML1 342 can act as a buffer layer for blocking electrons. In one aspect, the EBL 365 may be omitted where the EML1 342 may be an electron blocking layer as well as an emitting material layer.

In another aspect, the EML1 342 may comprise the fourth compound H2 and the fifth compound DF having the delayed fluorescent property and the EML2 344 may comprise the first compound H1 and the second compound FD having the fluorescent property such as any organic compound having the structure of Chemical Formulae 1 to 6. In this case, the first compound H1 in the EML2 344 may be the same as the HBL 375. In this case, the EML2 344 may have a hole blocking function as well as an emission function. In other words, the EML2 344 can act as a buffer layer for blocking holes. In one aspect, the HBL 375 may be omitted where the EML2 344 may be a hole blocking layer as well as an emitting material layer.

Figure 9:
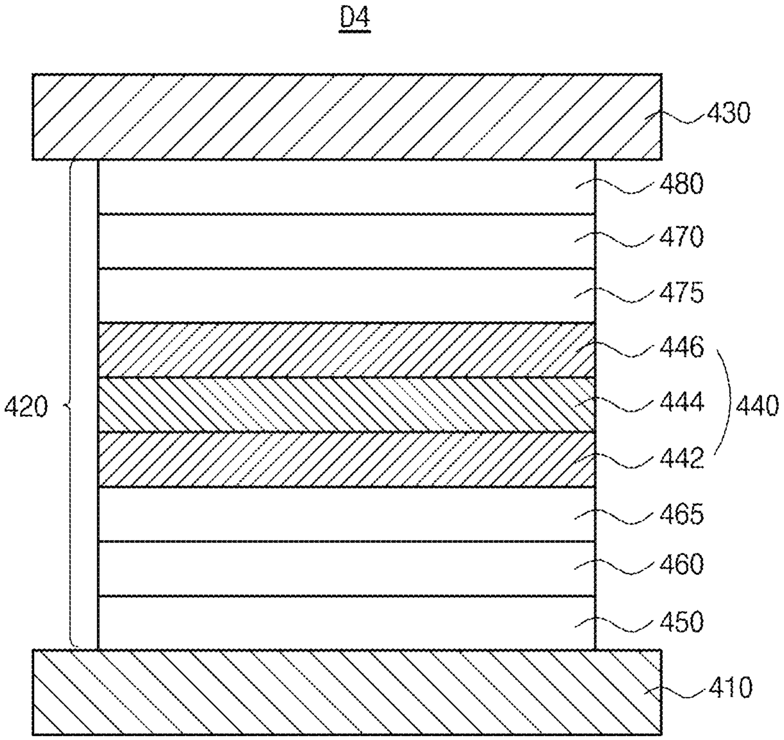
FIG. 9 is a schematic cross-sectional view illustrating an OLED in accordance with another exemplary aspect of the present disclosure.
Figure 10:
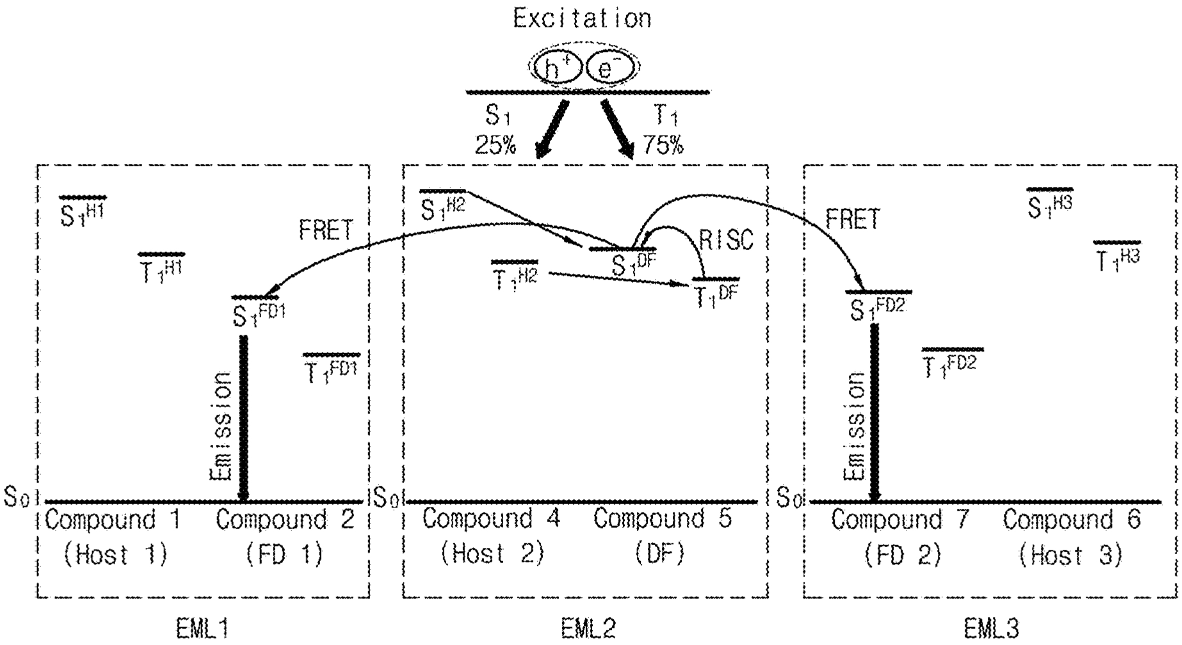
FIG. 10 is a schematic diagram illustrating luminous mechanism by energy level bandgap among luminous materials in accordance with another exemplary aspect of the present disclosure.

An OLED having a triple-layered EML will be explained. FIG. 9 is a schematic cross-sectional view illustrating an OLED having a triple-layered EML in accordance with another exemplary aspect of the present disclosure. FIG. 10 is a schematic diagram illustrating luminous mechanism by energy level bandgap among luminous materials in accordance with another exemplary aspect of the present disclosure.

As illustrated in FIG. 9, the OLED D4 in this aspect comprises first and second electrodes 410 and 430 facing each other and an emissive layer 420 disposed between the first and second electrodes 410 and 430.

In one exemplary aspect, the emissive layer 420 having single emitting unit comprises a three-layered EML 440. The emissive layer 420 comprises an HIL 450 and an HTL 460 each of which is disposed sequentially between the first electrode 410 and the EML 440, and an ETL 470 and an EIL 480 each of which is disposed sequentially between the EML 440 and the second electrode 430. Alternatively, the emissive layer 420 may further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1, D2 and D3.

The EML 440 comprises a first EML (EML1) 442, a second EML (EML2) 444 and a third EML (EML3) 446. The EML1 442 is disposed between the EBL 465 and the HBL 475, the EML2 444 is disposed between the EBL 465 and the EML1 442 and the EML3 446 is disposed between the EML1 442 and the HBL 475.

Each of the EML1 442 and the EML3 446 comprises the second compound FD1, which may be the first fluorescent material, and a seventh compound FD2, which may be a second fluorescent material, respectively. The EML2 444 comprises the fifth compound DF which may be the delayed fluorescent material. For example, each of the second and fifth compounds FD1 and FD2 may comprise any organic compound having the structure of Chemical Formulae 1 to 6. In addition, each of the EML1 442, EML2 444 and EML3 446 further includes the first, fourth and sixth compounds H1, H2 and H3 each of which may be the first to third hosts, respectively.

In accordance with this aspect, the singlet energy as well as the triplet energy of the fifth compound DF, i.e. the delayed fluorescent material in the EML2 444 can be transferred to the second and seventh compounds FD1 and FD2, i.e. the fluorescent materials each of which is included in the EML1 442 and EML3 446 disposed adjacently to the EML2 444 by FRET mechanism. Accordingly, the ultimate emission occurs in the second and seventh compounds FD1 and FD2 in the EML1 442 and the EML3 446.

In other words, the triplet exciton energy of the fifth compound DF having the delayed fluorescent property in the EML2 444 is converted upwardly to its own singlet exciton energy by RISC mechanism, then the singlet exciton energy of the fifth compound DF is transferred to the singlet exciton energy of the second and seventh compounds FD1 and FD2 in the EML1 442 and the EML3 446 because the fifth compound DF has the excited singlet energy level $S_1^{DF}$ higher than each of the excited singlet energy levels $S_1^{FD1}$ and $S_1^{FD2}$ of the second and seventh compounds FD1 and FD2 (see, FIG. 10).

Since the second and seventh compounds FD1 and FD2 in the EML1 442 and EML3 446 can emit light using the singlet exciton energy and the triplet exciton energy derived from the fifth compound DF, the OLED D4 can improve its luminous efficiency. In addition, since each of the second and seventh compounds FD1 and FD2 having the fluorescent property each of which may be any organic compound having the structure of Chemical Formulae 1 to 6, has relatively narrow FWHM compared to the fifth compound DF, the OLED D4 can enhance its color purity.

In this case, while the fifth compound DF having the delayed fluorescent property only acts as transferring exciton energy to the second and seventh compounds FD1 and FD2, substantial light emission is occurred in the EML1 442 and the EML3 446 including the second and seventh compounds FD1 and FD2.

Each of the EML1 442 to the EML3 446 includes the first compound H1 as the first host, the fourth compound H2 as the second host and the sixth compound H3 as the third host, respectively. In one exemplary aspect, each of the first, fourth and sixth compounds H1, H2 and H3 may comprise independently, but is not limited to, BCzPh, TCP, TCTA, CBP, CDBP, DMFL-CBP, spiro-CBP, DPEPO, PCzB-2CN, mCzB-2CN, TCzl, mCP-CN, mCBP, mCP, PPT, TmPyPB, PYD-2Cz, $Bepp_2$, $Bebg_2$, TPB3, DCzDBT, DCzTPA, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole) and/or 9-(6-(9H-carbazol-9-yl)pyridin-3-yl)-9H-3,9'-bicabazole.

In another aspect, the fifth compound DF in the EML2 444 may comprise a green, yellow-green or red emitting delayed fluorescent material having the PL $\lambda_{max}$ between about 520 nm and about 650 nm. For example, the green or yellow-green delayed fluorescent material having the PL $\lambda_{max}$ between about 520 nm and about 580 nm may comprise, but is not limited to, ATP-PXZ, m-ATP-PXZ, 4CzCNPy, PXZ-TRZ, bis-PXZ-TRZ, tri-PXZ-TRZ, PPZ-3TPT, BT2, DHPZ-2BI, DHPZ-2BN, DPA-TRZ, PPZ-DPO, PXZDSO2, 4CzTPN-Ph, and the like. In an alternative aspect, the red delayed fluorescent material the PL $\lambda_{max}$ more than about 580 nm and less than or equal to about 610 nm may comprise, but is not limited to, mPx2BBP, PPZ-DPS, DHPZ-2BTZ, DHPZ-2TRZ, TPA-DCPP, and the like.

In one exemplar aspect, each of the second and seventh compounds FD1 and FD2 which may be anyone having the structure of Chemical Formulae 1 to 6 may have, but is not limited to, PL $\lambda_{max}$ between about 580 nm and about 650 nm, e.g. about 580 nm and about 620 nm. In addition, each of the second and seventh compounds FD1 and FD2 may have Abs. $\lambda_{max}$ that is substantially identical to or longer than the PL $\lambda_{max}$ of the fifth compound having the delayed fluorescent property so that the exciton energy can be efficiently transferred from the fifth compound DF to the second and seventh compounds FD1 and FD2. As an example, each of the second and seventh compounds FD1 and FD2 may have, but is not limited to, Abs. $\lambda_{max}$ between about 530 nm to about 590 nm, e.g. about 540 nm to about 580 nm. The fifth compound DF may have, but is not limited to, PL $\lambda_{max}$ between about 520 nm and about 610 nm.

In one exemplary aspect, each of the contents of the first, fourth and sixth compounds H1, H2 and H3 as the host in the EML1 442 to the EML3 446 may be larger than the contents of the second, fifth and seventh FD1, DF and FD2 compounds as the dopants in the same layer. Also, the contents of the fifth compound DF in the EML2 444 may be larger than the contents of each of the second and seventh compounds FD1 and FD2 in the EML1 442 and in the EML3 446. In this case, exciton energy can be transferred sufficiently from the fifth compound DF to the second and seventh compounds FD1 and FD2 via FRET mechanism. As an example, the contents of each of the second and seventh compounds FD1 and FD2 in the EML1 442 and in the EML3 446 may be, but is not limited to, about 1 wt % to about 50 wt %, preferably about 1 wt % to about 30 wt %. On the other hand, the contents of the fifth compound DF in the EML2 444 may be, but is not limited to, about 10 wt % to about 50 wt %, preferably about 10 wt % to about 40 wt %.

Now, we will explain the energy level relationships among the luminous material in the EML 440 with referring to FIG. 10. As illustrated in FIG. 10, the excited singlet energy level $S_1^{H1}$ of the first compound H1, which may be the first host, in the EML1 442 is higher than the excited singlet energy level $S_1^{FD1}$ of the second compound FD1 which may be the first fluorescent material. Also, the excited singlet energy level $S_1^{H3}$ of the sixth compound H3, which may be the third host, in the EML3 446 is higher than the excited singlet energy level $S_1^{FD2}$ of the seventh compound FD2 which may be the second fluorescent material. Alternatively, the excited triplet energy levels $T_1^{H1}$ and $T_1^{H2}$ of the first and sixth compounds H1 and H3 may be higher than each of the excited singlet energy levels $T_1^{FD1}$ and $T_1^{FD2}$ of the second and seventh compounds FD1 and FD2, respectively.

Also, each of the excited singlet energy level $S_1^{H2}$ and excited triplet energy level $T_1^{H2}$ of the fourth compound H2, which may be the second host, in the EML2 444 may be higher than each of the excited singlet energy level $S_1^{DF}$ and the excited triplet energy level $T_1^{DF}$ of the fifth compound having the delayed fluorescent property, respectively. In addition, each of the excited singlet energy levels $S_1^{H1}$ and $S_1^{H3}$ and the excited triplet energy levels $T_1^{H1}$ and $T_1^{H3}$ of the first and sixth compounds H1 and H3 in the EML1 442 and in the EML3 446 may be higher than each of excited singlet energy level $S_1^{DF}$ and the excited triplet energy level $T_1^{DF}$ of the fifth compound DF in the EML2 444.

Moreover, the excited singlet energy level $S_1^{DF}$ of the fifth compound DF in the EML2 444 is higher than each of the excited singlet energy levels $S_1^{FD1}$ and $S_1^{FD2}$ of the second and seventh compounds FD1 and FD2 in the EML1 442 and in the EML3 446. Alternatively, the excited triplet energy level $T_1^{DF}$ of the fifth compound DF in the EML2 444 is higher than each of the excited triplet energy levels $T_1^{FD1}$ and $T_1^{FD2}$ of the second and seventh compounds FD1 and FD2 in the EML1 442 and in the EML3 446.

In one exemplary aspect, the first compound H1, which is included in the EML1 442 together with the second compound FD1 that is any organic compound having the structure of Chemical Formulae 1 to 6, may be the same material as the EBL 465. In this case, the EML1 442 may have an electron blocking function as well as an emission function. In other words, the EML1 442 can act as a buffer layer for blocking electrons. In one aspect, the EBL 465 may be omitted where the EML1 442 may be an electron blocking layer as well as an emitting material layer.

The sixth compound H3, which is included in the EML3 446 together with the seventh compound FD2, may be the same material as the HBL 475. In this case, the EML3 446 may have a hole blocking function as well as an emission function. In other words, the EML3 446 can act as a buffer layer for blocking holes. In one aspect, the HBL 475 may be omitted where the EML3 446 may be a hole blocking layer as well as an emitting material layer.

In still another exemplary aspect, the first compound H1 in the EML1 442 may be the same material as the EBL 455 and the sixth compound H3 in the EML3 446 may be the same material as the HBL 475. In this aspect, the EML1 442 may have an electron blocking function as well as an emission function, and the EML3 446 may have a hole blocking function as well as an emission function. In other words, each of the EML1 442 and the EML3 446 can act as a buffer layer for blocking electrons or hole, respectively. In one aspect, the EBL 465 and the HBL 475 may be omitted where the EML1 442 may be an electron blocking layer as well as an emitting material layer and the EML3 446 may be a hole blocking layer as well as an emitting material layer.

Figure 11:
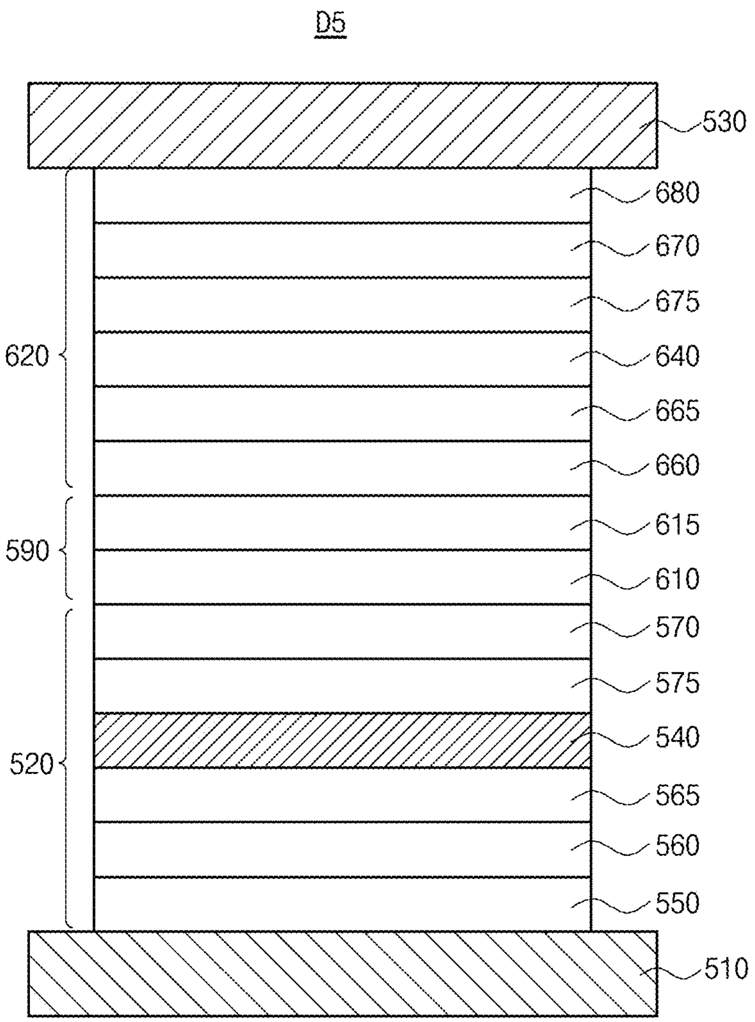
FIG. 11 is a schematic cross-sectional view illustrating an OLED in accordance with another exemplary aspect of the present disclosure.

In the above aspects, the OLEDs having only one emitting unit are described. Unlike the above aspects, the OLED may have multiple emitting units so as to form a tandem structure. FIG. 11 is a cross-sectional view illustrating an OLED in accordance with still another aspect of the present disclosure.

As illustrated in FIG. 11, the OLED D5 in accordance with the fifth aspect of the present disclosure comprises first and second electrodes 510 and 530 facing each other, a first emitting unit 520 disposed between the first and second electrodes 510 and 530, a second emitting unit 620 disposed between the first emitting unit 520 and the second electrode 530, and a charge generation layer (CGL) 590 disposed between the first and second emitting units 520 and 620.

The first electrode 510 may be an anode and include, but is not limited to, a conductive material having a relatively large work function values. As an example, the first electrode 510 may include, but is not limited to, ITO, IZO, SnO, ZnO, ICO, AZO, and the like. The second electrode 530 may be a cathode and may include, but is not limited to, a conductive material having a relatively small work function values such as Al, Mg, Ca, Ag, alloy thereof or combination thereof.

The first emitting unit 520 comprises a lower EML 540. Also the first emitting unit comprises a HIL 560 and a first HTL (HTL1) each of which is disposed sequentially between the first electrode 510 and the lower EML 540, a first ETL (ETL1) 570 disposed between the lower EML 540 and the CGL 590. Alternatively, the first emitting unit 520 may further comprise a first EBL (EBL1) 565 disposed between the HTL1 560 and the lower EML 540 and/or a first HBL (HBL1) 575 disposed between the lower EML 540 and the ETL1 570.

The second emitting unit 620 comprises an upper EML 640. The second emitting unit 620 comprises a second HTL (HTL2) 660 disposed between the CGL 590 and the upper EML 640, and a second ETL (ETL2) 670 and an EIL 680 each of which is disposed sequentially between the upper EML 640 and the second electrode 530. Alternatively, the second emitting unit 620 may further comprise a second EBL (EBL2) 665 disposed between the HTL2 660 and the upper EML 640 and/or a second HBL (HBL2) 675 disposed between the upper EML 640 and the ETL2 670.

At least one of the lower EML 540 and the upper EML 640 may comprise any organic compound having the structure of Chemical Formulae 1 to 6 and emit red (R) light, and the other of the lower EML 540 and the upper EML 640 may emit blue (B) and/or green (G) light. Hereinafter, the OLED D5, where the lower EML 540 emits red (R) light and the upper EML 640 emits blue (B) and/or green (G) light, will be explained.

The HIL 550 is disposed between the first electrode 510 and the HTL1 560 and improves an interface property between the inorganic first electrode 510 and the organic HTL1 560. In one exemplary aspect, the HIL 550 may comprise, but is not limited to, MTDATA, NATA, 1T-NATA, 2T-NATA, CuPc, TCTA, NPB(NPD), HAT-CN, DFAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 550 may be omitted in compliance with a structure of the OLED D5.

Each of the HTL1 560 and the HTL2 660 may independently include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

Each of the ETL1 570 and the ETL2 670 facilitates electron transportations in the first emitting unit 520 and the second emitting unit 620, respectively. Each of the ETL1 570 and the ETL2 670 may independently include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the ETL1 570 and the ETL2 670 may independently include, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ, respectively.

The EIL 680 is disposed between the second electrode 530 and the ETL2 670, and can improve physical properties of the second electrode 530 and therefore, can enhance the lifetime of the OLED D5. In one exemplary aspect, the EIL 580 may include, but is not limited to, an alkali halide such as LiF, CsF, NaF, $BaF_2$ and the like, and/or an organic metal compound such as lithium benzoate, sodium stearate, and the like.

Each of the EBL1 565 and the EBL2 665 may independently include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole, respectively.

Each of the HBL1 575 and the HBL2 675 may independently include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the HBL1 575 and the HBL2 675 may independently include, but is not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

In one exemplary aspect, when the upper EML 640 emits blue light, the upper EML 640 may emit deep blue or sky blue light. In this case, the upper EML 640 may comprise a blue host and a blue dopant. For example, the blue host may comprise, but is not limited to, mCP, mCP-CN, mCBP, CBP-CN, 9-(3-(9H-Carbazol-9-yl)phenyl)-3-(diphenylphosphoryl)-9H-carbazole (mCPPO1), 3,5-Di(9H-carbazol-9-yl)biphenyl (Ph-mCP), TSPO1, 9-(3'-(9H-carbazol-9-yl)-[1,1'-biphenyl]-3-yl)-9H-pyrido[2,3-b]indole (CzBPCb), Bis(2-methylphenyl)diphenylsilane (UGH-1), 1,4-Bis(triphenylsilyl)benzene (UGH-2), 1,3-Bis(triphenylsilyl)benzene (UGH-3), 9,9-Spiorobifluoren-2-yl-diphenyl-phosphine oxide (SPPO1), 9,9'-(5-(Triphenylsilyl)-1,3-phenylene)bis(9H-carbazole) (SimCP), and the like.

The blue dopant may comprise, but is not limited to, perylene, 4,4'-Bis[4-(di-p-tolylamino)styryl]biphenyl (DPAVBi), 4-(Di-p-tolylamino)-4-4'-[(di-p-tolylamino)styryl]stilbene (DPAVB), 4,4'-Bis[4-(diphenylamino)styryl]

biphenyl (BDAVBi), 2,5,8,11-Tetra-tetr-butylperylene (TBPe), Bis(2-(2-hydroxyphenyl)pyridinato)beryllium (Bepp2), 9-(9-Phenylcarbazole-3-yl)-10-(naphthalene-1-yl) anthracene (PCAN), mer-Tris(1-phenyl-3-methylimidazolin-2-ylidene-C,C(2)'iridium(III) (mer-Ir(pmi)$_3$), fac-Tris(1,3-diphenyl-benzimidazolin-2-ylidene-C,C(2)'iridium(III) (fac-Ir(dpbic)$_3$), Bis(3,4,5-trifluoro-2-(2-pyridyl)phenyl-(2-carboxypyridyl)iridium(III) (Ir(tfpd)$_2$pic), tris(2-(4,6-difluorophenyl)pyridine)iridium(III) (Ir(Fppy)$_3$), Bis[2-(4,6-difluorophenyl)pyridinato-C$^2$,N](picolinato)iridium(III) (FIrpic), and the like. In this case, the upper EML 640 may emit blue light having wavelength of about 450 nm to about 500 nm.

In an alternative aspect, when the upper EML 640 is the green EML, the upper EML 640 may emit green or yellow-green light. In this case, the upper EML 640 may comprise a green host and a green or yellow-green dopant. The green host may comprise, but is not limited to, Bczph, CBP, TCP, TCTA, CDBP, DMFL-CBP, Spiro-CBP, DPEPO, PCzB-2CN, mCzB-2CN, TcZ1, and the like.

For example, the green or yellow-green dopant may comprise, but is not limited to, [Bis(2-phenylpyridine)](pyridyl-2-benzofuro[2,3-b]pyridine)iridium, fac-Tris(2-phenylpyridine)iridium(III) (fac-Ir(ppy)$_3$), Bis(2-phenylpyridine)(acetylacetonate)iridium(11) (Ir(ppy)$_2$(acac)), Tris[2-(p-tolyl)pyridine]iridium(III) (Ir(mppy)$_3$), Bis(2-(naphthalene-2-yl)pyridine)(acetylacetonate)iridium(III) (Ir(npy)$_2$acac), Tris(2-phenyl-3-methyl-pyridine)iidium (Ir(3mppy)$_3$), fac-Tris(2-(3-p-xylyl)phenyl)pyridine iridium (III) (TEG), 5,6,11,12-Tetraphenylnaphthalene (Rubrene), 2,8-Di-tert-butyl-5,11-bis(4-tert-butylphenyl)-6,12-diphenyltetracene (TBRb), (Bis(2-phenylbenzothiazolato)(acetylacetonate)irdium(III) (Ir(BT)$_2$(acac)), (Bis(2-(9,9-diethytl-fluoren-2-yl)-1-phenyl-1H-benzo[d]imdiazolato)(acetylacetonate)iridium(III) (Ir(fbi)$_2$(acac)) Bis(2-phenylpyridine)(3-(pyridine-2-yl)-2H-chromen-2-onate) iridium(III) (fac-Ir(ppy)$_2$Pc), Bis(2-(2,4-difluorophenyl) quinoline)(picolinate)iridium(III) (FPQIrpic), and the like. In this case, the upper EML 640 may emit green or yellow-green light having wavelength of about 500 nm to about 580 nm.

The CGL 590 is disposed between the first emitting unit 520 and the second emitting unit 620. The CGL 590 includes an N-type CGL 610 disposed adjacently to the first emitting unit 520 and a P-type CGL 615 disposed adjacently to the second emitting unit 620. The N-type CGL 610 injects electrons into the first emitting unit 520 and the P-type CGL 615 injects holes into the second emitting unit 620.

As an example, the N-type CGL 610 may be an organic layer doped with an alkali metal such as Li, Na, K and/or Cs and/or an alkaline earth metal such as Mg, Sr, Ba and/or Ra. For example, a host used in the N-type CGL 610 may include, but is not limited to, an organic compound such as Bphen or MTDATA. The alkali metal or the alkaline earth metal may be doped with about 0.01 wt % to about 30 wt %.

The P-type CGL 615 may include, but is not limited to, an inorganic material selected from the group consisting of tungsten oxide ($WO_x$), molybdenum oxide ($MoO_x$), beryllium oxide ($Be_2O_3$), vanadium oxide ($V_2O_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The lower EML 540 comprises the first compound that can be the host and the second compound that can be the fluorescent material. The second compound may comprise any organic compound having the structure of Chemical Formulae 1 to 6.

Similar to the first aspect, the singlet exciton energy generated at the first compound that may be the host in the lower EML 540 can be transferred to the singlet exciton of the second compound that may the fluorescent material. The excited singlet energy level $S_1^H$ of the first compound as the host is higher than the excited singlet energy level $S_1^{FD}$ of the second compound as the fluorescent dopant. Alternatively, the excited triplet energy level $T_1^{H1}$ of the first compound may be higher than the excited triplet energy level $T_1^{FD}$ of the second compound (see, FIG. 3). In this case, the exciton energy generated at the first compound may be transferred to the second compound. As an example, the first compound may have a luminescent spectrum overlapping widely to an absorption spectrum of the second compound, thus the exciton energy can be efficiently transferred from the first compound to the second compound.

As an example, the first compound may have, but is not limited to, maximum photoluminescence wavelength (PL $\lambda_{max}$) between about 500 nm and about 600 nm. The second compound that is anyone having the structure of Chemical Formulae 1 to 6 may have, but is not limited to, PL $\lambda_{max}$ between about 580 nm and about 650 nm, e.g. about 580 nm and about 620 nm. Also, the second compound may have, but is not limited to, maximum absorption wavelength (Abs. $\lambda_{max}$) between about 530 nm to about 590 nm, e.g. about 540 nm to about 580 nm. In this case, the Abs. $\lambda_{max}$ of the second compound may be substantially identical to or longer than the PL λmax of the first compound so that exciton energy can be efficiently transferred from the first compound to the second compound.

The first compound as the host may comprise, but is not limited to, BCzPh, TCP, TCTA, CBP, CDBP, DMFL-CBP, spiro-CBP, DPEPO, PCzB-2CN, mCzB-2CN, TCzl, mCP-CN, mCBP, mCP, PPT, TmPyPB, PYD-2Cz, Bepp$_2$, Bebg$_2$, TPB3, DCzDBT, DCzTPA, TSPO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl) phenyl)-9H-3,9'-bicarbazole) and/or 9-(6-(9H-carbazol-9-yl)pyridin-3-yl)-9H-3,9'-bicabazole.

When the lower EML 540 comprise the first compound and the second compound, the contents of the second compound may be, but is not limited to, about 1 wt % to about 50 wt %, preferably about 1 wt % to about 30 wt %.

In an alternative aspect, the lower EML 540 may comprise the first compound that may be the host, the second compound that may be the fluorescent material, and the third compound that may be the delayed fluorescent material (see, FIG. 4). In another exemplary aspect, the lower EML 540 may have a double-layered structure that comprises an EML1 and an EML2. In this case, the EML1 may comprise the first compound that may be the first host and the second compound that may be the first fluorescent material while the EML2 may comprise the fourth compound that may be the second host and the fifth compound that may be the delayed fluorescent or phosphorescent material (see, FIG. 7). In still another aspect, the lower EML 540 may have a triple-layered structure that further comprises an EML3 disposed oppositely to the EML1 with respect to the EML2. In this case, the EML3 may comprise the sixth compound that may be the third host and the seventh compound that may be the second fluorescent material (see, FIG. 9).

In still another exemplary aspect, an OLED of the present disclosure may comprise three or more emitting units. For example, the OLED may further comprise a third emitting unit disposed between the second emitting unit 620 and the second electrode 530 and a second CGL disposed between the second emitting unit 620 and the third emitting unit.

EXAMPLES

Synthesis Example 1: Synthesis of Compound 1-1 [N,N,6,13-tetraphenylnaphtho[1',8':5,6,7]-s-indaceno [1,2,3-cd]perylen-9-amine]

(1) Synthesis of Intermediate 1-1C

[Reaction Formula 1-1]

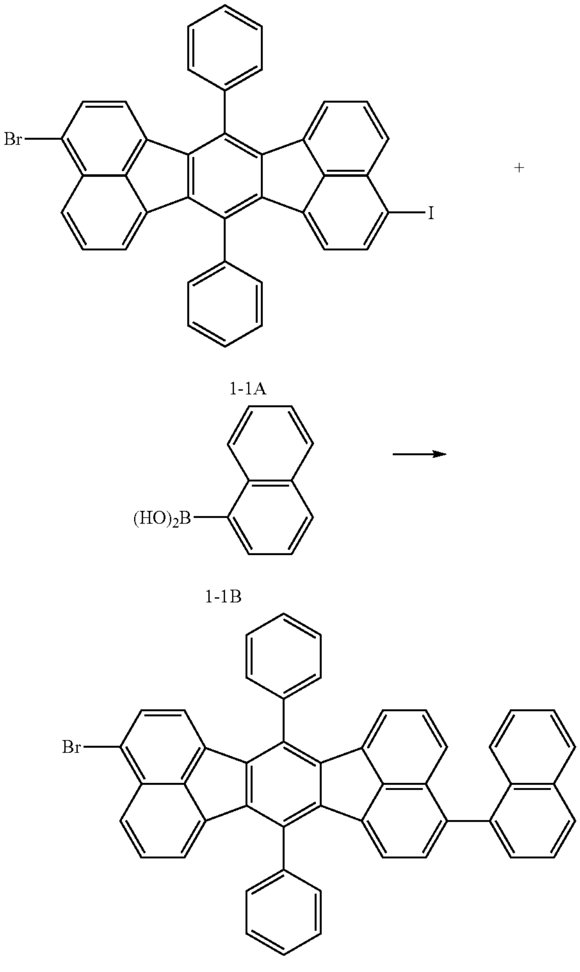

1-1A 1-1B 1-1C

Compound 1-1A (1 equivalent) dissolved in a mixed solvent of toluene/ethanol (5:1 by volume ratio) was added into a reactor under nitrogen atmosphere, and then compound 1-1B (1 equivalent) was added into the reactor. Sodium carbonate (3.0 equivalents) dissolved in DI water was added into the reactor, tetrakis(triphenylphosphine) palladium(0) ($Pd(PPh_3)_4$, 0.05 equivalent) was added into the reactor, and then the reactor was stirred at 90° C. for 12 hours. After reaction was complete, the organic layer was extracted with dichloromethane and DI water, and the solvent was removed under reduced distillation. The crude product was separated and purified with a column chromatography using a hexane/dichloromethane eluent to give the Intermediate 1-1C.

(2) Synthesis of Intermediate 1-1D

[Reaction Formula 1-2]

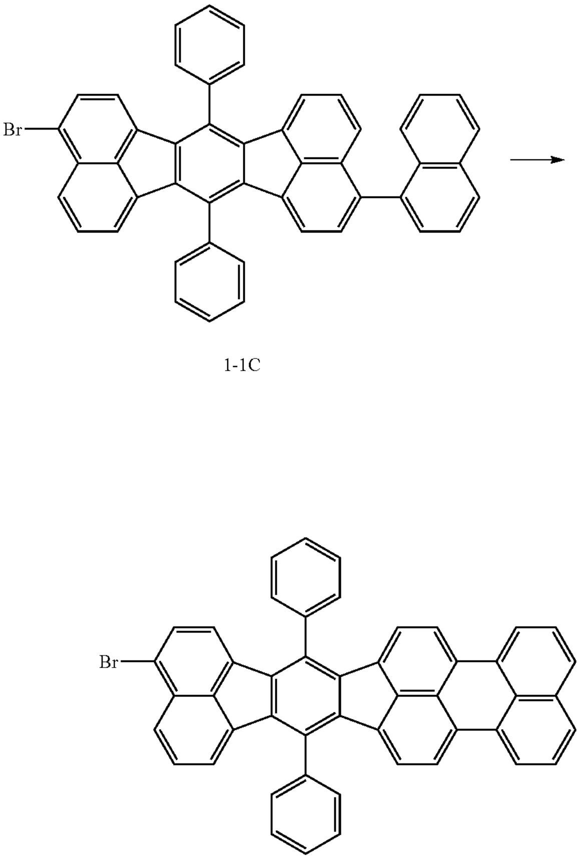

1-1C 1-1D

The Intermediate 1-1C (5 g) dissolved in a mixed solvent of trifluoroacetic acid (500 mL) and trifluoride diethyl etherate (30 mL) was added into a reactor, 2,3-dichloro-5,6-dicyano-p-benzoquinone (DDQ, 6 g) was added into the reactor, the reactor was purged with nitrogen, and then the compounds were reacted at room temperature for one hour. Ferrocene (5.3 g) was added to the reactor and the reactor was stirred again for one hour. After reaction was complete, the organic layer was extracted with dichloromethane and DI water, and the solvent was removed under reduced distillation. The crude product was separated and purified with a column chromatograph using a hexane/dichloromethane eluent to give the Intermediate 1-1D.

(3) Synthesis of Compound 1-1

[Reaction Formula 1-3]

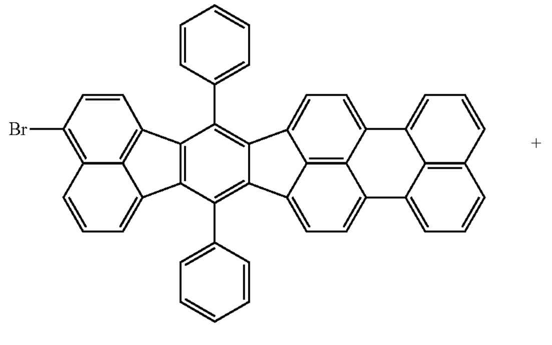

1-1D

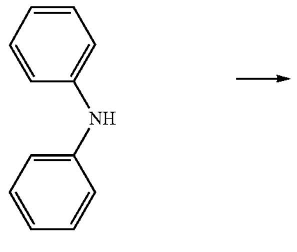

1-1E

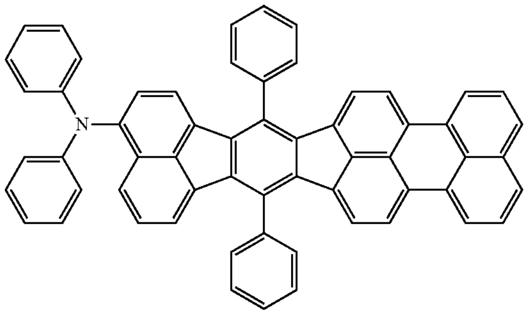

1-1

The Intermediate 1-1D (1 equivalent), compound 1-1E (1.2 equivalents), tris(dibenzylideneacetone)dipalladium(0) ($Pd_2(dba)_3$, 0.03 equivalent) and sodium t-butoxide (1.4 equivalents) dissolved in toluene were added into a reactor under nitrogen atmosphere, and the reactor was stirred at 110° C. for 8 hours. After reaction was complete, the organic layer was extracted with dichloromethane and DI water, and the solvent was removed under reduced distillation. The crude product was separated and purified with a column chromatography using hexane/dichloromethane eluent to give Compound 1-1.

Synthesis Example 2: Synthesis of Compound 1-8 [[N,N-bis(4-(tert-butyl)phenyl)-6,13-diphenylnaphtho[1',8':5,6,7]-s-indaceno[1,2,3-cd]perylen-9-amine]

[Reaction Formula 2]

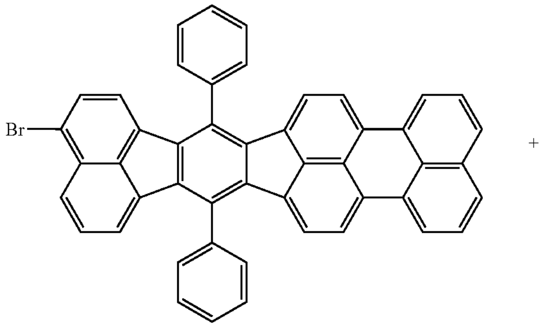

1-1D

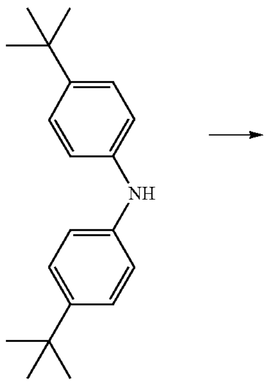

1-8A

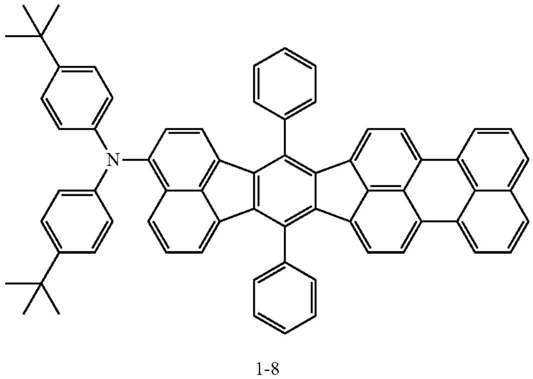

1-8

The Intermediate 1-1D (1 equivalent), compound 1-8A (1.2 equivalents), $Pd_2(dba)_3$ (0.03 equivalent) and sodium t-butoxide (1.4 equivalents) dissolved in toluene were added into a reactor under nitrogen atmosphere, and the reactor was stirred at 110° C. for 8 hours. After reaction was complete, the organic layer was extracted with dichloromethane and DI water, and the solvent was removed under reduced distillation. The crude product was separated and purified with a column chromatography using hexane/dichloromethane eluent to give Compound 1-8.

Synthesis Example 3: Synthesis of Compound 1-18 [6,13-diphenylnaphtho[1',8':5,6,7]-s-indaceno[1,2,3-cd]perylene]

(1) Synthesis of Intermediate 1-18B

[Reaction Formula 3-1]

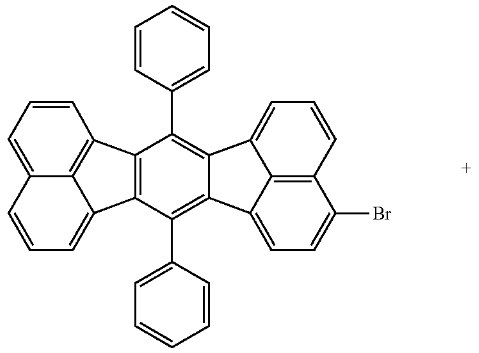

1-18A

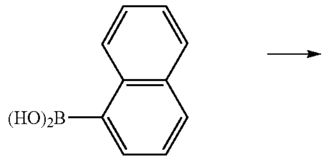

1-1B

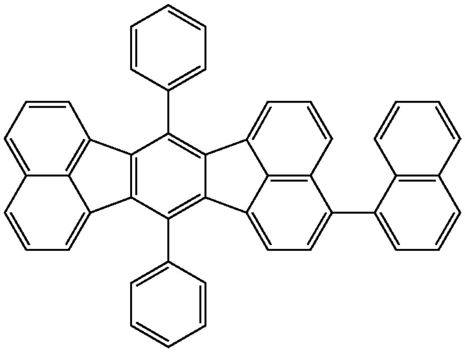

1-18B

Compound 1-18A (1 equivalent) dissolved in a mixed solvent of toluene/ethanol (5:1 by volume ratio) was added into a reactor under nitrogen atmosphere, and then compound 1-1B (1 equivalent) was added into the reactor. Sodium carbonate (3.0 equivalents) dissolved in DI water was added into the reactor, $Pd(PPh_3)_4$ (0.05 equivalent) was added into the reactor, and then the reactor was stirred at 90° C. for 12 hours. After reaction was complete, the organic layer was extracted with dichloromethane and DI water, and the solvent was removed under reduced distillation. The crude product was separated and purified with a column chromatography using a hexane/dichloromethane eluent to give the Intermediate 1-18B.

(2) Synthesis of Compound 1-18

[Reaction Formula 3-2]

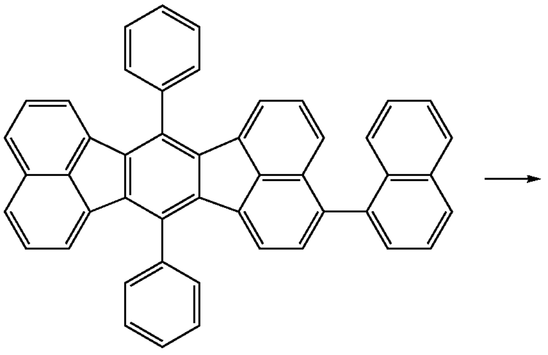

1-18B

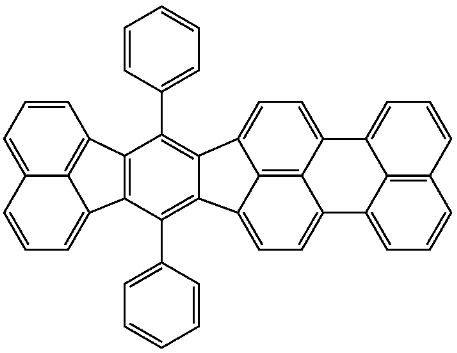

1-18

The Intermediate 1-18B (5 g) dissolved in a mixed solvent of trifluoroacetic acid (500 mL) and trifluoride diethyl etherate (30 mL) was added into a reactor, DDQ (6 g) was added into the reactor, the reactor was purged with nitrogen, and then the compounds were reacted at room temperature for one hour. Ferrocene (5.3 g) was added to the reactor and the reactor was stirred again for one hour. After reaction was complete, the organic layer was extracted with dichloromethane and DI water, and the solvent was removed under reduced distillation. The crude product was separated and purified with a column chromatograph using a hexane/dichloromethane eluent to give the Compound 1-18.

Synthesis Example 4: Synthesis of Compound 1-25 [6,13-bis(dibenzo[b,d]furan-2-yl)-N,N-diphenylnaphtho[1',8':5,6,7]-s-indaceno[1,2,3-cd]perylen-9-amine]

(1) Synthesis of Intermediate 1-25C

[Reaction Formula 4-1]

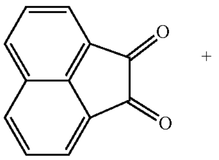

1-25A

-continued

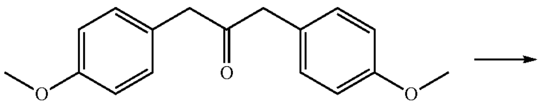

1-25B

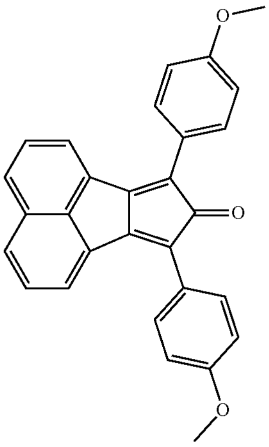

1-25C

Compound 1-25A (1 equivalent) and compound 1-25B (1 equivalent) dissolved in a mixed solvent of toluene/ethanol (10:1 by volume ratio) was added into a reactor under nitrogen atmosphere, and then the reactor was stirred at 70° C. for one hour. A solution of 6M KOH (in ethanol) was added drop wisely to the reactor for 15 minutes. The solution was stirred again for one hour under reflux, cooled down to 0° C. to precipitate a solid. The solid was filtered and washed with ethanol three times to give Intermediate 1-25C.

(2) Synthesis of Intermediate 1-25E

[Reaction Formula 4-2]

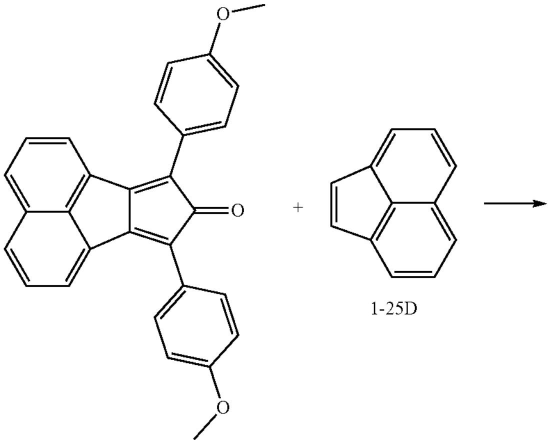

1-25C 1-25D

-continued

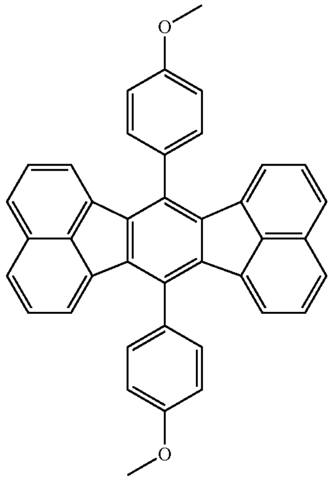

1-25E

The Intermediate 1-25C (1 equivalent) and compound 1-25D (0.9 equivalent) dissolved in xylene was added into a reactor under nitrogen atmosphere, and the solution was stirred for 16 hours under reflux. The solution was cooled down to 0° C., and then was precipitated using ethanol to obtain a solid. The solid was filtered and was dissolved in a mixed solvent of acetone/benzene (1:5 by volume ratio), and then a solution of potassium permanganate (in acetone) was added drop wisely to the reactor until the color of reactants is changed. After reaction was complete, the organic layer was extracted with dichloromethane and DI water, and the solvent was removed under reduced distillation. The crude product was separated and purified with a column chromatography using hexane/dichloromethane eluent to give Intermediate 1-25E.

(3) Synthesis of Intermediate 1-25F

[Reaction Formua 4-3]

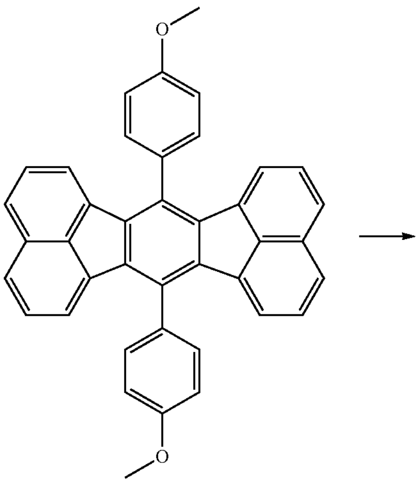

1-25E

-continued

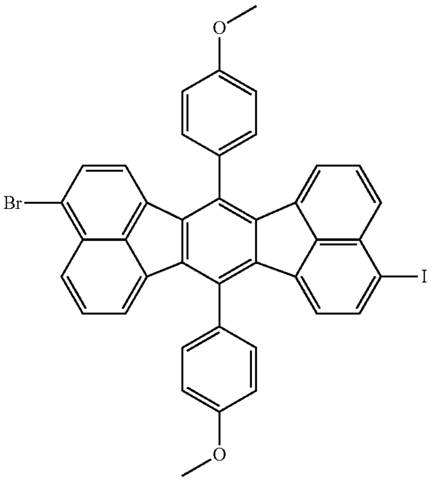

1-25F

The intermediate 1-25E (1 equivalent) dissolved in THF was added into a reactor under nitrogen atmosphere, a solution of N-bromosuccinimide (0.9 equivalent) in THE was added drop wisely to the reactor at room temperature, and the reactor was stirred for one hour. DI waster was added to the reactor to quench the reaction, the solution was cooled down to 0° C. to precipitate a solid, and the solid was filtered and dissolved in THE. A solution of N-bromosuccinimide (0.9 equivalent) in THF added drop wisely to the reactor at room temperature, and the reactor was stirred again for one hour. DI water was added to quench the reaction, and then the solution was cooled down 0° C. and filtered to give Intermediate 1-25F.

(4) Synthesis of Intermediate 1-25G

[Reaction Formula 4-4]

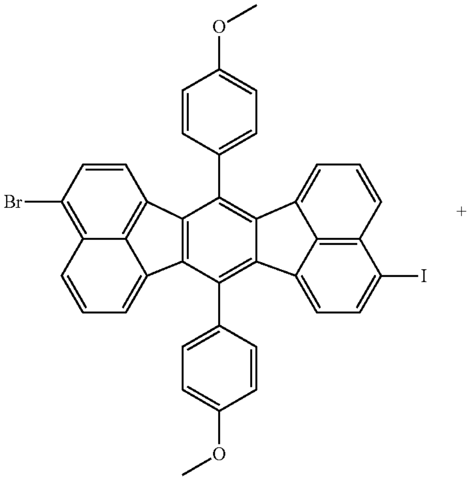

1-25F

-continued

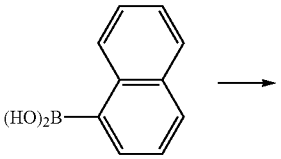

1-1B

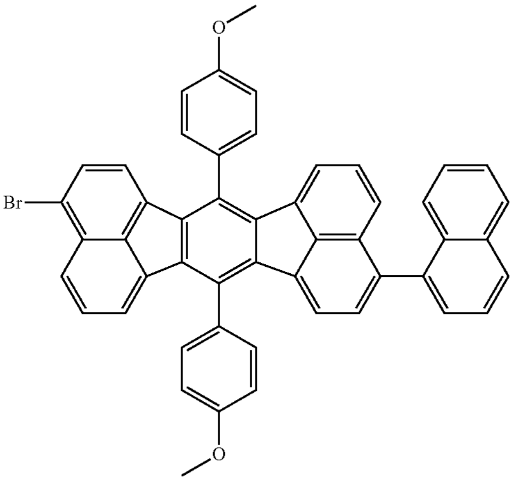

1-25G

The Intermediate 1-25F (1 equivalent) dissolved in a mixed solvent of toluene/ethanol (5:1 by volume ratio) was added into a reactor under nitrogen atmosphere, and then compound 1-1B (1 equivalent) was added into the reactor. Sodium carbonate (3.0 equivalents) dissolved in DI water was added into the reactor, $Pd(PPh_3)_4$ (0.05 equivalent) was added into the reactor, and then the reactor was stirred at 90° C. for 12 hours. After reaction was complete, the organic layer was extracted with dichloromethane and DI water, and the solvent was removed under reduced distillation. The crude product was separated and purified with a column chromatography using a hexane/dichloromethane eluent to give the Intermediate 1-25G.

(5) Synthesis of Intermediate 1-25H

[Reaction Formula 4-5]

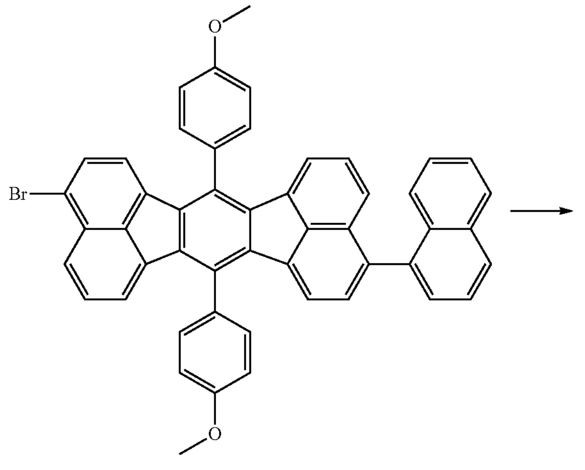

1-25G

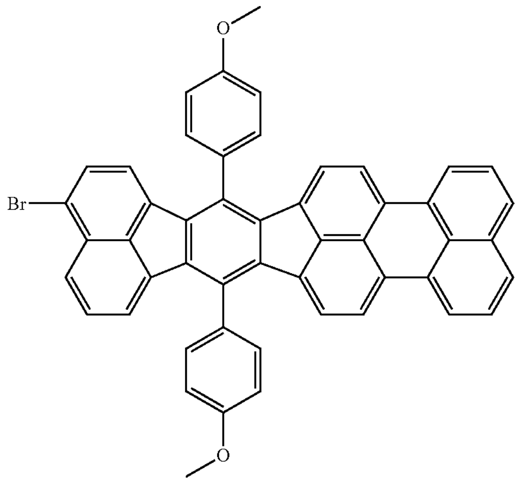

1-25H

The Intermediate 1-25G (5 g) dissolved in a mixed solvent of trifluoroacetic acid (500 mL) and trifluoride diethyl etherate (30 mL) was added into a reactor, DDQ (6 g) was added into the reactor, the reactor was purged with nitrogen, and then the compounds were reacted at room temperature for one hour. Ferrocene (5.3 g) was added to the reactor and the reactor was stirred again for one hour. After reaction was complete, the organic layer was extracted with dichloromethane and DI water, and the solvent was removed under reduced distillation. The crude product was separated and purified with a column chromatograph using a hexane/dichloromethane eluent to give the Intermediate 1-25H.

(6) Synthesis of Compound 1-25

[Reaction Formulae 4-6]

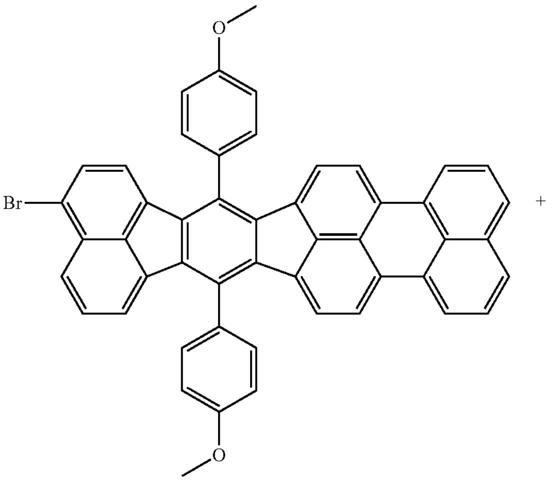

1-25H

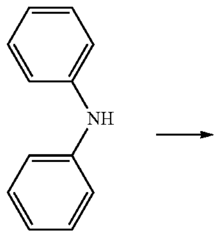

1-1E

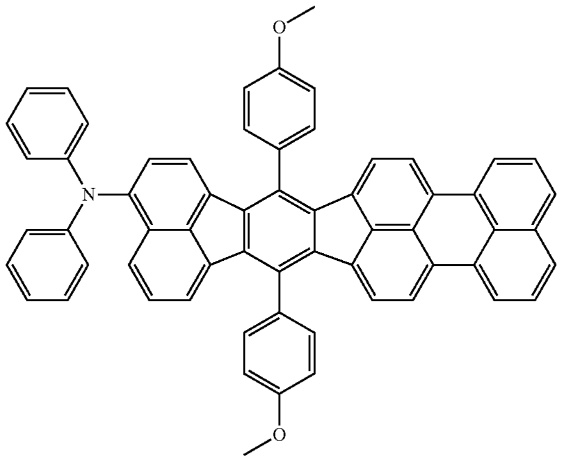

1-25

The Intermediate 1-25H (1 equivalent), compound 1-1E (1.2 equivalents), $Pd_2(dba)_3$, (0.03 equivalent) and sodium t-butoxide (1.4 equivalents) dissolved in toluene were added into a reactor under nitrogen atmosphere, and the reactor was stirred at 110° C. for 8 hours. After reaction was complete, the organic layer was extracted with dichloromethane and DI water, and the solvent was removed under reduced distillation. The crude product was separated and purified with a column chromatography using hexane/dichloromethane eluent to give Compound 1-25.

Synthesis Example 5: Synthesis of Compound 2-7 [6,13-bis(4-methoxyphenyl)-N,N-diphenylnaphtho[1',8':5,6,7]-s-indaceno[1,2,3-cd]perylen-9-amine]

(1) Synthesis of Intermediate 2-7B

[Reaction Formula 5-1]

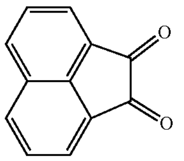

+

1-25A

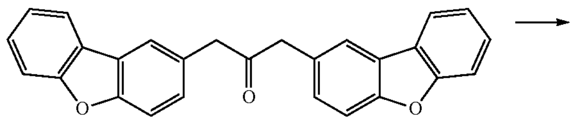

2-7A

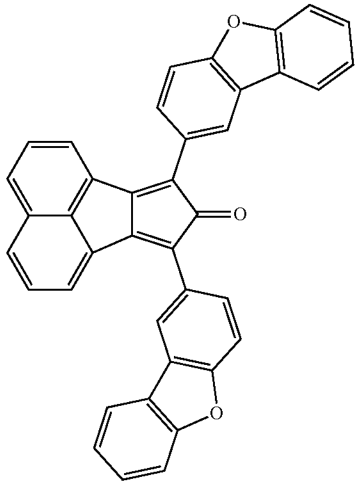

2-7B

Compound 1-25A (1 equivalent) and compound 2-7A (1 equivalent) dissolved in a mixed solvent of toluene/ethanol (10:1 by volume ratio) was added into a reactor under nitrogen atmosphere, and then the reactor was stirred at 70° C. for one hour. A solution of 6M KOH (in ethanol) was added drop wisely to the reactor for 15 minutes. The solution was stirred again for one hour under reflux, cooled down to 0° C. to precipitate a solid. The solid was filtered and washed with ethanol three times to give Intermediate 2-7B.

(2) Synthesis of Intermediate 2-7C

[Reaction Formula 5-2]

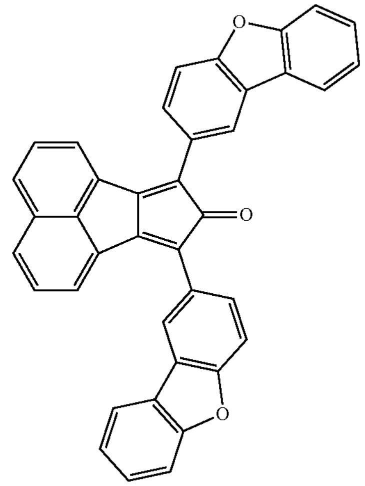

2-7B

+

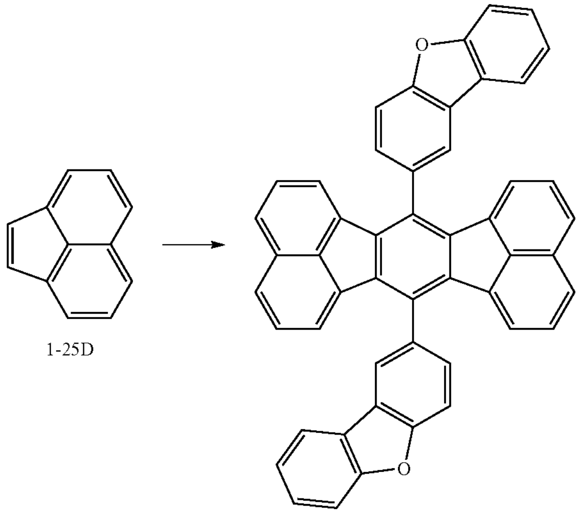

1-25D 2-7C

The Intermediate 2-7B (1 equivalent) and compound 1-25D (0.9 equivalent) dissolved in xylene was added into a reactor under nitrogen atmosphere, and the solution was stirred for 16 hours under reflux. The solution was cooled down to 0° C., and then was precipitated using ethanol to obtain a solid. The solid was filtered and was dissolved in a mixed solvent of acetone/benzene (1:5 by volume ratio), and then a solution of potassium permanganate (in acetone) was added drop wisely to the reactor until the color of reactants is changed. After reaction was complete, the organic layer was extracted with dichloromethane and DI water, and the solvent was removed under reduced distillation. The crude product was separated and purified with a column chromatography using hexane/dichloromethane eluent to give Intermediate 2-7C.

(3) Synthesis of Intermediate 2-7D

[Reaction Formula 5-3]

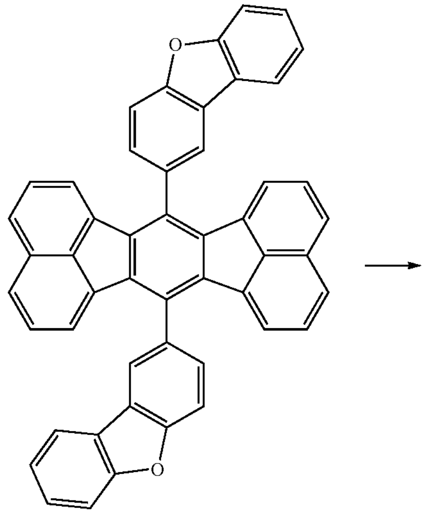

2-7C

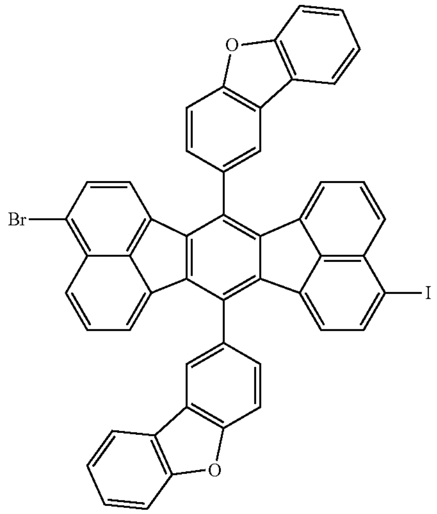

2-7D

The intermediate 2-7C (1 equivalent) dissolved in THF was added into a reactor under nitrogen atmosphere, a solution of N-bromosuccinimide (0.9 equivalent) in THF was added drop wisely to the reactor at room temperature, and the reactor was stirred for one hour. DI waster was added to the reactor to quench the reaction, the solution was cooled down to 0° C. to precipitate a solid, and the solid was filtered and dissolved in THF. A solution of N-bromosuccinimide (0.9 equivalent) in THF added drop wisely to the reactor at room temperature, and the reactor was stirred again for one hour. DI water was added to quench the reaction, and then the solution was cooled down 0° C. and filtered to give Intermediate 2-7D.

(4) Synthesis of Intermediate 2-7E

[Reaction Formula 5-4]

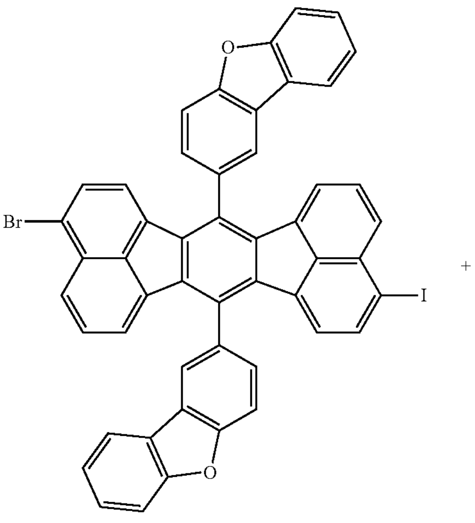

2-7D

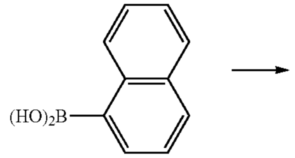

1-1B

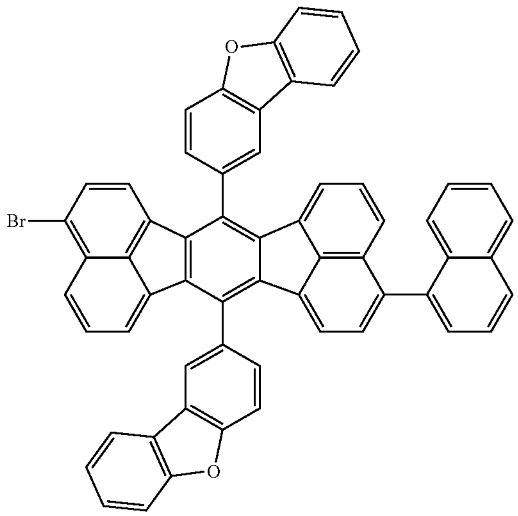

2-7E

The Intermediate 2-7D (1 equivalent) dissolved in a mixed solvent of toluene/ethanol (5:1 by volume ratio) was added into a reactor under nitrogen atmosphere, and then compound 1-1B (1.9 equivalents) was added into the reactor. Sodium carbonate (3.0 equivalents) dissolved in DI water was added into the reactor, $Pd(PPh_3)_4$ (0.05 equivalent) was added into the reactor, and then the reactor was stirred at 90° C. for 12 hours. After reaction was complete, the organic layer was extracted with dichloromethane and DI water, and the solvent was removed under reduced distillation. The crude product was separated and purified with a column chromatography using a hexane/dichloromethane eluent to give the Intermediate 2-7E.

(5) Synthesis of Intermediate 2-7F

[Reaction Formula 5-5]

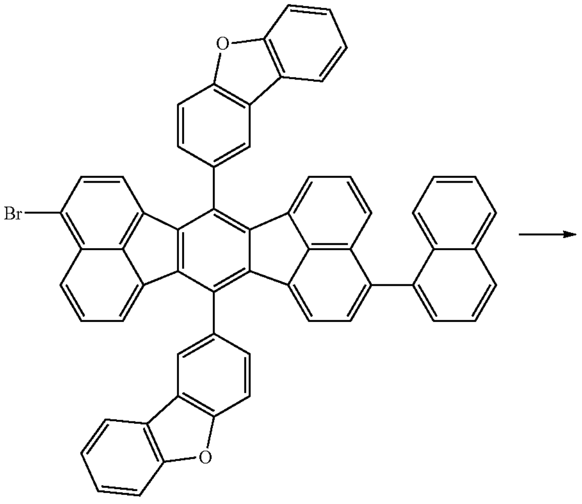

2-7E

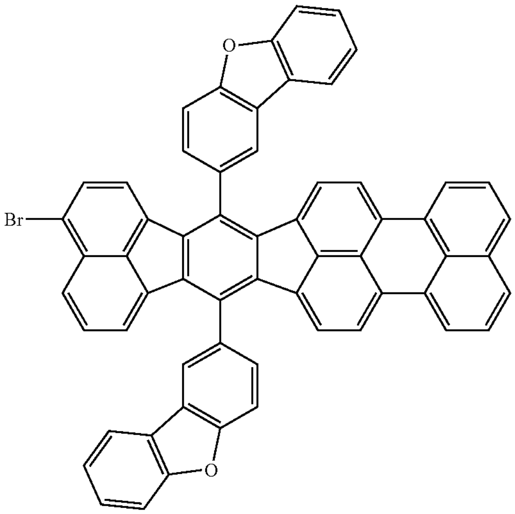

2-7F

The Intermediate 2-7E (5 g) dissolved in a mixed solvent of trifluoroacetic acid (500 mL) and trifluoride diethyl etherate (30 mL) was added into a reactor, DDQ (6 g) was added into the reactor, the reactor was purged with nitrogen, and then the compounds were reacted at room temperature for one hour. Ferrocene (5.3 g) was added to the reactor and the reactor was stirred again for one hour. After reaction was complete, the organic layer was extracted with dichloromethane and DI water, and the solvent was removed under reduced distillation. The crude product was separated and purified with a column chromatograph using a hexane/dichloromethane eluent to give the Intermediate 2-7F.

(6) Synthesis of Compound 2-7

[Reaction Formulae 5-6]

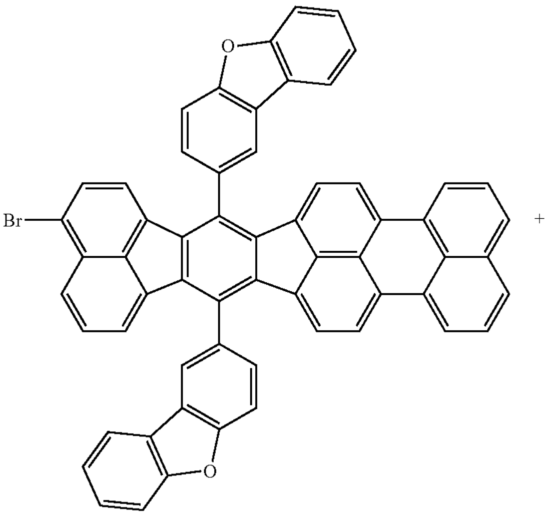

2-7F

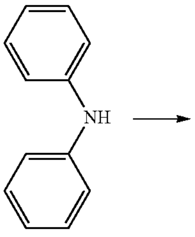

1-1E

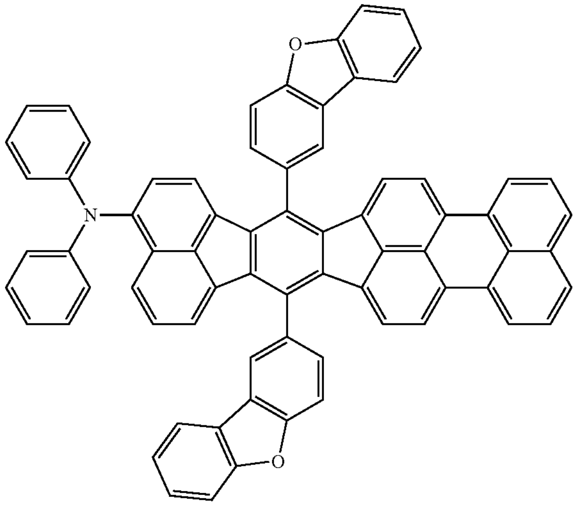

2-7

The Intermediate 2-7F (1 equivalent), compound 1-1E (1.2 equivalents), $Pd_2(dba)_3$, (0.03 equivalent) and sodium t-butoxide (1.4 equivalents) dissolved in toluene were added into a reactor under nitrogen atmosphere, and the reactor was stirred at 110° C. for 8 hours. After reaction was complete, the organic layer was extracted with dichloromethane and DI water, and the solvent was removed under reduced distillation. The crude product was separated and purified with a column chromatography using hexane/dichloromethane eluent to give Compound 2-7.

Experimental Example 1: Measurement of Absorption and Luminescence Wavelength Physical properties such as the maximum absorption wavelength (Abs. $\lambda_{max}$), the maximum photoluminescence wavelength (PL $\lambda_{max}$), the photoluminescence quantum efficiency (PLQY), the HOMO energy level and the LUMO energy level for each of the compounds synthesized in the above Synthesis Examples as well as a green-emitting delayed fluorescent material 2,4,6-tris(4-10H-phenoxazin-10-yl)phenyl)-1,3,5-triazine (tri-PXZ-TRZ) and the referenced compound 1 (Ref. compound 1) and the reference compound 2 (Ref. compound 2) below were measured. Each of the organic compounds was dissolved in toluene to measure the physical properties. Table 1 below indicates the measurement results.

TABLE 1

[Reference compound]

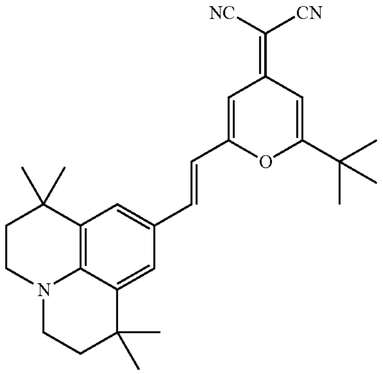 [SMILES: CC(C)(C)C1=CC(=C(C#N)C#N)C=C(/C=C/c2cc3c4c(c2)C(C)(C)CCN4CCC3(C)C)O1]

Physical Property of Organic Compound

| Compound | Abs. $\lambda_{max}{}^{a}$ (nm) | PL $\lambda_{max}{}^{b}$ (nm) | PLQY$^{c}$ (%) | HOMO$^{d}$ (eV) | LUMO$^{d}$ (eV) |
|---|---|---|---|---|---|
| Ref. 1 | 506 | 602 | 68 | -5.2 | -3.1 |
| Ref. 2 | 589 | 594 | 82 | -5.44 | -3.22 |
| 1-1 | 552 | 609 | 86 | -5.52 | -3.35 |
| 1-8 | 556 | 612 | 88 | -5.44 | -3.32 |
| 1-18 | 543 | 587 | 75 | -5.59 | -3.30 |
| 1-25 | 560 | 618 | 95 | -5.48 | -3.31 |
| 2-7 | 559 | 616 | 91 | -5.45 | -3.29 |
| tri-PXZ-TRZ | — | 550 | — | -5.7 | -5.3 |

$^{a}$: measured using UV-Vis spectroscopy in solution state of $10^{-5}$ M in toluene;
$^{b}$: measured usinng fluorescence spectroscopy in solution state of $10^{-6}$ M in toluene;
$^{c}$: measured uinsg Quantarus-QY (Hamamatsu, Japan) in soultion state of $10^{-6}$ M in toluene;
$^{d}$: measured using AC2 apparatus in thin-film state.

As illustrated in Table 1, each of the organic compounds synthesized in the Synthesis Examples has the PL $\lambda_{max}$ in the red wavelength band, excellent PLQY and energy levels suitable for use as the EML in the OLED. Particularly, the organic compounds have Abs. $\lambda_{max}$ overlapping widely with the PL $\lambda_{max}$ of the delayed fluorescent material. Accordingly, it was expected that when the organic compounds were used together with the delayed fluorescent material, it was possible to realize a hyper-fluorescence with excellent color purity and improved luminous efficiency.

Example 1 (Ex. 1): Fabrication of OLED

An OLED in which the Compound 1-1 is applied into an ultimate dopant of an EML was fabricated. An ITO (50 nm) attached glass substrate was washed ozone and was loaded into the vapor system, and then was transferred to a vacuum deposition chamber in order to deposit other layers on the substrate. An organic layer was deposited by evaporation by a heated boat under $10^{-6}$ torr in the following order.

A HIL (HAT-CN; 50 Å); a HTL (NPB, 550 Å); an EBL (3,6-bis(N-carbazolyl)-N-phenyl carbazole; 100 Å); an EML (mCBP (host): tri-PXZ-TRZ: Compound 1-1=70: 29.5:0.5 by weight; 250 Å); a HBL (mCBP; 100 Å); an ETL (TPBi; 250 Å); an EIL (LiF; 10 Å); and a cathode (Al; 1000 Å).

And then, capping layer (CPL) was deposited over the cathode and the device was encapsulated by glass. After deposition of emissive layer and the cathode, the OLED was transferred from the deposition chamber to a dry box for film formation, followed by encapsulation using UV-curable epoxy resin and moisture getter.

Examples 2-5 (Ex. 2-5): Fabrication of OLED

An OLED was fabricated using the same materials as Example 1, except that Compound 1-8 (Ex. 2), Compound 1-18 (Ex. 3), Compound 1-25 (Ex. 4) or Compound 2-7 (Ex. 5) was applied into the EML as the ultimate dopant instead of the Compound 1-1.

Comparative Examples 1-2 (Ref. 1-2): Fabrication of OLED

An OLED was fabricated using the same materials as Example 1, except that Ref. Compound 1 (Ref. 1) or the Ref.

Compound 2 (Ref. 2) was applied into the EML as the ultimate dopant instead of the Compound 1-1.

Experimental Example 2: Measurement of Luminous Properties of OLED

Each of the OLED fabricated by Ex. 1-5 and Ref. 1-2 was connected to an external power source and then luminous properties for all the diodes were evaluated using a constant current source (KEITHLEY) and a photometer PR650 at room temperature. In particular, driving voltage (V), maximum External Quantum Efficiency ($EQE_{max}$, %), CIE color coordinates, maximum electroluminescence wavelength (EL $\lambda_{max}$, nm) and FWHM (nm) at a current density of 10 $mA/cm^2$ were measured. The results thereof are shown in the following Table 2.

TABLE 2

Luminous Properties of OLED

| Sample | Dopant | V | $EQE_{max}$ | CIE (x, y) | $EL_{max}$ | FWHM |
|---|---|---|---|---|---|---|
| Ex. 1 | 1-1 | 4.55 | 10.1 | (0.636, 0.361) | 614 | 46 |
| Ex. 2 | 1-8 | 4.51 | 10.7 | (0.630, 0.367) | 616 | 47 |
| Ex. 3 | 1-18 | 4.52 | 7.4 | (0.553, 0.440) | 592 | 42 |
| Ex. 4 | 1-25 | 4.53 | 11.8 | (0.664,0.333) | 624 | 46 |
| Ex. 5 | 2-7 | 4.48 | 12.4 | (0.658, 0.348) | 621 | 44 |
| Ref. 1 | Ref. 1 | 4.82 | 4.6 | (0.578, 0.414) | 605 | 81 |
| Ref. 2 | Ref. 2 | 4.47 | 5.3 | (0.619, 0.377) | 610 | 26 |

As indicated in Table 2, compared to the OLED in Ref. 1, the OLEDs in Ex. 1-5 lowered their driving voltages up to 7.1%, enhanced their $EQE_{max}$ up to 169.6% and reduced their FWHM significantly, which indicates an increased color purity. In addition, compared to the OLED in Ref. 2, the OLEDs in Ex. 1-5 showed equivalent driving voltages and enhanced their $EQE_{max}$ up to 134.0%. Particularly, we confirmed that the OLEDs in Ex. 1-5 emit a relatively deep red colors compared to the OLEDs in Ref. 1-2. It is possible to manufacture an OLED and an organic light emitting device having the OLED each of which lowers its driving voltages, enhances its luminous efficiency and color purity and implement the hyper-fluorescence with emitting deep red light, by applying the organic compound into the emitting unit It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:

1. An organic compound having the following structure of Chemical Formula 1:

[Chemical Formula 1]

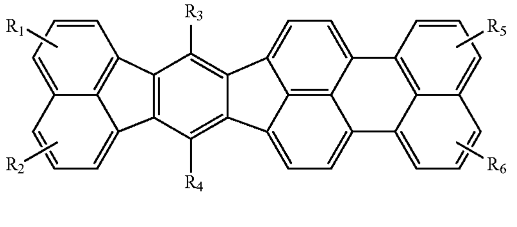

wherein:

$R_1$ is a $C_6$-$C_{30}$ aryl amino group or a $C_3$-$C_{30}$ hetero aryl amino group, and each of an aromatic ring in the $C_6$-$C_{30}$ aryl amino group and a hetero aromatic ring in the $C_3$-$C_{30}$ hetero aryl amino group is independently unsubstituted or substituted with at least one group selected from cyano, $C_1$-$C_{10}$ alkyl, $C_1$-$C_{10}$ alkoxy, $C_6$-$C_{30}$ aryl, and $C_3$-$C_{30}$ hetero aryl, $R_2$ is hydrogen, an unsubstituted or substituted $C_1$-$C_{20}$ alkyl group, an unsubstituted or substituted $C_1$-$C_{20}$ alkoxy group, an unsubstituted or substituted aromatic group or an unsubstituted or substituted hetero aromatic group;

each of $R_3$ and $R_4$ is independently an unsubstituted or substituted aromatic group or an unsubstituted or substituted hetero aromatic group; and each of $R_5$ and $R_6$ is independently hydrogen, an unsubstituted or substituted $C_1$-$C_{10}$ alkyl group, an unsubstituted or substituted $C_1$-$C_{10}$ alkoxy group, an unsubstituted or substituted aromatic group or an unsubstituted or substituted hetero aromatic group, wherein the aromatic group is a group which has one or more $C_6$-$C_{30}$ aryl groups, and wherein the hetero aromatic group is a group which has one or more $C_3$-$C_{30}$ hetero aryl groups.

2. The organic compound of claim 1, wherein the aromatic group comprises a $C_6$-$C_{30}$ aryl group, an alkyl group substituted with one or more $C_6$-$C_{30}$ aryl groups, a $C_6$-$C_{30}$ aryloxyl group, an amino group substituted with one or more $C_6$-$C_{30}$ aryl groups, and combination thereof, and/or wherein the hetero aromatic group comprises a $C_3$-$C_{30}$ hetero aryl group, an alkyl group substituted with one or more $C_3$-$C_{30}$ hetero aryl groups, a $C_3$-$C_{30}$ hetero aryloxyl group, an amino group substituted with one or more $C_3$-$C_{30}$ hetero aryl groups, and combination thereof.

3. The organic compound of claim 1, wherein the organic compound comprises an organic compound having the following structure of Chemical Formula 2:

[Chemical Formula 2]

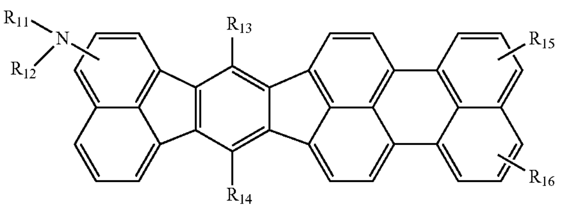

wherein each of $R_{11}$ and $R_{12}$ is independently an unsubstituted or substituted $C_6$-$C_{30}$ aryl group or an unsubstituted or substituted $C_3$-$C_{30}$ hetero aryl group, wherein, if substituted, each of an aromatic ring in the $C_6$-$C_{30}$ aryl group and a hetero aromatic ring in the $C_3$-$C_{30}$ hetero aryl group is independently substituted with at least one group selected from cyano, $C_1$-$C_{10}$ alkyl, $C_1$-$C_{10}$ alkoxy, $C_6$-$C_{30}$ aryl, and $C_3$-$C_{30}$ hetero aryl; each of $R_{13}$ and $R_{14}$ is independently an unsubstituted or substituted $C_6$-$C_{30}$ aryl group, an unsubstituted or substituted $C_3$-$C_{30}$ hetero aryl group, an unsubstituted or substituted $C_7$-$C_{30}$ aryl alkyl group, an unsubstituted or substituted $C_4$-$C_{30}$ hetero aryl alkyl group, an unsubstituted or substituted $C_6$-$C_{30}$ aryloxyl group or an unsubstituted or substituted $C_3$-$C_{30}$ hetero aryloxyl group; and each of $R_{15}$ and $R_{16}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{30}$ hetero aryl group.

4. The organic compound of claim 3, wherein the organic compound comprises an organic compound having the following structure of Chemical Formula 3:

[Chemical Formula 3]

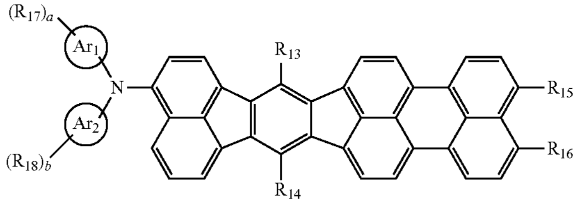

wherein each of $R_{13}$ to $R_{16}$ is independently identical as defined in Chemical Formula 2; each of $Ar_1$ and $Ar_2$ is independently selected from the group consisting of phenyl, biphenyl, naphthyl, anthracenyl, pyridyl, carbazolyl, acridinyl, phenazinyl, phenoxazinyl, dibenzofuranyl and dibenzothiophenyl; each of $R_{17}$ and $R_{18}$ is independently hydrogen, cyano, an unsubstituted a $C_1$-$C_{10}$ alkyl group, a $C_1$-$C_{10}$ alkoxy group, a $C_6$-$C_{30}$ aryl group or a $C_3$-$C_{30}$ hetero aryl group; each of a and b is the number of substituent and an integer of 0 to 4.

5. The organic compound of claim 1, wherein the organic compound is selected from:

1-1

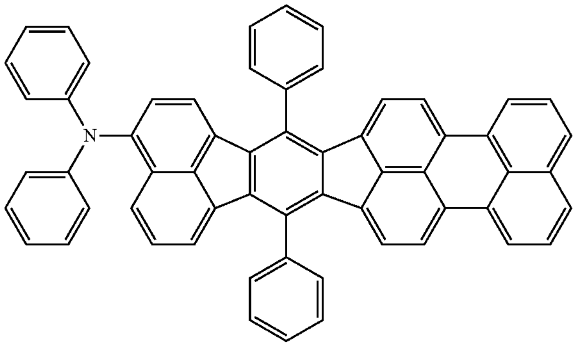

1-2

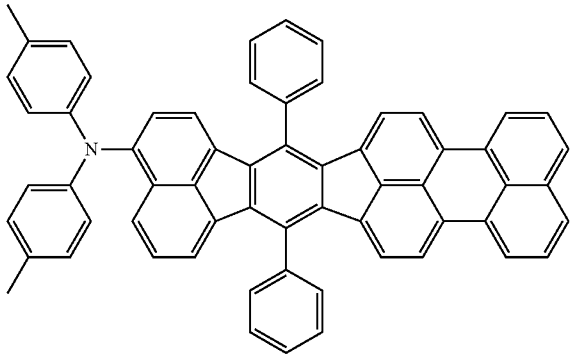

-continued 1-3

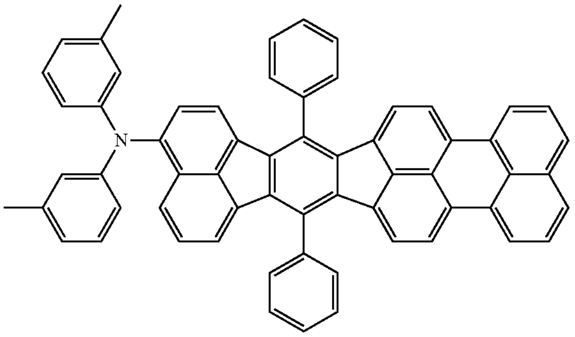

1-4

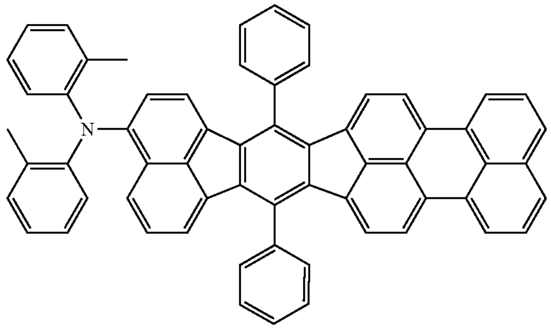

1-5

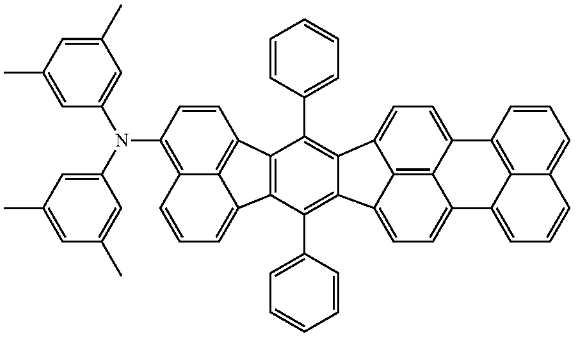

1-6

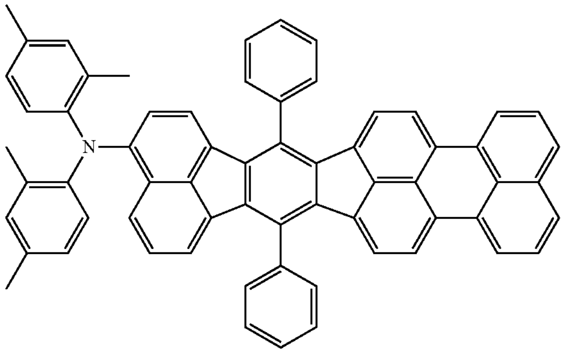

-continued
1-7
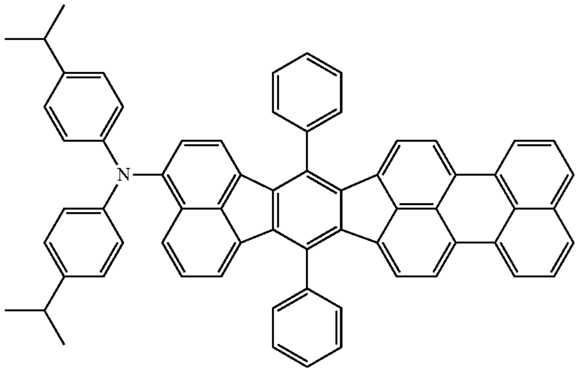
1-8
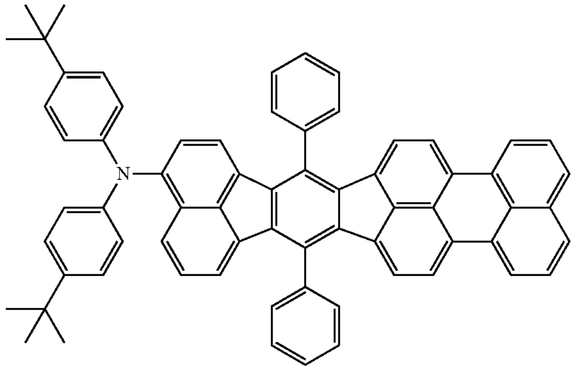
1-9
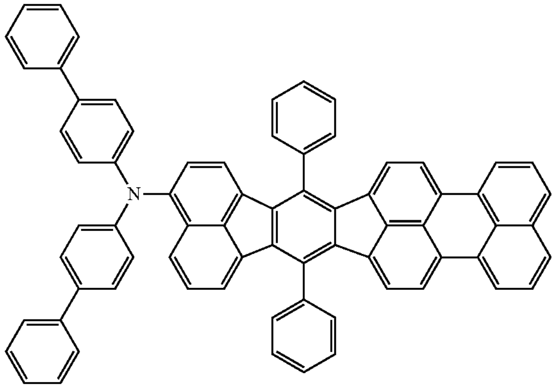
1-10
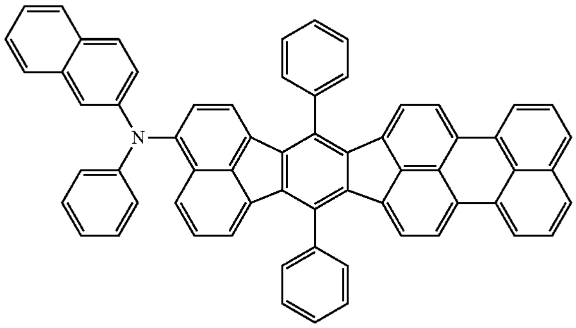
-continued
1-11
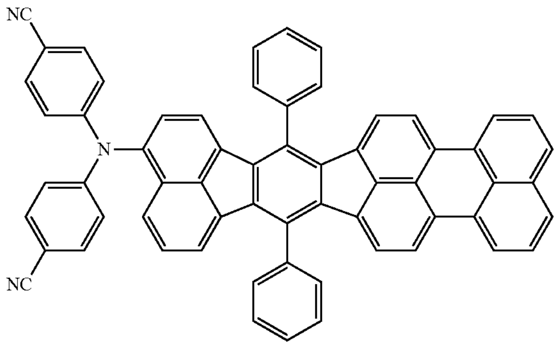
1-12
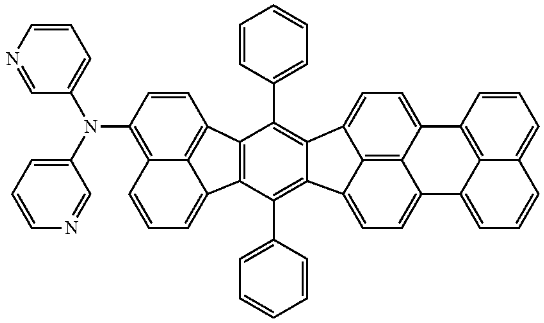
1-13
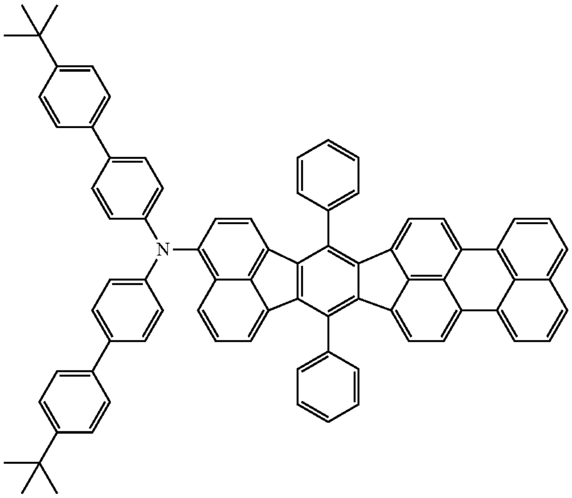
1-14
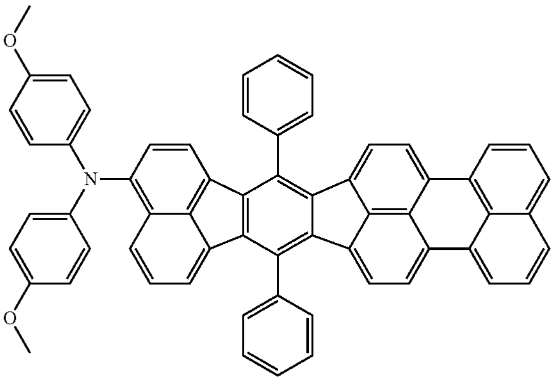

-continued
1-15
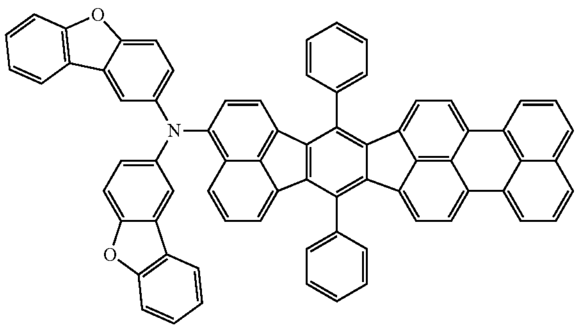
1-16
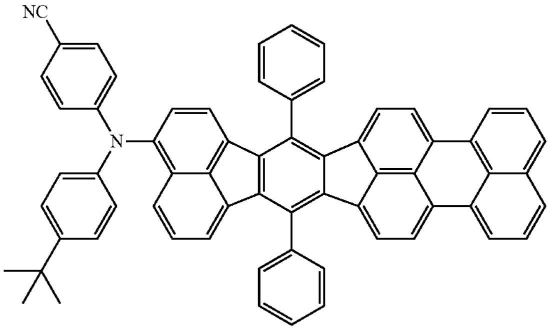
1-17
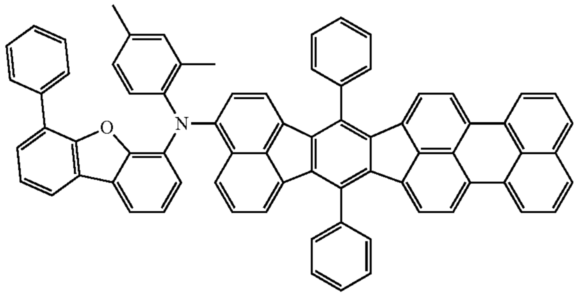
1-19
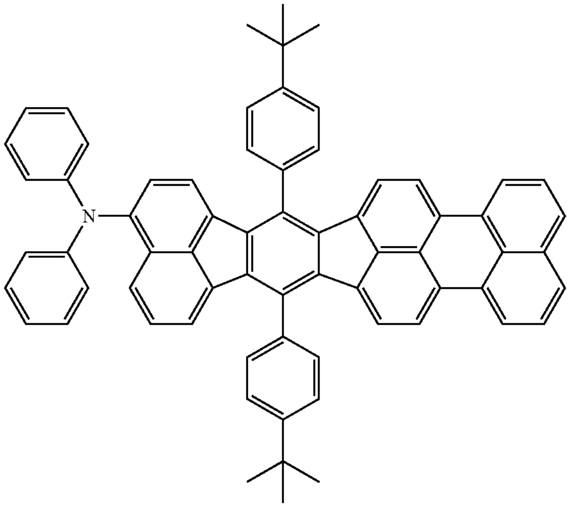
-continued
1-20
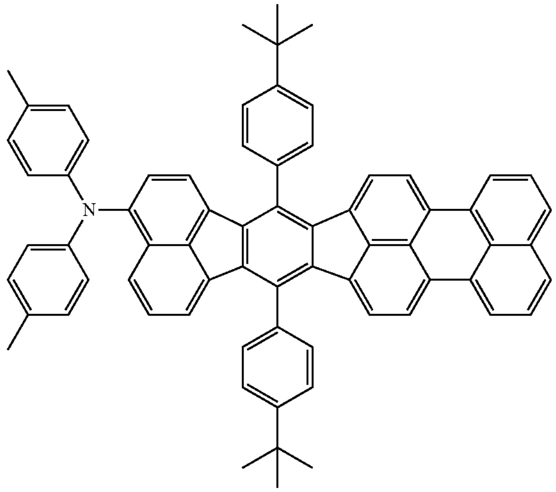
1-21
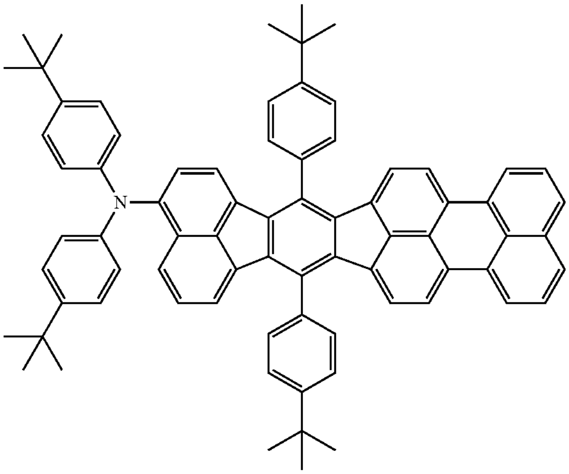
1-22
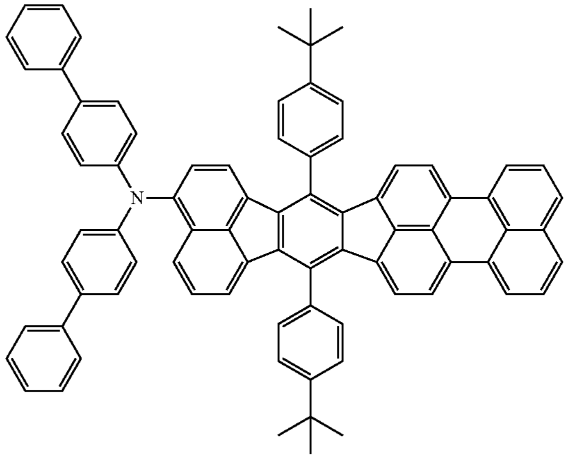

-continued
1-23
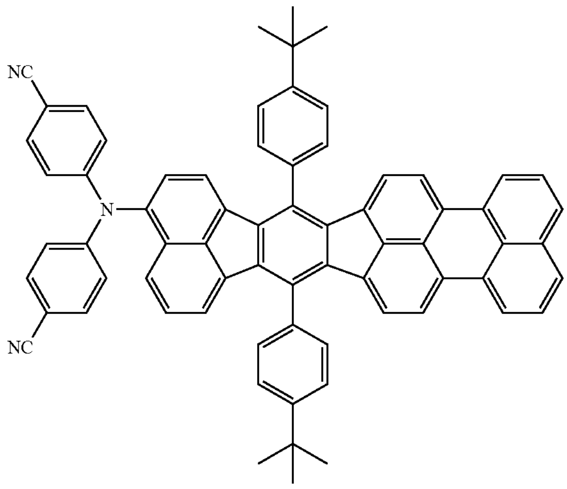
1-24
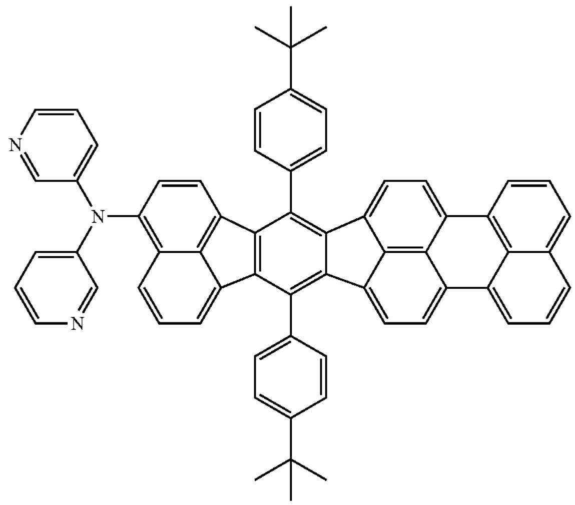
1-25
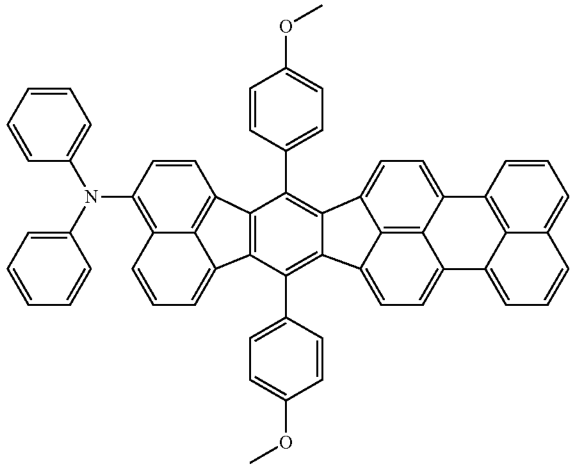
-continued
1-26
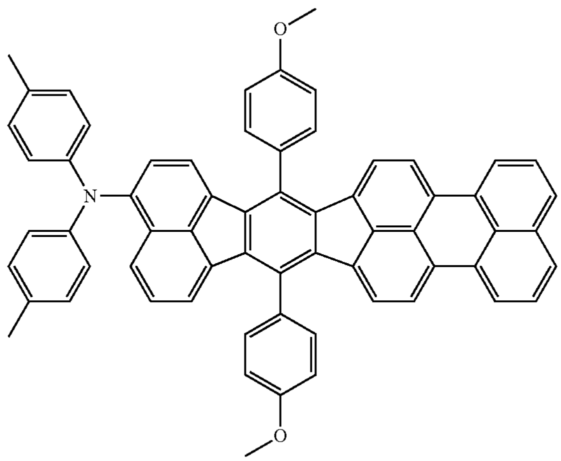
1-27
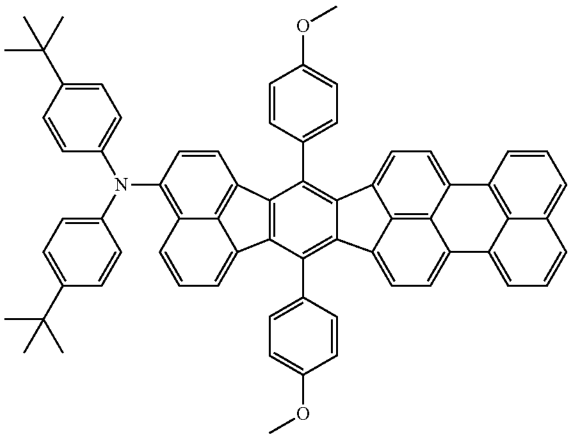
1-28
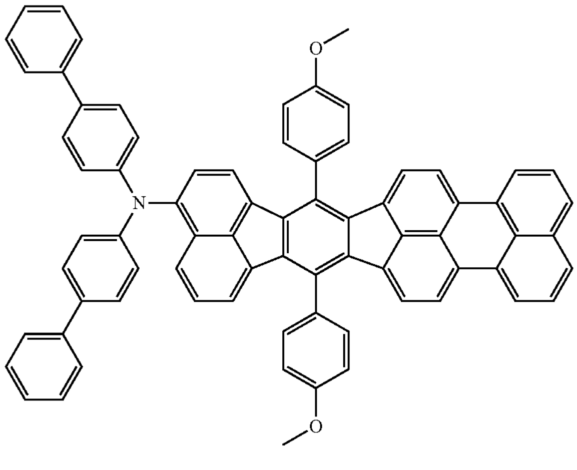

-continued
1-29
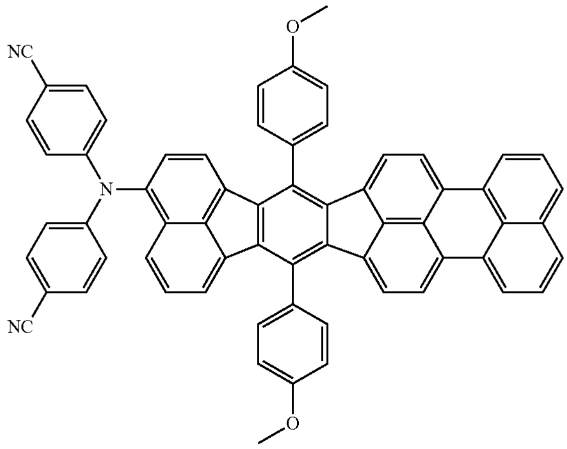
1-30
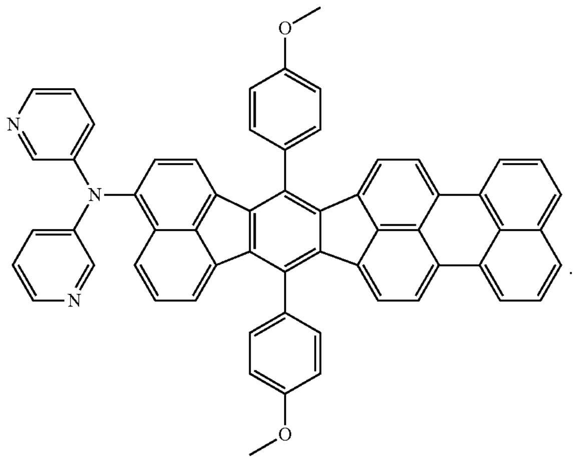
6. The organic compound of claim 1, wherein the organic compound is selected from:
2-1
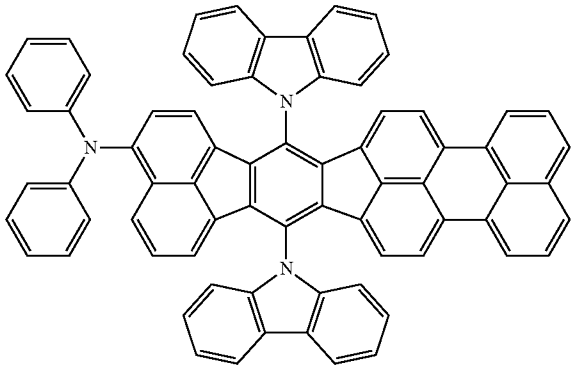
-continued
2-2
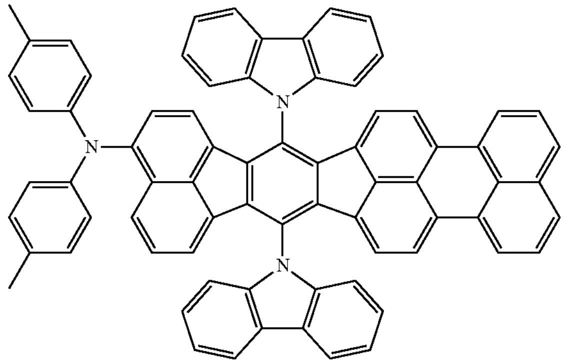
2-3
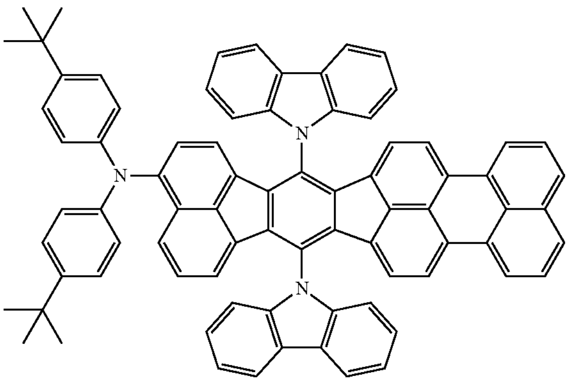
2-4
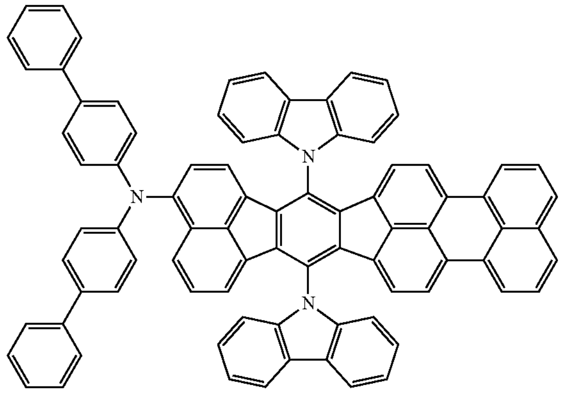
2-5
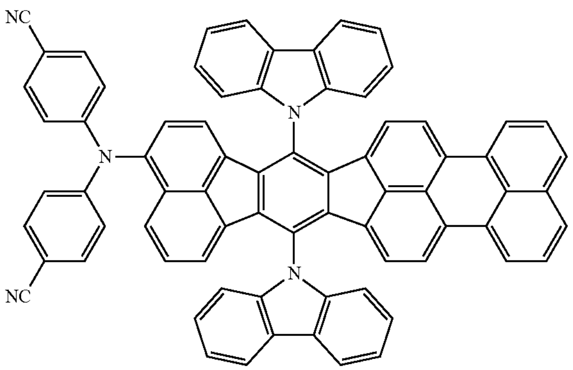

-continued
2-6
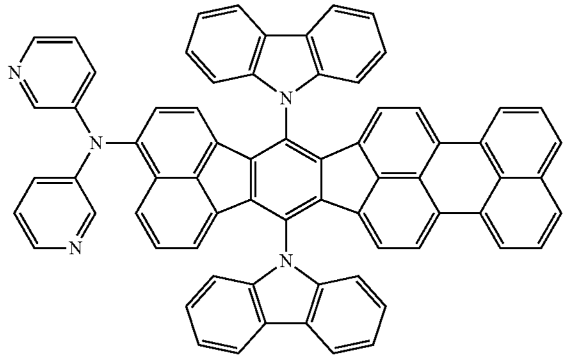
2-7
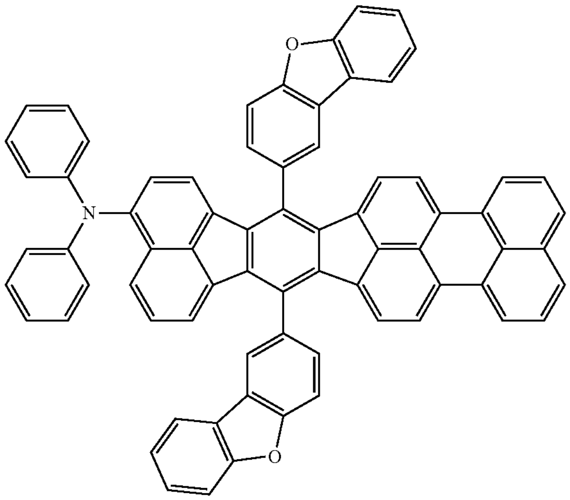
2-8
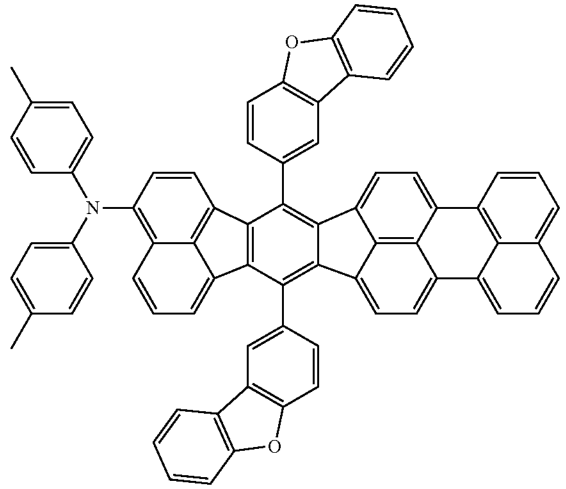
-continued
2-9
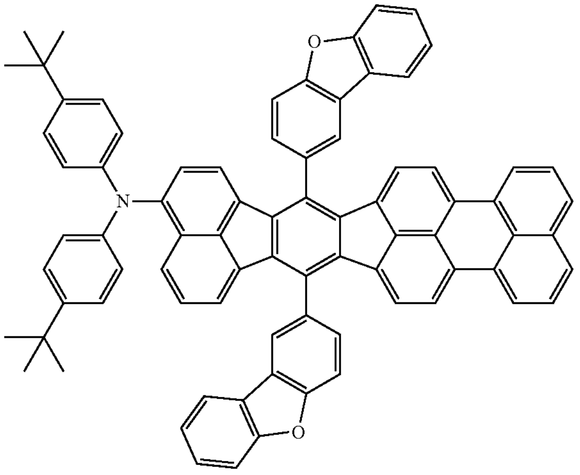
2-10
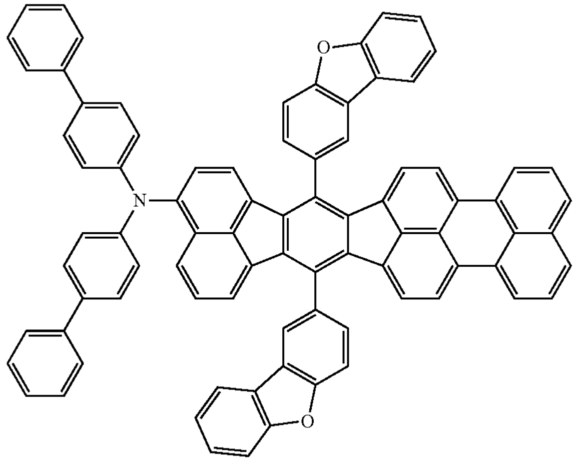
2-11
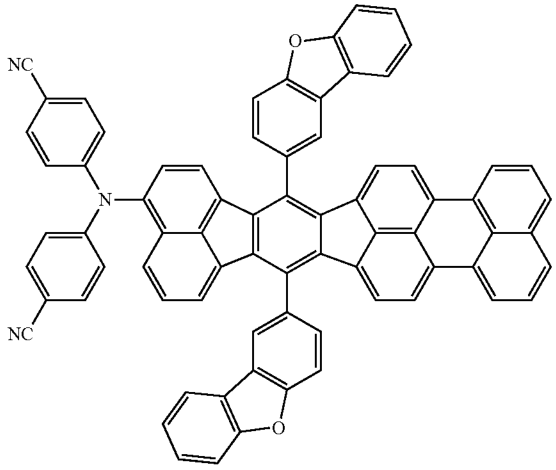

-continued
2-12
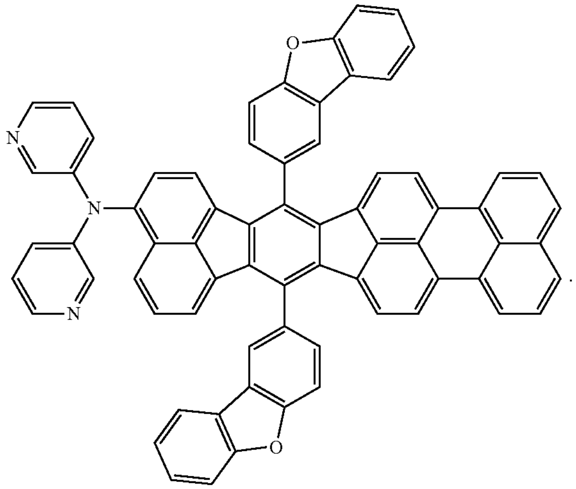
7. The organic compound of claim 1, wherein the organic compound is selected from:
3-1
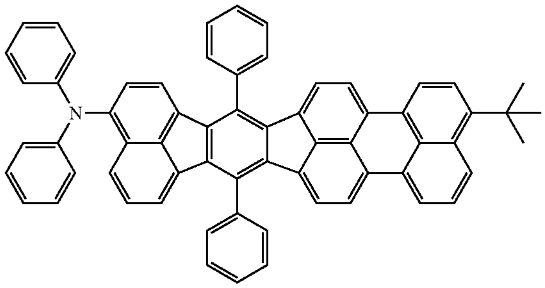
3-2
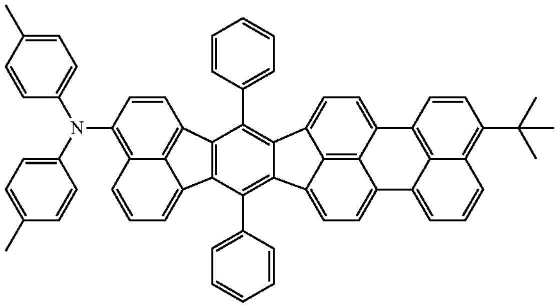
3-3
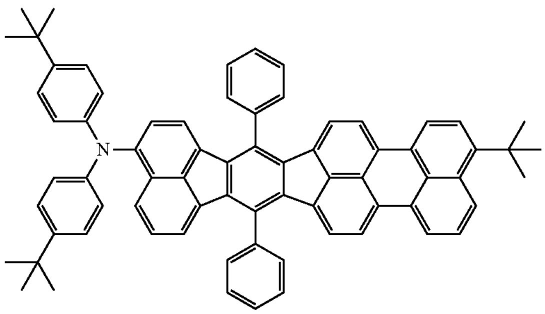
3-4
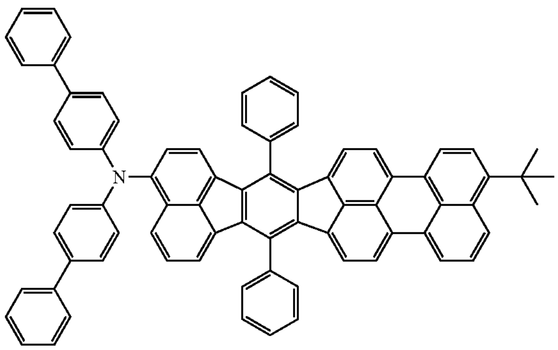

-continued
3-5
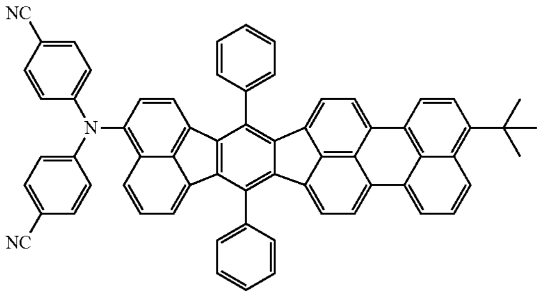
3-6
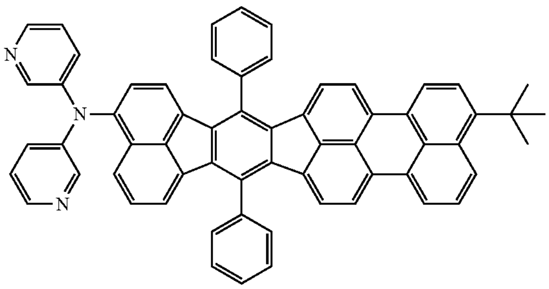
3-7
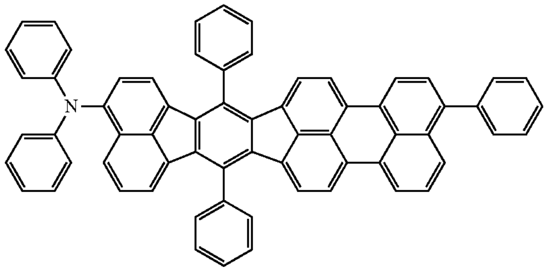
3-8
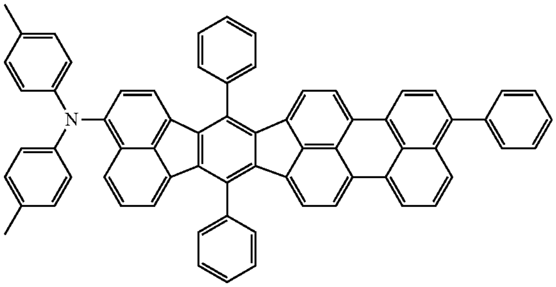
3-9
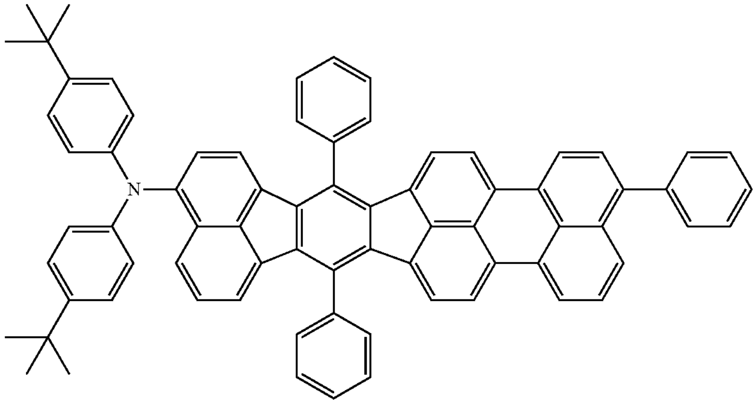
3-10
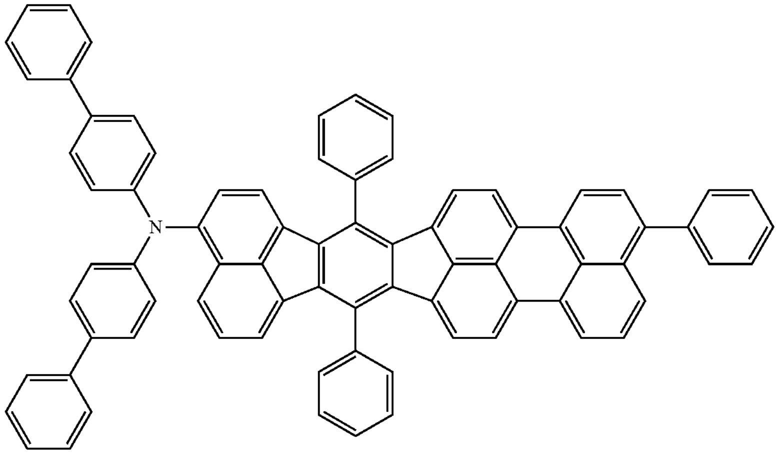

-continued 3-11

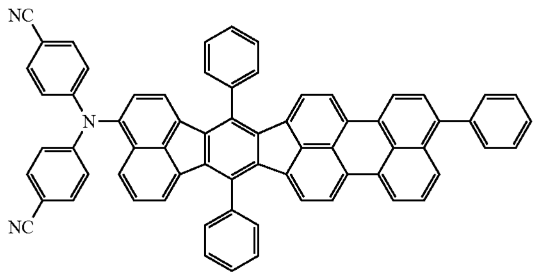

3-12

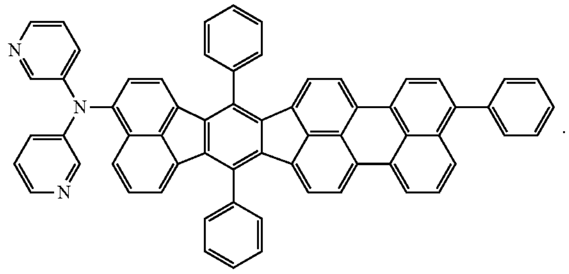

8. The organic compound of claim 1, wherein the organic compound has a maximum photoluminescence wavelength between about 580 nm and about 650 nm.

9. An organic light emitting diode, comprising:

a first electrode;

a second electrode facing the first electrode; and at least one emitting unit disposed between the first and second electrodes and comprising a first emitting material layer, wherein the first emitting material layer comprises an organic compound having the following structure of Chemical Formula 1:

[Chemical Formula 1]

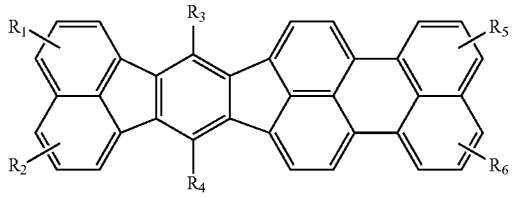

wherein:

$R_1$ is a $C_6$-$C_{30}$ aryl amino group or a $C_3$-$C_{30}$ hetero aryl amino group, and each of an aromatic ring in the $C_6$-$C_{30}$ aryl amino group and a hetero aromatic ring in the $C_3$-$C_{30}$ hetero aryl amino group is independently unsubstituted or substituted with at least one group selected from cyano, $C_1$-$C_{10}$ alkyl, $C_1$-$C_{10}$ alkoxy, $C_6$-$C_{30}$ aryl, and $C_3$-$C_{30}$ hetero aryl, $R_2$ is hydrogen, an unsubstituted or substituted $C_1$-$C_{20}$ alkyl group, an unsubstituted or substituted $C_1$-$C_{20}$ alkoxy group, an unsubstituted or substituted aromatic group or an unsubstituted or substituted hetero aromatic group; each of $R_3$ and $R_4$ is independently an unsubstituted or substituted aromatic group or an unsubstituted or substituted hetero aromatic group; and each of $R_5$ and $R_6$ is independently hydrogen, an unsubstituted or substituted $C_1$-$C_{10}$ alkyl group, an unsubstituted or substituted $C_1$-$C_{10}$ alkoxy group, an unsubstituted or substituted aromatic group or an unsubstituted or substituted hetero aromatic group wherein the aromatic group is a group which has one or more $C_6$-$C_{30}$ aryl groups, and wherein the hetero aromatic group is a group which has one or more $C_3$-$C_{30}$ hetero aryl groups.

10. The organic light emitting diode of claim 9, wherein the aromatic group comprises a $C_6$-$C_{30}$ aryl group, an alkyl group substituted with one or more $C_6$-$C_{30}$ aryl groups, a $C_6$-$C_{30}$ aryloxyl group, an amino group substituted with one or more $C_6$-$C_{30}$ aryl groups, and combination thereof, and/or wherein the hetero aromatic group comprises a $C_3$-$C_{30}$ hetero aryl group, an alkyl group substituted with one or more $C_3$-$C_{30}$ hetero aryl groups, a $C_3$-$C_{30}$ hetero aryloxyl group, an amino group substituted with one or more $C_3$-$C_{30}$ hetero aryl groups, and combination thereof.

11. The organic light emitting diode of claim 9, wherein the organic compound comprises an organic compound having the following structure of Chemical Formula 2:

[Chemical Formula 2]

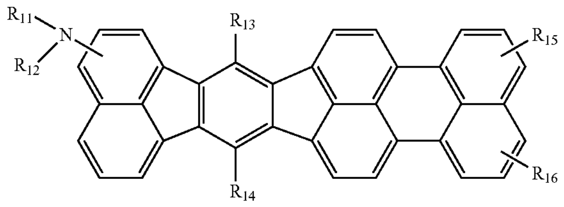

wherein each of $R_{11}$ and $R_{12}$ is independently an unsubstituted or substituted $C_6$-$C_{30}$ aryl group or an unsubstituted or substituted $C_3$-$C_{30}$ hetero aryl group, wherein, if substituted, each of an aromatic ring in the $C_6$-$C_{30}$ aryl group and a hetero aromatic ring in the $C_3$-$C_{30}$ hetero aryl group is independently substituted with at least one group selected from cyano, $C_1$-$C_{10}$ alkyl, $C_1$-$C_{10}$ alkoxy, $C_6$-$C_{30}$ aryl, and $C_3$-$C_{30}$ hetero aryl; each of $R_{13}$ and $R_{14}$ is independently an unsubstituted or substituted $C_6$-$C_{30}$ aryl group, an unsubstituted or substituted $C_3$-$C_{30}$ hetero aryl group, an unsubstituted or substituted $C_7$-$C_{30}$ aryl alkyl group, an unsubstituted or substituted $C_4$-$C_{30}$ hetero aryl alkyl group, an unsubstituted or substituted $C_6$-$C_{30}$ aryloxyl group or an unsubstituted or substituted $C_3$-$C_{30}$ hetero aryloxyl group; and each of $R_{15}$ and $R_{16}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{30}$ hetero aryl group.

12. The organic light emitting diode of claim 11, wherein the organic compound comprises an organic compound having the following structure of Chemical Formula 3:

[Chemical Formula 3]

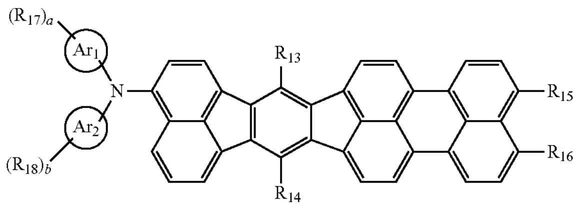

wherein each of $R_{13}$ to $R_{16}$ is independently identical as defined in Chemical Formula 2; each of $Ar_1$ and $Ar_2$ is independently selected from the group consisting of phenyl, biphenyl, naphthyl, anthracenyl, pyridyl, carbazolyl, acridinyl, phenazinyl, phenoxazinyl, dibenzofuranyl and dibenzothiophenyl; each of $R_{17}$ and $R_{18}$ is independently hydrogen, cyano, a $C_1$-$C_{10}$ alkyl group, a $C_1$-$C_{10}$ alkoxy group, a $C_6$-$C_{30}$ aryl group or a $C_3$-$C_{30}$ hetero aryl group; each of a and b is the number of substituent and an integer of 0 (zero) to 4.

13. The organic light emitting diode of claim 9, wherein the first emitting material layer comprises a first compound and a second compound, wherein an excited singlet energy level of the first compound is higher than an excited singlet energy level of the second compound, and wherein the second compound comprises the organic compound.

14. The organic light emitting diode of claim 9, wherein the first emitting material layer comprises a first compound, a second compound and a third compound, and wherein the second compound comprises the organic compound.

15. The organic light emitting diode of claim 14, wherein the second compound has a maximum absorption wavelength between about 530 nm and about 590 nm and the third compound has a maximum photoluminescence wavelength between about 520 nm and about 610 nm.

16. The organic light emitting diode of claim 14, wherein an energy bandgap between an excited singlet energy level and an excited triplet energy level of the third compound is less than or equal to about 0.3 eV.

17. The organic light emitting diode of claim 13, further comprises a second emitting material layer disposed between the first electrode and the first emitting material layer or between the first emitting material layer and the second electrode, and wherein the second emitting material layer comprises a fourth compound and a fifth compound.

18. The organic light emitting diode of claim 17, wherein the second compound has a maximum absorption wavelength between about 530 nm and about 590 nm and the fifth compound has a maximum photoluminescence wavelength between about 520 nm and about 610 nm.

19. The organic light emitting diode of claim 17, further comprises a third emitting material layer disposed oppositely to the first emitting material layer with respect to the second emitting material layer, and wherein the third emitting material layer comprises a sixth compound and a seventh compound.

20. The organic light emitting diode of claim 19, wherein the seventh compound comprises the organic compound.

21. The organic light emitting diode of claim 9, wherein the at least one emitting unit comprises a first emitting unit disposed between the first and second electrodes, and a second emitting unit disposed between the first emitting unit and the second electrode, wherein the first emitting unit comprises a lower emitting material layer and the second emitting unit comprises an upper emitting material layer, wherein at least one of the lower emitting material layer and the upper emitting material layer comprises the first emitting material layer, and further comprises a charge generation layer disposed between the first emitting unit and the second emitting unit.

22. An organic light emitting device, comprising:

a substrate; and an organic light emitting diode of claim 9 and over the substrate.

* * * * *